(12) United States Patent
Yang et al.

(10) Patent No.: US 10,428,055 B2
(45) Date of Patent: Oct. 1, 2019

(54) SUBSTITUTED PIPERIDINES HAVING GPR119 AGONISTIC ACTIVITY

(71) Applicant: DONG-A ST CO., LTD., Seoul (KR)

(72) Inventors: Jae Sung Yang, Seoul (KR); Gye Rim Baek, Gyeonggi-do (KR); Yoon Jung Kim, Gyeonggi-do (KR); Chi Young Ahn, Seoul (KR); Jae Young Lee, Gyeonggi-do (KR); Il Hoon Jung, Gyeonggi-do (KR); Mi Kyung Kim, Gyeonggi-do (KR); So Mi Kang, Gyeonggi-do (KR); Hyo Ju Lee, Gyeonggi-do (KR); Yu Na Chae, Gyeonggi-do (KR); Ye Hwang Cheong, Seoul (KR); Tae Hyoung Kim, Seoul (KR); Eun Kyoung Yang, Seoul (KR); Moon Ho Son, Gyeonggi-do (KR); Chang Yell Shin, Seoul (KR)

(73) Assignee: DONG-A ST CO., LTD. (KR)

(*) Notice: Subject to any disclaimer, the term of this patent is extended or adjusted under 35 U.S.C. 154(b) by 235 days.

(21) Appl. No.: 15/521,090

(22) PCT Filed: Jul. 24, 2015

(86) PCT No.: PCT/KR2015/007715
§ 371 (c)(1),
(2) Date: Apr. 21, 2017

(87) PCT Pub. No.: WO2016/068453
PCT Pub. Date: May 6, 2016

(65) Prior Publication Data
US 2019/0092763 A1    Mar. 28, 2019

(30) Foreign Application Priority Data

Oct. 27, 2014 (KR) .................. 10-2014-0146462
Jun. 25, 2015 (KR) .................. 10-2015-0090708

(51) Int. Cl.
| | |
|---|---|
| A61K 31/4523 | (2006.01) |
| C07D 413/12 | (2006.01) |
| C07D 417/12 | (2006.01) |
| C07D 413/14 | (2006.01) |
| C07D 417/14 | (2006.01) |
| A61P 3/10 | (2006.01) |

(52) U.S. Cl.
CPC .............. *C07D 413/14* (2013.01); *A61P 3/10* (2018.01); *C07D 417/14* (2013.01)

(58) Field of Classification Search
CPC .................. A61K 31/4523; C07D 413/12; C07D 417/12
USPC ........................................ 514/326; 546/209
See application file for complete search history.

(56) References Cited

U.S. PATENT DOCUMENTS

| | | |
|---|---|---|
| 8,299,241 B2 | 10/2012 | Gharbaoui et al. |
| 2010/0305316 A1 | 12/2010 | Gharbaoui et al. |
| 2011/0212939 A1 | 9/2011 | Bertram et al. |

FOREIGN PATENT DOCUMENTS

| | | |
|---|---|---|
| CA | 2031889 A1 | 6/1991 |
| EP | 0435381 A1 | 7/1991 |
| EP | 0605031 A1 | 7/1994 |
| JP | H04128283 A | 4/1992 |
| JP | 2010511711 A | 4/2010 |
| JP | 2011527334 A | 10/2011 |
| RU | 2051149 C1 | 12/1995 |
| WO | 2004041813 A1 | 5/2004 |
| WO | 2007003962 A2 | 1/2007 |
| WO | 2008081204 A1 | 7/2008 |
| WO | 2008081205 A1 | 7/2008 |
| WO | 2009038974 A1 | 3/2009 |
| WO | 2010004347 A1 | 1/2010 |
| WO | 2010006191 A1 | 1/2010 |
| WO | 2013062835 A1 | 5/2013 |
| WO | WO 16/068453 | * 5/2016 |

OTHER PUBLICATIONS

Jordan, V. C. Nature Reviews: Drug Discovery, 2, 2003, 205.*
Hackam, et al. JAMA, 296(14), 2006, 1731-1732.*
Russian Federation Search Report for RU2017112728 dated May 11, 2018.

(Continued)

*Primary Examiner* — Douglas M Willis
(74) *Attorney, Agent, or Firm* — Lerner, David, Littenberg, Krumholz & Mentlik, LLP

(57) ABSTRACT

The present invention relates to a substituted piperidines represented by following Chemical Formula 1, which have a GPR119 agonistic activity, a method for preparing the same, and a pharmaceutical composition including the same:

[Chemical Formula 1]

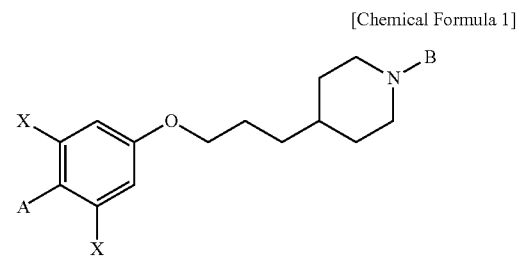

wherein A, B, and X are defined therein.

17 Claims, No Drawings

(56) References Cited

OTHER PUBLICATIONS

Extended European Search Report for Application No. EP15854218.3 dated Mar. 23, 2018.

B. Ahrén, "Review Article: The future of incretin-based therapy: novel avenues-novel targets," Diabetes, Obesity and Metabolism 13 (Suppl. 1), Oct. 2011, pp. 158-166, Blackwell Publishing Ltd.

Baggio, Laurie L., et al., "Biology of Incretins: GLP-1 and GIP," Gastroenterology, May 2007, pp. 2131-2157, vol. 132, Issue 6.

Brown, Kathleen K., et al., "Activation of GPR119 Reduces the Appearance of Labeled Cholesterol in an Oral Fat Tolerance Test," American Diabetes Association, Jun. 9, 2012, p. 1, General Poster Session, American Diabetes Association Association, Alexandria, VA 22311.

Zhu, Zhi-Liang, et al, "A Role for Intestinal Endocrine Cell-Expressed G Protein-Coupled Receptor 119 in Glycemic Control by Enhancing Glucagon-Like Peptide-1 and Glucose-Dependent Insulinotropic Peptide Release," Endocrinology, Jan. 17, 2008, pp. 2038-2047, vol. 149, Issue 5, The Endocrine Society, DOI: 10.1210/en.2007-0966.

Dong, et al., "Insights into the Structural Basis of Endogenous Agonist Activation of Family B G Protein-Coupled Receptors," Molecular Endocrinology, Jun. 2008, pp. 1489-1499, vol. 22, Issue 6, US.

Gallwitz, Baptist MD, Small molecule dipeptidylpeptidase IV inhibitors under investigation for diabetes mellitus therapy, Expert Opinion on Investigational Drugs, Apr. 18, 2011, pp. 723-732, vol. 20, Issue 6, DOI: 10.1517/13543784.2011.576667, Informa UK.

Gallwitz, Baptist, "GLP-1 Agonists and Dipeptidyl-Peptidase IV Inhibitors," Handbook of Experimental Pharmacology 203, Jan. 2011, pp. 53-74, DOI: 10.1007/978-3-642-17214-4_3, Springer-Verlag Berlin Heidelberg.

Gao, J., et al.,"Stimulating β-Cell Replication and Improving Islet Graft Function by AR231453, a GPR119 Agonist," Transplantation Proceedings, Sep. 8, 2011, pp. 3217-3220, 43, Elsevier Inc., New York, NY, DOI:10.1016/j.transproceed.2011.10.021.

Gierczyk, B. & M. Zalas, "Synthesis of Substituted 1,3,4-Thiadiazoles Using Lawesson's Reagent," Organic Preparations and Procedures Inc., Feb. 6, 2009, pp. 213-222, vol. 37, Issue 3, DOI: 10.1080/00304940509354950.

Hansen, Harald. S., et al.,"GPR119 as a fat sensor," Trends in Pharmacological Sciences, Jul. 2012, pp. 374-381, vol. 33, No. 7, Elsevier Ltd.

Hoare, Sam R.J., "Mechanisms of peptide and nonpeptide ligand binding to Class B G-protein-coupled receptors," Reviews, Drug Discovery Today, www.drugdiscoverytoday.com, Mar. 2005, pp. 417-427, vol. 10, Issue 6, Elsevier Ltd.

Houa,b, 1, Zhi-Qiang, et al., "Involvement of chronic stresses in rat islet and Ins-1 cell glucotoxicity induced by intermittent high glucose," Molecular and Cellular Endocrinology 291, Mar. 2008, pp. 71-78, journal homepage: www.elsevier.com/locate/mce, DOI: 10.1016/j.mce.2008.03.004, Elsevier.

Hu, Yan-Wei, et al., "A lincRNA-DYNLRB2-2/GPR119/GLP-1R/ABCA1-dependent signal transduction pathway is essential for the regulation of cholesterol homeostasis," Journal of Lipid Research, Feb. 3, 2014, pp. 681-697, vol. 55, available online at http://www.jlr.org, American Society for Biochemistry and Molecular Biology, Inc.

International Search Report from PCT/KR2015/007715, dated Feb. 29, 2016.

Jones, Robert M., et al., "GPR119 agonists for the treatment of type 2 diabetes," Expert Opinion on Therapeutic Patents, Sep. 28, 2009, pp. 1339-1359, vol. 19, Issue 10, DOI: 10.1517/13543770903153878.

Lauffer, Lina M., et al., "GPR119 Is Essential for Oleoylethanolamide-lnduced Glucagon-Like Peptide-1 Secretion From the Intestinal Enteroendocrine L-Cell," Diabetes, May 2009, pp. 1058-1066, vol. 58, published ahead of print at http://diabetes.diabetesjournals.org, DOI: 10.2337/db08-1237.

Vunez, Derek J., et al, Novel Effects on Lipids of GSK1292263, a GPR119 Agonist, in Type 2 Diabetics, American Diabetes Association, Jun. 9, 2012, p. 1, General Poster Session, American Diabetes Assocation Association, Alexandria, VA.

Overton, Hilary A., et al., "Deorphanization of a G protein-coupled receptor for oleoylethanolamide and its use in the discovery of small-molecule hypophagic agents," Cell Metabolism Mar. 3, 2006, pp. 167-175, Elsevier Inc, DOI: 10.1016/j.cmet.2006.02.004.

Ugarkar, A.G., et al, "Extracting structural requirements for activity of GPR119 agonists: a hologram quantitative structure activity relationship (HQSAR) study," Can. J. Chem., Jul. 2014, pp. 670-676, vol. 92, No. 7, published at www.nrcresearchpress.com/cjc, NRC Research Press.

Yoshida, S., et al.,"The role of small molecule GPR119 agonist, AS1535907, in glucose-stimulated insulin secretion and pancreatic β-cell function," Diabetes, Obesity and Metabolism, Jan. 2011, pp. 34-41, vol. 13, No. 1, Blackwell Publishing Ltd, DOI:10.1111/j.1463-1326.2010.01315.x.

Yoshida, Shigeru, et al,"AS1907417, a novel GPR119 agonist, as an insulinotropic and β-cell preservative agent for the treatment of type 2 diabetes," Biochemical and Biophysical Research Communications, Sep. 15, 2010, pp. 745-751, 400, Elsevier, journal homepage: www.elsevier.com/locate/ybbrc, DOI: 10.1016/j.bbrc.2010.08.141.

* cited by examiner

SUBSTITUTED PIPERIDINES HAVING GPR119 AGONISTIC ACTIVITY

CROSS-REFERENCE TO RELATED APPLICATIONS

This application is a national phase entry under 35 U.S.C. § 371 of International Application No. PCT/KR2015/007715, filed Jul. 24, 2015, which claims priority to Korean Patent Application No. 10-2014-0146462, filed Oct. 27, 2014 and Korean Patent Application No. 10-2015-0090708, filed Jun. 25, 2015, the disclosures of which are incorporated herein by reference.

BACKGROUND OF THE INVENTION

Field of the Invention

The present invention relates to a compound having a GPR119 agonistic activity, a method for preparing the same, and a pharmaceutical composition including the same as an effective component.

Description of Related Art

A metabolic disease refers to a syndrome accompanied by risk factors such as obesity, diabetes, hypertriglyceridemia, hypertension, other cardiovascular diseases and a hemostatic disorder. According to ATP III of the US National Cholesterol Education Program (NCEP) published in 2001, when a patient shows at least three of the following five risk factors, a diagnosis of the metabolic syndrome may be made: ① abdominal obesity, given as waist circumference of 40 inches (102 cm) or more in men, and 35 inches (88 cm) or more in women, ② hypertriglyceridemia, given as triglycerides of 150 mg/dL or more, ③ HDL cholesterol of 40 mg/dL or less in men, and 50 mg/dL or less in women, ④ hypertension, given as blood pressure of 130/85 mmHg or more, and ⑤ fasting glucose of 110 mg/dL or more.

Due to the increase in obese people and sedentary lifestyle, a prevalence rate of diabetes is rapidly increasing around the world, and according to the International Diabetes Federation (IDF), the number of diabetic patients is expected to be explosively increased from 246 millions in 2007 to 435 millions in 2030.

Incretins are gut hormones that are secreted from enteroendocrine cells into the blood within minutes after eating, which include Glucagon-like peptide 1 (GLP-1) and glucose-dependent insulinotropic peptide (GIP). GLP-1 is a peptide hormone with a short half-life of less than 2 minutes, which is secreted by stimulation of L-cells of small intestine upon nutrient ingestion, thereby inducing insulin secretion in pancreatic beta cells. Thus, it has been suggested that essential treatment through improvement in a beta-cell function is possible, which is impossible with the existing therapeutic agents for diabetes (Baggio L L., Drucker D J., Gastroenterology, 2007(132):2131-2157). Accordingly, a lot of studies have been recently made on drugs acting directly on the GLP-1 receptor, or increasing endogenous GLP-1 secretion (Gallwitz B., Handb Exp Pharmacol, 2011(203): 53-74; Gallwitz B., Expert Opin Investig Drugs, 2011(20): 723-32; Jones RM et al., Expert Opin Ther Pat, 2009(19): 1339-1359).

Since the GLP-1 receptor is one of class B G protein-coupled receptors (GPCRs), in which the protein tertiary structure thereof is not identified. Because class B GPCRs have a unique engagement wherein a receptor N-terminus is coupled to a ligand to determine an affinity, they are recognized as being a drug target of which the low molecular synthetic ligand is difficult to be developed (Dong M et al., Mol Endocrinol, 2008(22):1489-1499; Hoare S R., Drug Discov Today, 2005(10):417-427).

Activating G protein-coupled receptor 119 (GPR119) leads to the secretion of gut peptides including GLP-1 (Ahrén B., Diabet Obes Metab, 2011(13):158-166). GPR119 is a member of class A GPCR and therefore is a druggable target for the development of small molecule ligands, as compared with class B. GPR119 agonists have been reported to promote secretion of GLP-1 in small intestines, and directly or indirectly increase insulin secretion in pancreatic beta cells (Lauffer L M. et al., Diabetes, 2009(58):1058-1066; Chu Z L. et al., Endocrinology, 2008(149):2038-2047; Yoshida S. et al., Biochem Biophys Res Commun, 2010 (400):745-751). The increase in insulin secretion following GPR119 activation is partly attributed to the enhanced insulin biosynthesis followed by activating insulin gene promoter (Yoshida S. et al., Diabetes Obes Metab, 2011(13): 34-41). Further, Guo Z. et al. have recently reported that when GPR119 is activated by a low molecular compound, pancreatic beta cell proliferation is increased to increase effectiveness after islet transplantation (Guo Z. et al., Transplant Proc, 2011(43):3217-20). Aside from the function of glycemic control, it was suggested that GPR119 has an important function in recognizing the concentration of fat introduced from the outside in small intestinal epithelial cells to maintain homeostasis of in vivo fat (Schwartz T W. et al, Trends in Pharmacological Sciences, 2012 in press, doi.10.1016/j.tips.2012.03.014). When activated by a low molecular compound, GPR119 activation leads to the suppression of fat absorption in a small intestine, and the improvement of lipid metabolism, indicating that the GPR119 agonist has a therapeutic potential on dyslipidemia (Brown K K. et al., 631-P and Nunez D J. et al., 1084-P in 72$^{nd}$ Scientific Session of American Diabetes Association, Philadelphia, Pa.). Recently, according to Hu Y W, et al., GPR119 has been reported to play an important role in cholesterol homeostasis and an immune reaction in immune cells (Hu Y W et al., J Lipid Res, 2014(55):681-97). Since this shows that GPR119 activation effectively inhibits increased postprandial triglycerides, has an effectiveness of HDL cholesterol increase and LDL cholesterol lowering, maintains cholesterol homeostasis, and controls an immune reaction, the potential as an excellent drug target capable of improving cardiovascular safety as a therapeutic agent for diabetes has been raised. Additionally, as seen in that selective low molecular GPR119 agonists such as PSN632408 inhibit food intake and reduces weight gain and fat mass in high-fat fed rats, GPR119 has been known as a target associated with obesity and related metabolic diseases thereof (Overton H A. et al., Cell Metabolism, 2006(3):167-175).

In summary, since a low molecular drug activating GPR119 has an effective hypoglycemic action and a positive effect on pancreatic beta cells, its value as a therapeutic agent for type 2 diabetes improving lipid metabolism which is a chronic cardiovascular risk factor has been highlighted. Among current leading materials, the clinical development of JNJ-38431055 and GSK1292263 has been discontinued due to loss of efficacy by repeated administration or lack of efficacy, however MBX-2982 is still under phase II development.

Under such background, the present inventors proceeded with a study on a therapeutic agent for a metabolic disease such as diabetes of which the prevalence rate is rapidly increasing around the world, and synthesized novel low molecular compounds activating GPR119, which were identified as having an effective hypoglycemic action and a positive effect on pancreatic beta cells, and thus, have completed the present invention.

BRIEF SUMMARY OF THE INVENTION

The present invention has been made in an effort to provide a novel compound having a GPR119 agonistic activity.

Further, the present invention has been made in an effort to provide a method for preparing the novel compound having a GPR119 agonistic activity.

Additionally, the present invention has been made in an effort to provide a pharmaceutical composition including the novel compound as an effective component, and being useful for treatment or prevention of a metabolic disease.

DETAILED DESCRIPTION OF THE INVENTION

Hereinafter, the present invention will be described in detail.

An exemplary embodiment of the present invention provides a compound represented by following Chemical Formula 1:

[Chemical Formula 1]

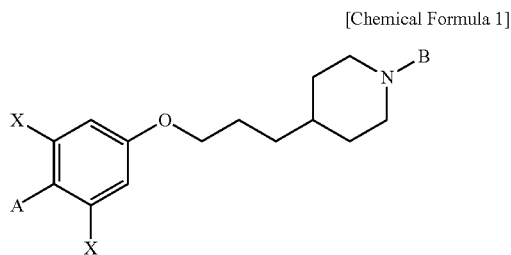

wherein

A is oxadiazole, dihydrooxazole, thiazole or thiadiazole, optionally substituted by one or more substituents selected from the group consisting of hydrogen, halogen, C1-C6 straight chain or branched chain alkyl and C1-C6 alcohol, the alkyl or alcohol group being optionally substituted by hydrogen, halogen or a C1-C6 alkoxy group;

B is pyridine, pyrimidine, pyrazine or oxadiazole, optionally substituted by one or more substituents selected from the group consisting of hydrogen, halogen, C1-C6 straight chain or branched chain alkyl, C1-C6 alcohol, C1-C6 alkoxy and oxadiazole groups, the alkyl, alcohol, alkoxy or oxadiazole group being optionally substituted by hydrogen, halogen or a C1-C6 alkyl or C1-C6 alkoxy group; and X is independently F, Cl, Br or I, preferably F; or an isomer thereof, or a pharmaceutically acceptable salt thereof.

According to one embodiment of the present invention, in the Chemical Formula 1, A may be

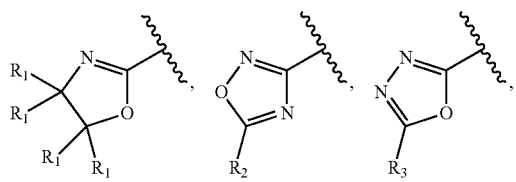

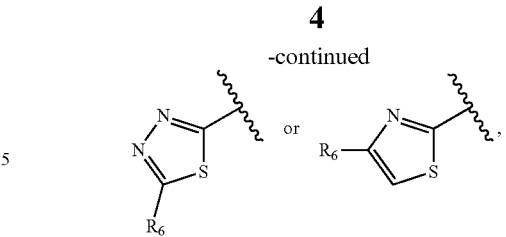

wherein $R_1$ to $R_6$ are independently one or more substituents selected from the group consisting of hydrogen, halogen, C1-C6 straight chain or branched chain alkyl and C1-C6 alcohol, the alkyl or alcohol group being optionally substituted by hydrogen, halogen or a C1-C6 alkoxy group.

According to one embodiment of the present invention, in the Chemical Formula 1, B may be

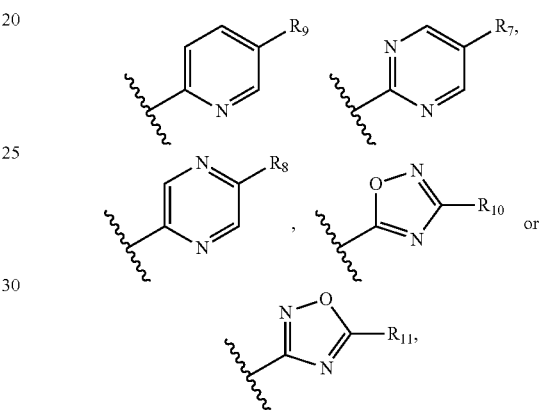

wherein $R_7$ to $R_{11}$ are optionally substituted by one or more substituents selected from the group consisting of hydrogen, halogen, C1-C6 straight chain or branched chain alkyl, C1-C6 alcohol, C1-C6 alkoxy and oxadiazole groups, the C1-C6 alkyl, C1-C6 alcohol, C1-C6 alkoxy or oxadiazole group being optionally substituted by hydrogen, halogen, C1-C6 alkyl or C1-C6 alkoxy group.

More preferably, according to one embodiment of the present invention, the compound wherein in the Chemical Formula 1, A is C1-C6 alkyl, for example, oxadiazole substituted by an isopropyl group; B is pyrimidine substituted by C1-C6 alkyl, for example, an ethyl group; and X is halogen, for example F; or the isomer thereof, or the pharmaceutically acceptable salt thereof, may be provided.

The term 'halogen' as used herein refers to fluorine, chlorine, bromine or iodine.

The term 'alkyl' as used herein refers to a straight chain or branched chain hydrocarbon residue, unless otherwise stated. The examples of the C1-C6 alkyl include methyl, ethyl, propyl, isopropyl, butyl, isobutyl, pentyl, hexyl, and the like.

The term 'alkoxy' as used herein includes an alkyl-oxygen radical having alkyl as defined above, unless otherwise stated. The examples of the C1-C6 alkoxy include methoxy, ethoxy, propoxy, butoxy, pentoxy, and the like.

The term 'heterocycle' or 'heterocyclic' as used herein refers to a 5 to 13 membered heteroaromatic or non-aromatic compound including 1 to 3 hetero atoms selected from the group consisting of N, O and S, unless otherwise stated.

More preferably, according to one embodiment of the present invention, the compound represented by the above Chemical Formula 1 may be selected from the group consisting of following compounds:

2-(4-(3-(1-(5-ethylpyrimidin-2-yl)piperidin-4-yl)propoxy)-2,6-difluorophenyl)-4,5-dihydrooxazole, (R)-2-(4-(3-(1-(5-ethylpyrimidin-2-yl)piperidin-4-yl)propoxy)-2,6-difluorophenyl)-4-methyl-4,5-dihydrooxazole, (S)-2-(4-(3-(1-(5-ethylpyrimidin-2-yl)piperidin-4-yl)propoxy)-2,6-difluorophenyl)-4-methyl-4,5-dihydrooxazole, (S)-2-(4-(3-(1-(5-ethylpyrimidin-2-yl)piperidin-4-yl)propoxy)-2,6-difluorophenyl)-5-methyl-4,5-dihydrooxazole, (R)-2-(4-(3-(1-(5-ethylpyrimidin-2-yl)piperidin-4-yl)propoxy)-2,6-difluorophenyl)-5-methyl-4,5-dihydrooxazole, 2-(4-(3-(1-(5-ethylpyrimidin-2-yl)piperidin-4-yl)propoxy)-2,6-difluorophenyl)-5,5-dimethyl-4,5-dihydrooxazole, (R)-(2-(4-(3-(1-(5-ethylpyrimidin-2-yl)piperidin-4-yl)propoxy)-2,6-difluorophenyl)-4,5-dihydrooxazol-5-yl)methanol, (S)-(2-(4-(3-(1-(5-ethylpyrimidin-2-yl)piperidin-4-yl)propoxy)-2,6-difluorophenyl)-4,5-dihydrooxazol-5-yl)methanol, (R)-3-(2-(4-(3 -(3,5-difluoro-4-(5-methyl-4,5-dihydrooxazol-2-yl)phenoxy)propyl)piperidin -1-yl)pyrimidin-5-yl)-5-isobutyl-1,2,4-oxadiazole, (R)-5-(4-(3 -(3,5-difluoro-4-(4-methyl-4,5 -dihydrooxazol-2-yl)phenoxy)propyl)piperidin -1-yl)-3-isopropyl-1,2,4-oxadiazole, (S)-5-(4-(3 -(3,5 -difluoro-4-(5-methyl-4,5-dihydrooxazol-2-yl)phenoxy)propyl)piperidin -1-yl)-3-isopropyl-1,2,4-oxadiazole, 5-(4-(3-(4-(5,5-dimethyl-4,5-dihydrooxazol-2-yl)-3,5-difluorophenoxy)propyl)piperidin -1-yl)-3-isopropyl-1,2,4-oxadiazole, 3-(4-(3 -(1-(5 -ethylpyrimidin-2-yl)piperidin-4-yl)propoxy)-2,6-difluorophenyl)-5-methyl -1,2,4-oxadiazole, 3-(4-(3-(1-(5-ethylpyrimidin-2-yl)piperidin-4-yl)propoxy)-2,6-difluorophenyl)-5-propyl -1,2,4-oxadiazole, 3-(4-(3-(1-(5-ethylpyrimidin-2-yl)piperidin-4-yl)propoxy)-2,6-difluorophenyl)-5-isopropyl -1,2,4-oxadiazole, 5-(tert-butyl)-3-(4-(3-(1-(5-ethylpyrimidin-2-yl)piperidin-4-yl)propoxy)-2,6-difluorophenyl) -1,2,4-oxadiazole, (3-(4-(3 -(1-(5-ethylpyrimidin-2-yl)piperidin-4-yl)propoxy)-2,6-difluorophenyl)-1,2,4-oxadiazol-5-yl)methanol, 2-(3-(4-(3-(1-(5-ethylpyrimidin-2-yl)piperidin-4-yl)propoxy)-2,6-difluorophenyl)-1,2,4-oxadiazol-5-yl)ethan-1-ol, (S)-1-(3-(4-(3-(1-(5-ethylpyrimidin-2-yl)piperidin-4-yl)propoxy)-2,6-difluorophenyl) -1,2,4-oxadiazol-5-yl)propan-1-ol, (R)-1-(3-(4-(3-(1-(5-ethylpyrimidin-2-yl)piperidin-4-yl)propoxy)-2,6-difluorophenyl) -1,2,4-oxadiazol-5-yl)propan-2-ol, (S)-1-(3-(4-(3-(1-(5-ethylpyrimidin-2-yl)piperidin-4-yl)propoxy)-2,6-difluorophenyl) -1,2,4-oxadiazol-5-yl)propan-2-ol, 2-(3-(4-(3-(1-(5-ethylpyrimidin-2-yl)piperidin-4-yl)propoxy)-2,6-difluorophenyl)-1,2,4-oxadiazol-5-yl)-2-methylpropan-1-ol, 3-(2,6-difluoro-4-(3-(1-(5-propylpyrimidin-2-yl)piperidin-4-yl)propoxy)phenyl)-5-isopropyl -1,2,4-oxadiazole, 3-(2,6-difluoro-4-(3-(1-(5-pentylpyrimidin-2-yl)piperidin-4-yl)propoxy)phenyl)-5-isopropyl -1,2,4-oxadiazole, 3-(2,6-difluoro-4-(3-(1-(5-(trifluoromethyl)pyrimidin-2-yl)piperidin-4-yl)propoxy)phenyl) -5-isopropyl-1,2,4-oxadiazole, 3-(2,6-difluoro-4-(3-(1-(5-methoxypyrimidin-2-yl)piperidin-4-yl)propoxy)phenyl)-5-isopropyl -1,2,4-oxadiazole, 3-(2,6-difluoro-4-(3-(1-(5-isopropoxypyrimidin-2-yl)piperidin-4-yl)propoxy)phenyl) -5-isopropyl-1,2,4-oxadiazole, 3-(4-(3-(1-(5-chloropyrimidin-2-yl)piperidin-4-yl)propoxy)-2,6-difluorophenyl)-5-isopropyl -1,2,4-oxadiazole, 3-(4-(3-(1-(5-bromopyrimidin-2-yl)piperidin-4-yl)propoxy)-2,6-difluorophenyl)-5-isopropyl -1,2,4-oxadiazole, 3-(2,6-difluoro-4-(3-(1-(5-(5-isobutyl-1,2,4-oxadiazol-3-yl)pyrimidin-2-yl)piperidin -4-yl)propoxy)phenyl)-5-methyl-1,2,4-oxadiazole, 3-(2,6-difluoro-4-(3-(1-(5-(5-isobutyl-1,2,4-oxadiazol-3-yl)pyrimidin-2-yl)piperidin -4-yl)propoxy)phenyl)-5-ethyl-1,2,4-oxadiazole, 3-(2,6-difluoro-4-(3-(1-(5-(5-isobutyl-1,2,4-oxadiazol-3-yl)pyrimidin-2-yl)piperidin -4-yl)propoxy)phenyl)-5-isopropyl-1,2,4-oxadiazole, 5-(sec-butyl)-3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazole, 3-(2,6-difluoro-4-(3-(1-(5-(5-isobutyl-1,2,4-oxadiazol-3-yl)pyrimidin-2-yl)piperidin -4-yl)propoxy)phenyl)-5-(methoxymethyl)-1,2,4-oxadiazole, (S)-1-(3-(2,6-difluoro-4-(3-(1-(5-(5-isobutyl-1,2,4-oxadiazol-3-yl)pyrimidin-2-yl)piperidin -4-yl)propoxy)phenyl)-1,2,4-oxadiazol-5-yl)propan-1-ol, 2-(3-(2,6-difluoro-4-(3-(1-(5-(5-isobutyl-1,2,4-oxadiazol-3-yl)pyrimidin-2-yl)piperidin -4-yl)propoxy)phenyl)-1,2,4-oxadiazol-5-yl)-2-methylpropan-1-ol, 3-(4-(3-(1-(5-chloropyrazin-2-yl)piperidin-4-yl)propoxy)-2,6-difluorophenyl)-5-isopropyl -1,2,4-oxadiazole, 3-(2,6-difluoro-4-(3-(1-(5-(trifluoromethyl)pyridin-2-yl)piperidin-4-yl)propoxy)phenyl -5-isopropyl-1,2,4-oxadiazole, 3-(2,6-difluoro-4-(3-(1-(3-isopropyl-1,2,4-oxadiazol-5-yl)piperidin-4-yl)propoxy)phenyl) -5-methyl-1,2,4-oxadiazole, 3-(2,6-difluoro-4-(3-(1-(3-isopropyl-1,2,4-oxadiazol-5-yl)piperidin-4-yl)propoxy)phenyl) -5-isopropyl-1,2,4-oxadiazole, (3-(2,6-difluoro-4-(3-(1-(3-isopropyl-1,2,4-oxadiazol-5-yl)piperidin-4-yl)propoxy)phenyl) -1,2,4-oxadiazol-5-yl)methanol, 2-(4-(3-(1-(5-ethylpyrimidin-2-yl)piperidin-4-yl)propoxy)-2,6-difluorophenyl)-5-methyl -1,3,4-oxadiazole, 2-ethyl-5-(4-(3-(1-(5-ethylpyrimidin-2-yl)piperidin-4-yl)propoxy)-2,6-difluorophenyl) -1,3,4-oxadiazole, 2-(4-(3-(1-(5-ethylpyrimidin-2-yl)piperidin-4-yl)propoxy)-2,6-difluorophenyl)-5-isopropyl -1,3,4-oxadiazole, 5-(4-(3-(1-(5-ethylpyrimidin-2-yl)piperidin-4-yl)propoxy)-2,6-difluorophenyl)-N-isopropyl -1,3,4-oxadiazol-2-amine, 2-(2,6-difluoro-4-(3-(1-(5-(trifluoromethyl)pyrimidin-2-yl)piperidin-4-yl)propoxy)phenyl) -5-methyl-1,3,4-oxadiazole, 2-(2,6-difluoro-4-(3-(1-(5-(trifluoromethyl)pyrimidin-2-yl)piperidin-4-yl)propoxy)phenyl) -5-ethyl-1,3,4-oxadiazole, 2-(2,6-difluoro-4-(3-(1-(5-(trifluoromethyl)pyrimidin-2-yl)piperidin-4-yl)propoxy)phenyl) -5-isopropyl-1,3,4-oxadiazole, 2-(4-(3-(1-(5-chloropyrazin-2-yl)piperidin-4-yl)propoxy)-2,6-difluorophenyl)-5-methyl -1,3,4-oxadiazole, 2-(4-(3-(1-(5-chloropyrazin-2-yl)piperidin-4-yl)propoxy)-2,6-difluorophenyl)-5-ethyl -1,3,4-oxadiazole, 2-(4-(3-(1-(5-chloropyrazin-2-yl)piperidin-4-yl)propoxy)-2,6-difluorophenyl)-5-isopropyl -1,3,4-oxadiazole, 5-(4-(3-(3,5-difluoro-4-(5-methyl-1,3,4-oxadiazol-2-yl)phenoxy)propyl)piperidin-1-yl) -3-propyl-1,2,4-oxadiazole, 5-(4-(3-(3,5-difluoro-4-(5-ethyl-1,3,4-oxadiazol-2-yl)phenoxy)propyl)piperidin-1-yl) -3-propyl-1,2,4-oxadiazole, 5-(4-(3-(3,5-difluoro-4-(5-isopropyl-1,3,4-oxadiazol-2-yl)phenoxy)propyl)piperidin-1-yl)-3-propyl-1,2,4-oxadiazole, 5-(4-(3-(3,5-difluoro-4-(5-methyl-1,3,4-oxadiazol-2-yl)phenoxy)propyl)piperidin-1-yl -3-isopropyl-1,2,4-oxadiazole, 5-(4-(3-(4-(5-ethyl-1,3,4-oxadiazol-2-yl)-3,5-difluorophenoxy)propyl)piperidin-1-yl) -3-isopropyl-1,2,4-oxadiazole, 5-(4-(3-(3,5-difluoro-4-(5-isopropyl-1,3,4-oxadiazol-2-yl)phenoxy)propyl)piperidin-1-yl)-3-isopropyl-1,2,4-oxadiazole, 5-(4-(3-(3,5-difluoro-4-(5-methyl-1,3,4-oxadiazol-2-yl)phenoxy)propyl)piperidin-1-yl) -3-(2,2,2-trifluoroethyl)-1,2,4-oxadiazole, 3-(4-(3-(3,5-difluoro-4-(5-isopropyl-1,3,4-oxadiazol-2-yl)phenoxy)propyl)piperidin-1-yl)-5-isopropyl-1,2,4-oxadiazole, 2-(4-(3-(1-(5-ethylpyrimidin-2-yl)piperidin-4-yl)propoxy)-2,6-difluorophenyl)-5-isopropyl -1,3,4-thiadiazole, 2-(2,6-difluoro-4-(3-(1-(5-propylpyrimidin-2-yl)piperidin-4-yl)propoxy)phenyl)-5-isopropyl -1,3,4-thiadiazole, 2-(2,6-difluoro-4-(3-(1-(5-pentylpyrimidin-2-yl)piperidin-4-yl)propoxy)phenyl)-5-isopropyl -1,3,4-thiadiazole, 2-(2,6-difluoro-4-(3-(1-(5-fluoropyrimidin-2-yl)piperidin-4-yl)propoxy)phenyl)-5-isopropyl -1,3,4-thiadiazole, 2-(2,6-difluoro-4-(3-(1-(5-(trifluoromethyl)pyrimidin-2-yl)piperidin-4-yl)propoxy)phenyl) -5-isopropyl-1,3,4-thiadiazole, 2-(2,6-difluoro-4-(3-(1-(5-(trifluoromethyl)pyridin-2-yl)piperidin-4-yl)propoxy)phenyl) -5-isopropyl-1,3,4-thiadiazole and 4-ethyl-2-(4-(3-(1-(5-ethylpyrimidin-2-yl)piperidin-4-yl)propoxy)-2,6-difluorophenyl) thiazole.

Meanwhile, the compound represented by the Chemical Formula 1 may have an asymmetric carbon center, and if having the asymmetric carbon center, may exist as an optical isomer, a diastereomer or a recemate, and all forms of isomers including these may be also within the scope of the compound according to one embodiment of the present invention.

Further, a pharmaceutically acceptable salt of the compound represented by the Chemical Formula 1, or a pharmaceutically acceptable salt of the isomers of the compound represented by the Chemical Formula 1 may be also within the scope of the compound of the above described one embodiment. For example, non-limiting examples of the pharmaceutically acceptable salt of the compound represented by the Chemical Formula 1 or the isomer thereof may include a salt with an inorganic acid such as hydrochloric acid, hydrobromic acid, phosphoric acid or sulfuric acid; a salt with an organic carboxylic acid such as acetic acid, trifluoroacetic acid, citric acid, maleic acid, oxalic acid, succinic acid, benzoic acid, tartaric acid, fumaric acid, mandelic acid, ascorbic acid or malic acid, or a salt with a sulfonic acid such as methane sulfonic acid or p-toluene sulfonic acid; a salt with an alkali metal such as sodium, potassium or lithium; a salt with various acids known to be capable of forming other pharmaceutically acceptable salts, or the like.

The compound within the scope of the compound of the above Chemical Formula 1 may represent an excellent GPR119 agonistic activity, and accordingly represent a hypoglycemic action and a positive effect on pancreatic beta cells, thereby being more effectively used to treat various metabolic diseases.

As described above, the present inventors newly synthesized the compound of the Chemical Formula 1 having a GPR119 agonistic activity, and a pharmaceutical composition including the compound having a G protein-coupled receptor (GPR119) agonistic activity may have an effective hypoglycemic action and a positive effect on pancreatic beta cells, and also represent an effect of improving lipid metabolism which is a chronic cardiovascular risk factor, thereby being effective in the treatment and/or prevention of a metabolic disease.

The agonistic activity to GPR119 may increase secretion of glucagon-like peptide (GLP-1) or stability of secreted GLP-1 to represent anti-obesity and anti-diabetic efficacy mediated by the action of endogenous incretin.

Accordingly, another embodiment of the present invention provides a pharmaceutical composition including the above compound, the isomer thereof or the pharmaceutically acceptable salt thereof as an effective component. More preferably, the pharmaceutical composition may be for treatment or prevention of a metabolic disease. More preferably, the metabolic disease may be selected from the group consisting of diabetes, obesity, hypertension, a cardiovascular disease, a hemostatic disorder and dyslipidemia.

A pharmaceutical composition including the compound represented by the Chemical Formula 1, the isomer thereof or the pharmaceutically used salt thereof, as an effective component may be used in the form of a general medicinal preparation. The medicinal preparation may be administered in various formulations such as oral and parenteral formulation, and the formulation may be variously determined depending on usage.

If the composition is formulated into various oral and parenteral formulations, it may be prepared using a generally used excipient such as a filler, a diluent, a bulking agent, a binder, a wetting agent, a disintergrating agent, a surfactant.

A solid preparation for oral administration may include tablets, pills, powders, granules, capsules, and the like, and the solid preparation may be prepared by mixing the compound represented by the Chemical Formula 1, the isomer thereof, or the pharmaceutically acceptable salt thereof with at least one excipient, for example, starch, calcium carbonate, sucrose or lactose, gelatin, and the like. Further, in addition to a simple excipient, a lubricant such as magnesium stearate and talc may be used.

Further, a liquid preparation for oral administration may be suspensions, oral liquids, emulsions, syrups, and the like, and include various excipients, for example, a wetting agent, a sweetener, an aromatic, a preservative, and the like, in addition to water and liquid paraffin which are a simple diluent to be commonly used.

The preparation for parenteral administration includes a sterile aqueous solution, a non-aqueous solvent, a suspension, an emulsion, a freeze-dried preparation, a suppository and the like. As the non-aqueous solvent and the suspension solvent, propylene glycol, polyethylene glycol, a vegetable oil such as an olive oil, injectable ester such as ethyl oleate, and the like may be used. As a base of the suppository, witepsol, microgol, tween 61, cacao butter, laurin butter, glycerogelatin, and the like may be used.

Further, the pharmaceutical composition of the present invention including the compound represented by the Chemical Formula 1, the isomer thereof or a pharmaceutically acceptable salt thereof as an effective component may have an effective amount in a dosage range of about 0.1 to about 1,000 mg. A dosage or dose may be administered in various dosages and methods, for example, in divided dosages from once to several times a day depending on a patient's weight, age, sex, a health condition, diet, administration time, an administration method, an excretion rate, and severity of a disease.

Meanwhile, yet another embodiment of the present invention provides a method for preparing the compound of Chemical Formula 1 of the above described one embodiment, including introducing a B group to a nitrogen group of piperidine of a compound of following Chemical Formula 2 to prepare a compound of following Chemical Formula 4; and introducing a compound of following Chemical Formula 12 to a hydroxyl group of the compound of the Chemical Formula 4:

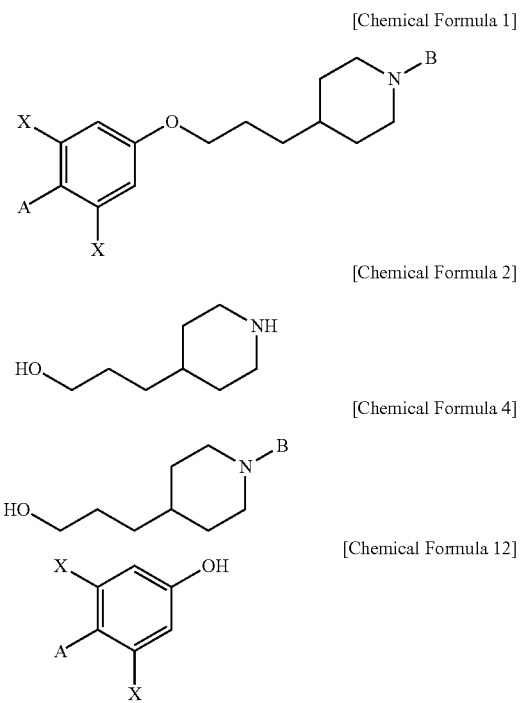

wherein

A is oxadiazole, dihydrooxazole, thiazole or thiadiazole, optionally substituted by one or more substituents selected from the group consisting of hydrogen, halogen, C1-C6 straight chain or branched chain alkyl and C1-C6 alcohol, the alkyl or alcohol group being optionally substituted by hydrogen, halogen or a C1-C6 alkoxy group;

B is pyridine, pyrimidine, pyrazine or oxadiazole, optionally substituted by one or more substituents selected from the group consisting of hydrogen, halogen, C1-C6 straight chain or branched chain alkyl, C1-C6 alcohol, C1-C6 alkoxy and an oxadiazole group, the alkyl, alcohol, alkoxy or oxadiazole group being optionally substituted by hydrogen, halogen or a C1-C6 alkyl or C1-C6 alkoxy group; and X is independently F, Cl, Br or I.

In the method for preparing the compound of the Chemical Formula 1, a reaction order of the step to introduce a B group to a nitrogen group of piperidine of a compound of the Chemical Formula 2, and the step to introduce the compound of the Chemical Formula 12 to a hydroxyl group of the compound of the Chemical Formula 4 is not limited, and thus, the compound of the Chemical Formula 12 may be introduced first to the hydroxyl group of the compound of the Chemical Formula 2, and the B group may be introduced first to the nitrogen group of piperidine.

Preferably, the step to introduce the compound of the Chemical Formula 12 to the hydroxyl group of the compound of the Chemical Formula 4 may include reacting the compound of the Chemical Formula 4 and a compound of following Chemical Formula 12a; and converting A' into A:

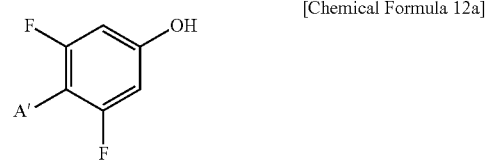

wherein

A' is a cyano group, a carboxyl group, an ester group, a ketone group or halogen.

More preferably, the step to react the compound of the Chemical Formula 4 and the compound of the Chemical Formula 12a may include introducing a methane sulfonyl group to the hydroxyl group of the Chemical Formula 4; and reacting the compound of the Chemical Formula 4 to which the methane sulfonyl group is introduced with the compound of the Chemical Formula 12a.

The step to introduce a methane sulfonyl group to the hydroxyl group of the Chemical Formula 4 may include reacting the compound of the Chemical Formula 4 with a compound selected from the group consisting of methane sulfonyl chloride, p-toluene sulfonyl chloride and trichloromethane sulfonyl chloride.

When the compound of the Chemical Formula 4 is reacted with methane sulfonyl chloride, p-toluene sulfonyl chloride or trichloromethane sulfonyl chloride, a methane sulfonyl group may be introduced to the hydroxyl group of the Chemical Formula 4, and more preferably, methane sulfonyl chloride may be used. Conditions in the above reaction such as reaction temperature and reaction time may be appropriately controlled depending on an amount of the reactants, ambient conditions, and the like, however, the methane sulfonyl group may be more efficiently introduced by for example, a reaction at a temperature of −10 to 10° C., or at about 0° C. for 10 minutes to 3 hours under a solvent of dichlororomethane (MC).

Next, the compound of the Chemical Formula 4 to which the methane sulfonyl group is introduced may be reacted with the compound of the Chemical Formula 12a.

Specifically, the compound of the Chemical Formula 4 in which the methane sulfonyl group is introduced to the hydroxyl group in the previous step may be subjected to a coupling reaction with the hydroxyl group of the compound of the Chemical Formula 12a, thereby carrying out a reaction with the compound of the Chemical Formula 12a.

The coupling reaction may be carried out in the presence of one or more bases selected from the group consisting of sodium carbonate, calcium carbonate, potassium carbonate and cesium carbonate; and one or more solvents selected from the group consisting of methyl sulfoxide, dimethyl formamide, N-methylpyrrolidin-2-on, tetrahydrofuran and 1,4-dioxane. As the base, potassium carbonate may be preferably used, and as the solvent, dimethyl formamide may be preferably used. Conditions such as the reaction temperature and the reaction time of the coupling reaction may be appropriately controlled depending on an amount of the reactants, ambient conditions, and the like, however, for example, may be carried out at a temperature range of 50° C. to 100° C. for 5 to 24 hours.

Next, A' of the Chemical Formula 12a may be converted into A. The conversion step may be carried out using an appropriate process depending on the kind of A, and more specifically, using the following process.

The compound wherein A is

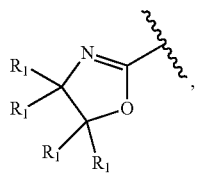

may be prepared by a method comprising:
oxidizing the compound of the Chemical Formula 12a wherein A' is a carboxyl group or an ester group to prepare carboxylic acid; reacting the carboxylic acid with aminoethanol of following Chemical Formula 13 to introduce a compound of following Chemical Formula 14 to A' of the Chemical Formula 12a; and cyclizing the compound prepared in the previous step.

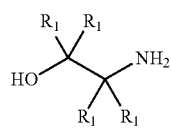

[Chemical Formula 13]

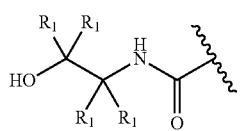

[Chemical Formula 14]

wherein $R_1$ is as defined in the Chemical Formula 1.

The oxidation step may be carried in methyl alcohol, ethyl alcohol, tetrahydrofuran, 1,4-dioxane or the like as a solvent, by using an aqueous sodium hydroxide solution, an aqueous potassium hydroxide solution or the like, and the reaction may be carried out at 0° C. to 80° C. for 1 to 5 hours. Thereafter, acidification with an aqueous HCl solution is carried out.

Further, the reaction with the aminoethanol may be carried out in methyl alcohol, ethyl alcohol, tetrahydrofuran, 1,4-dioxane or the like as a solvent, by adding 1-ethyl-3-(3-dimethylaminopropyl)carbodiimide hydrochloride (EDC.HCl) and hydroxybenzotriazole to perform a reaction at 10 to 40° C. for 5 minutes to 3 hours, and then adding triethylamine and aminoethanol to perform a reaction at 10 to 40° C. for 1 to 10 hours.

Thereafter, the cyclization step may be carried out by reacting triphenylphosphine and 2,3-dichloro-5,6-dicyano-1,4-benzoquinone at 10 to 40° C. for 0 minute to 3 hours under a dichloromethane (MC) solvent.

Further, the compound wherein A is

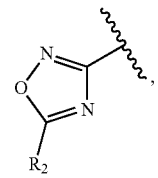

may be prepared by a method comprising:
reacting the compound of the Chemical Formula 12a wherein A' is a cyano group with hydroxylamine to introduce a compound of following Chemical Formula 15 to A' of the Chemical Formula 12a; and reacting a compound prepared in the previous step and a compound of following Chemical Formula 16.

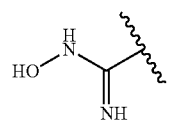

[Chemical Formula 15]

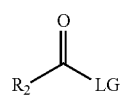

[Chemical Formula 16]

wherein $R_2$ is identical to $R_2$ of the Chemical Formula 1; and LG is a leaving group.

The reaction with hydroxylamine may be carried out in methyl alcohol, ethyl alcohol, tetrahydrofuran or 1,4-dioxane as a solvent, at 80 to 150° C. for 1 to 10 hours.

Further, the reaction with the compound of the Chemical Formula 16 may be carried out by performing a first reaction at 10 to 40° C. for 10 minutes to 3 hours under a dichloromethane (MC) solvent together with triethylamine, and then a second reaction at 100 to 200° C. for 1 to 10 hours. LG of Chemical Formula 16 is a functional group to depart during the reaction, and may be more specifically halogen, and still more specifically Cl, but not limited thereto.

Further, the compound wherein A is

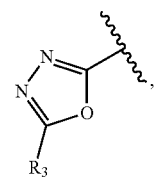

may be prepared by a method comprising:
oxidizing the compound of the Chemical Formula 12a wherein A' is a carboxyl group or an ester group to prepare carboxylic acid; reacting the carboxylic acid with hydrazine to introduce a compound of following Chemical Formula 17 to A' of the Chemical Formula 12a; and reacting a compound prepared in the previous step with a compound of following Chemical Formula 18 or 19.

[Chemical Formula 17]

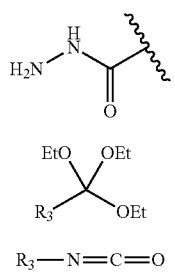

[Chemical Formula 18]

EtO  OEt
  \\ /
   C
  / \\
 R₃   OEt

[Chemical Formula 19]

R₃—N=C=O wherein R₃ is as defined in the Chemical Formula 1.

The oxidation step may be carried in methyl alcohol, ethyl alcohol, tetrahydrofuran, 1,4-dioxane or the like as a solvent, by using an aqueous sodium hydroxide solution, an aqueous potassium hydroxide solution or the like, and the reaction may be carried out at 0° C. to 80° C. for 1 to 5 hours. Thereafter, acidification with an aqueous HCl solution is carried out.

The reaction with the hydrazine may be carried out in dichloromethane (MC) as a solvent, by adding 1-ethyl-3-(3-dimethylaminopropyl)carbodiimide hydrochloride (EDC.HCl) and hydroxybenzotriazole to perform a reaction at 10 to 40° C. for 5 minutes to 3 hours, and then adding hydrazine to perform a reaction at 10 to 40° C. for 1 to 10 hours.

Further, the reaction step with the compound of the Chemical Formula 18 may be carried out by adding a reactant obtained from the previous step to the solution of the Chemical Formula 18 to perform a reaction at 100 to 200° C. for 1 to 10 hours, and the reaction step with the compound of the Chemical Formula 19 may be carried out by dissolving the compound of the Chemical Formula 17 obtained in the previous step in an aqueous solution, and then adding triethylamine and the compound of the Chemical Formula 19 to perform a reaction at 100 to 200° C. for 1 to 12 hours.

Further, the compound wherein A is

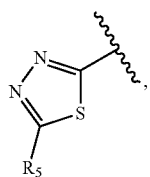

may be prepared by a method comprising:
oxidizing the compound of the Chemical Formula 12a wherein A' is a carboxyl group or an ester group to prepare carboxylic acid; reacting the carboxylic acid with hydrazide to introduce a compound of following Chemical Formula 20 to A' of the Chemical Formula 12a; and reacting the compound prepared in the previous step with a compound of following Chemical Formula 21 (Lawessen's reagent).

[Chemical Formula 20]

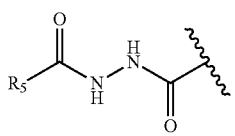

[Chemical Formula 21]

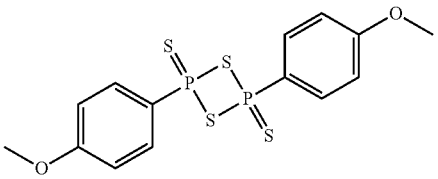

wherein R₅ is as defined in the Chemical Formula 1.

The oxidation step may be carried in methyl alcohol, ethyl alcohol, tetrahydrofuran, 1,4-dioxane or the like as a solvent, by using an aqueous sodium hydroxide solution, an aqueous potassium hydroxide solution or the like, and the reaction may be carried out at 0° C. to 80° C. for 1 to 5 hours. Thereafter, acidification with an aqueous HCl solution is carried out.

The reaction step with the hydrazide may be carried out in dichloromethane (MC) as a solvent, by adding 1-ethyl-3-(3-dimethylaminopropyl)carbodiimide hydrochloride (EDC.HCl) and hydroxybenzotriazole to perform a reaction at 10 to 40° C. for 5 minutes to 3 hours, and then adding hydrazide to perform a reaction at 10 to 40° C. for 1 to 18 hours.

Further, the reaction step with the compound of the Chemical Formula 21 may be carried out by dissolving the compound of the Chemical Formula 20 obtained in the previous step in xylene, and then adding the compound of the Chemical Formula 21 to perform a reaction at 100 to 200° C. for 10 minutes to 2 hours.

Further, the compound wherein A is

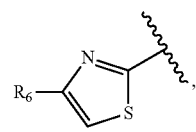

may be prepared by a method comprising:
oxidizing the compound of the Chemical Formula 12a wherein A' is a carboxyl group or an ester group to prepare carboxylic acid; reacting the carboxylic acid and thionyl chloride to introduce a structure of following Chemical Formula 22 to A' of the Chemical Formula 12a; converting the structure of the Chemical Formula 22 into amide structure of following Chemical Formula 23; reacting the obtained compound with the compound of the Chemical Formula 21 (Lawessen's reagent) to be converted into a compound having thioamide structure of following Chemical Formula 24; and reacting the obtained compound with a compound of following Chemical Formula 25.

[Chemical Formula 22]

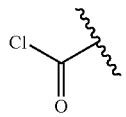

[Chemical Formula 23]

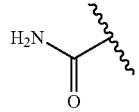

[Chemical Formula 24]

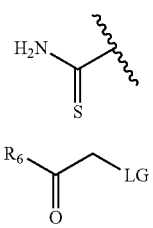

[Chemical Formula 25]

$R_6$ ~~ LG (with =O)

wherein $R_6$ is identical to $R_6$ of the Chemical Formula 1; and LG is a leaving group.

The oxidation step may be carried in methyl alcohol, ethyl alcohol, tetrahydrofuran, 1,4-dioxane or the like as a solvent, by using an aqueous sodium hydroxide solution, an aqueous potassium hydroxide solution or the like, and the reaction may be carried out at 0° C. to 80° C. for 1 to 5 hours. Thereafter, acidification with an aqueous HCl solution is carried out.

The step to introduce the compound of the Chemical Formula 22 may be carried out by adding thionyl chloride under a dichloromethane solvent at 0° C. to 80° C. for 1 to 5 hours The step to introduce the compound of the Chemical Formula 23 may be carried out at 10 to 40° C. for 1 to 3 hours by dissolving the compound of the Chemical Formula 21 obtained in the previous step in benzene, and then adding sodium hydroxide and ammonium chloride.

The step to introduce the compound of the Chemical Formula 24 may be carried out by dissolving the compound of the Chemical Formula 23 obtained in the previous step in tetrahydrofuran, and then adding the compound of the Chemical Formula 21 thereto, to perform a reaction at 10 to 60° C. for 1 to 3 hours.

Further, the reaction step with the compound of the Chemical Formula 25 may be carried out by dissolving the compound of the Chemical Formula 24 obtained in the previous step in ethanol, and then adding the compound of the Chemical Formula 25 thereto, to perform a reaction at 70 to 100° C. for 1 to 6 hours.

Besides, A' may be converted into various A groups through conventional processes in the art, which are shown specifically in the following Examples.

Further, the step to introduce the B group to the nitrogen group of piperidine of the compound of the Chemical Formula 2 may be carried out by reacting the nitrogen group of piperidine with a suitable intermediate compound such as halogen-substituted pyrimidine, halogen-substituted pyridine, or a cyano group, and synthesizing the desired B group through a conventional process in the art. The specific processes thereof will be described in the following Examples.

The novel compound, the isomer thereof, or the pharmaceutically acceptable salt thereof of the present invention represents a GPR119 agonistic activity, and thus, may be used in the treatment and/or prevention of a metabolic disease such as diabetes usefully. More specifically, through the GPR119 agonistic activity, effective hypoglycemic action and a positive effect on pancreatic beta cells may be generated, and also lipid metabolism which is a chronic cardiovascular risk factor may be improved.

Examples

Hereinafter, the present invention will be described in detail by the following Examples, in order to give an understanding of the invention. However, those Examples are only for illustrating the present invention, and do not limit the scope of the present invention thereto. The Examples of the present invention are provided in order to more completely explain the present invention to a person skilled in the art.

According to one exemplary embodiment, an example of the method for preparing the compound of the Chemical Formula 1, including introducing the B group to the nitrogen group of piperidine of the compound of the Chemical Formula 2 to prepare the compound of the Chemical Formula 4, and introducing the compound of the Chemical Formula 12 to the hydroxyl group of the compound of the Chemical Formula 4, is as summarized in following Reaction Formulae 1 to 3.

However, those Reaction Formulae 1 to 3 represent only a summarized example of a method for preparing the compound of the present invention, and the methods for preparation of other embodiments are not limited thereto.

[Reaction Formula 1]

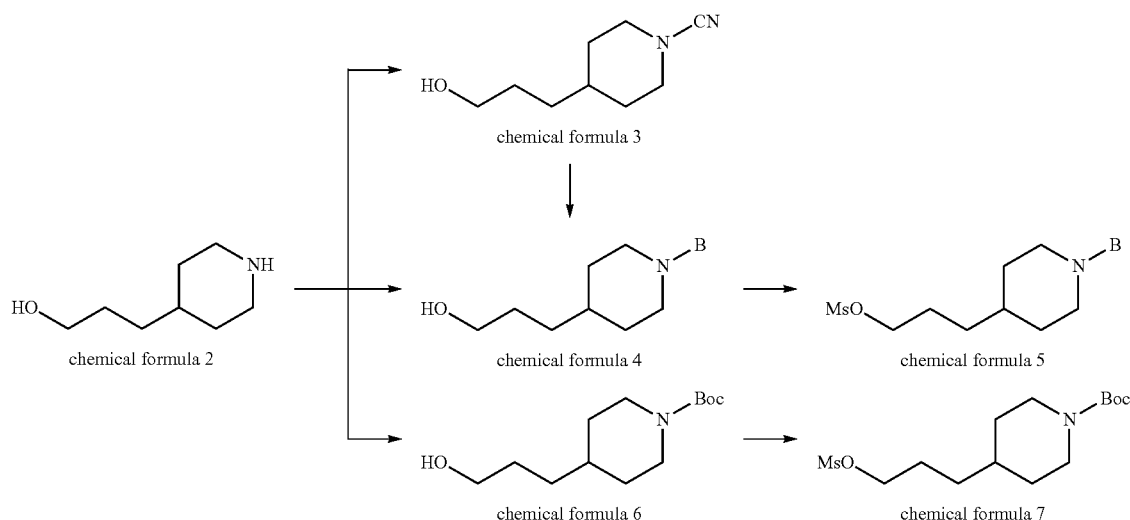

[Reaction Formula 2]
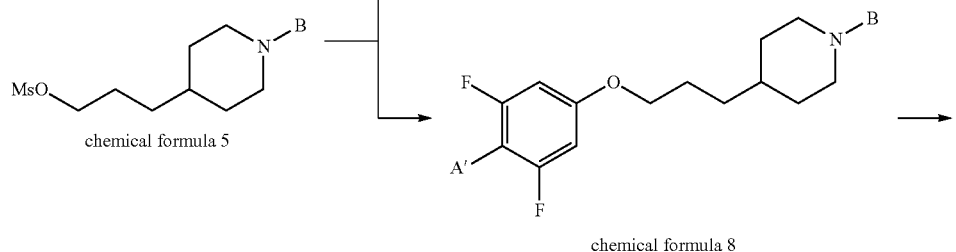
chemical formula 5
chemical formula 8
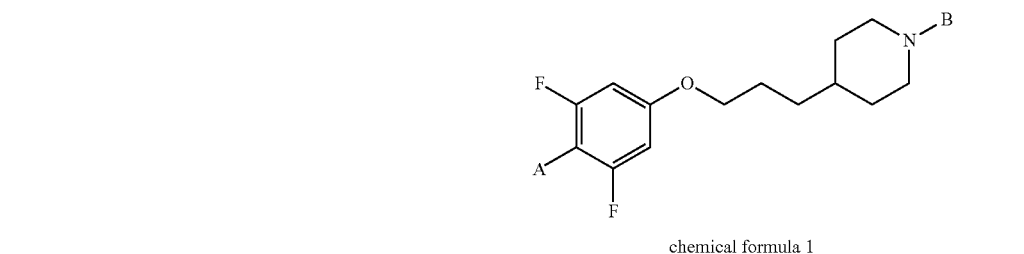
chemical formula 1
[Reaction Formula 3]
chemical formula 7
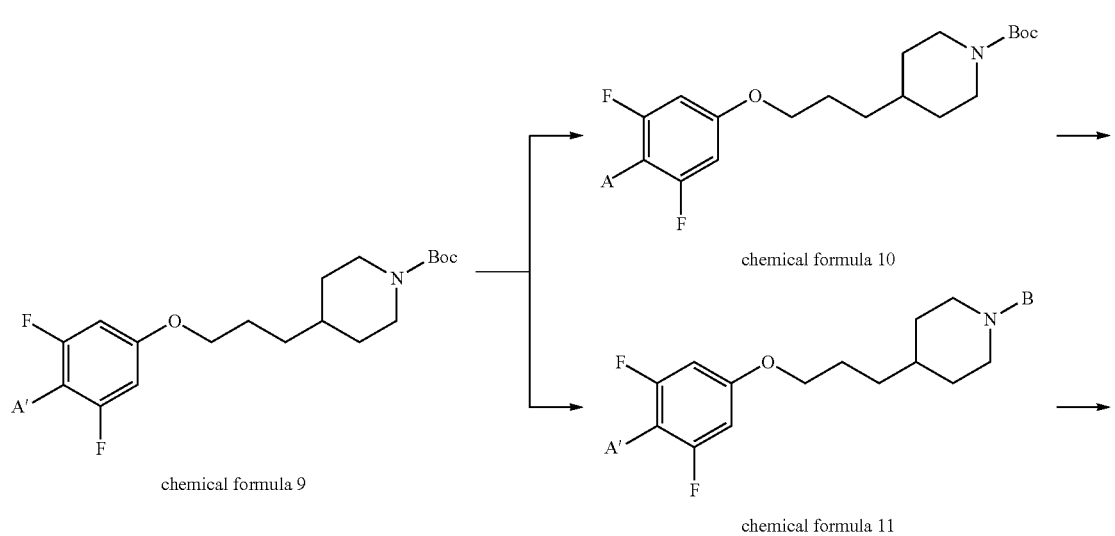
chemical formula 9
chemical formula 10
chemical formula 11
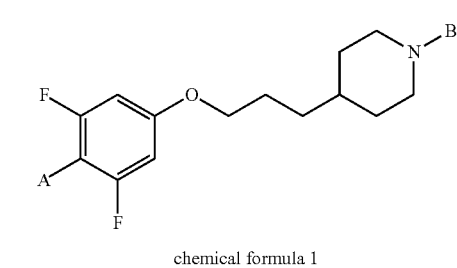
chemical formula 1

The compounds synthesized in the following Preparation Examples were identified by nuclear magnetic resonance spectrum, and mass spectrometry.

<Preparation Example 1> Preparation of (R)-5-(4-(3(3,5-difluoro-4-(4-methyl-4,5-dihydrooxazol-2-yl)phenoxy)propyl)piperidine-1-yl) -3-isopropyl-1,2,4-oxadiazole (Step 1-1) Preparation of 4-(3-hydroxypropyl)piperidine-1-carbonitrile (Chemical Formula 3)

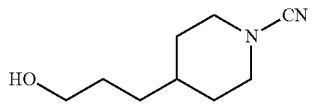 [SMILES: N#CN1CCC(CCCO)CC1]

3-(Piperidin-4-yl)propan-1-ol hydrochloride of the Chemical Formula 2 (10 g, 69.8 mmol) was dissolved in a mixed solution of dichloromethane (MC, 75.0 ml) and water (55.0 ml); sodium bicarbonate (NaHCO₃, 16.36 g, 195.0 mmol) was added thereto; then cyanic bromide (6.48 g, 61.2 mmol) was added thereto; and stirring was carried out at room temperature for 15 hours. An excess amount of an aqueous ammonium chloride solution was added thereto; extraction was carried out with dichloromethane; and then washing was carried out with brine. Moisture was removed from an organic layer with MgSO₄, and the organic layer was filtered and concentrated under reduced pressure, thereby obtaining the desired form of the compound, 4-(3-hydroxypropyl)piperidin-1-carbonitrile in a quantitative yield, which was used in the next reaction without purification.

$[M+1]^+$=169.1 m/z(ESI).

(Step 1-2) Preparation of N-hydroxyisobutylimidamide

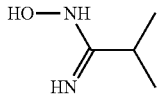

Isobutyronitrile (Chemical Formula 15, 6.22 g, 90 mmol) was dissolved in ethanol (125 ml), and a 50% aqueous hydroxyamine solution (18 ml) and sodium hydroxide (5.4 g, 135 mmol) were added thereto. The reaction solution was heated to be stirred under a reflux condition for 2 hours, and then concentrated under reduced pressure, diluted with water, and extracted with EA. Moisture was removed from an organic layer with MgSO₄, and the organic layer was filtered and concentrated under reduced pressure, thereby obtaining the desired form of the compound, N-hydroxyisobutylimidamide in a quantitative yield, which was used in the next reaction without purification.

$[M+1]^+$=103.1 m/z(ESI).

(Step 1-3) Preparation of 3-(1-(3-isopropyl-1,2,4-oxadiazol-5-yl)piperidin-4-yl)propan-1-ol

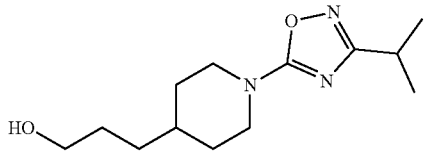 [SMILES: CC(C)c1noc(N2CCC(CCCO)CC2)n1]

4-(3-Hydroxypropyl)piperidin-1-carbonitrile of the Chemical formula 3 synthesized in the above step 1-1 (11.67 g, 69.4 mmol), and N-hydroxyisobutylimidamide synthesized in the above step 1-2 (8.5 g, 83.0 mmol) were dissolved in diethylether (150 ml), and then a 1M zinc chloride diethyl ether solution (90 ml, 90 mmol) was added thereto, and stirred at room temperature for 40 minutes. The stirred reaction solution was heated at 100° C. to evaporate 100 ml or more of diethyl ether, and then ethanol (200 ml) was added thereto. Thereafter, concentrated hydrochloric acid (4.21 ml, 139 mmol) was dropped thereto, stirring was carried out at 100° C. for 15 hours. The reaction solution was concentrated under reduced pressure, diluted with water, and extracted with EA. Moisture was removed from an organic layer with MgSO₄, and the organic layer was filtered and concentrated under reduced pressure. The residue was purified with silica gel column chromatography to obtain the desired form of the compound, 3-(1-(3-isopropyl-1,2,4-oxadiazol-5-yl)piperidin-4-yl)propan-1-ol (14.3 g, 56.4 mmol) in a yield of 81%.

¹H NMR(400 MHz, CDCl₃) δ4.09(d, 2H, J=12.8 Hz), 3.62(t, 2H, J=6.8Hz), 2.99(t, 2H, J=13.2 Hz), 2.85(m, 1H, J=6.8 Hz), 1.75(d, 2H, J=12.4 Hz), 1.56(m, 2H), 1.46(m, 1H), 1.33(m, 2H), 1.25(d, 6H, J=6.8 Hz), 1.20(m, 2H)); $[M+1]^+$=254.2 m/z(ESI).

(Step 1-4) Preparation of 3-(1-(3-isopropyl-1,2,4-oxadiazol-5-yl)piperidin-4-yl)propyl methane sulfonate

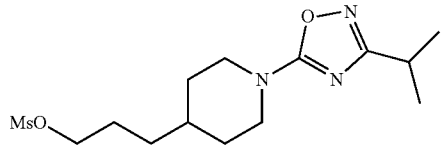 [SMILES: CC(C)c1noc(N2CCC(CCCOS(C)(=O)=O)CC2)n1]

3-(1-(3-Isopropyl-1,2,4-oxadiazol-5-yl)piperidin-4-yl)propan-1-ol synthesized in the above step 1-3 (108.9 g, 0.43 mol) was dissolved in MC, and cooled down to 0° C.

Triethylamine (89.1 ml, 0.64 mol) and methane sulfonyl chloride (39.7 ml, 0.51 mol) were slowly dropped to the reaction solution. The reaction solution was stirred at room temperature for 1 hour, diluted with MC, and washed with water. Moisture was removed from an organic layer with MgSO₄, and the organic layer was filtered and concentrated under reduced pressure, thereby obtaining the desired form of the compound, 3-(1-(3-isopropyl-1,2,4-oxadiazol-5-yl) piperidin-4-yl)propyl methane sulfonate in a quantitative yield.

$[M+1]^+$=332.2 m/z (ESI).

(Step 1-5) Preparation of methyl 2,6-difluoro-4-(3-(1-(3-isopropyl-1,2,4-oxadiazol-5-yl)propoxy)benzoate

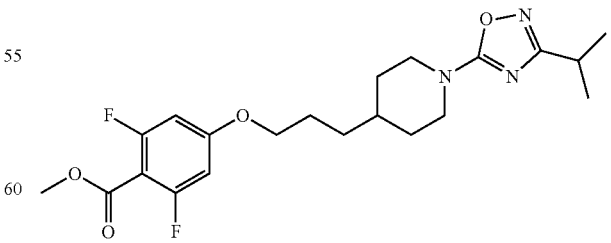

Methyl 2,6-difluoro-4-hydroxybenzoate (111.9 g, 0.59 mol) was dissolved in N,N-dimethyl formamide (DMF, 2 L), and 3-(1-(3-isopropyl-1,2,4-oxadiazol-5-yl)piperidin-4-yl) propyl methane sulfonate synthesized in the above step 1-4

(165.7 g, 0.50 mol) and potassium carbonate (K₂CO₃, 205.6 g, 1.49 mol) were added to the reaction solution. The reaction solution was stirred at 60° C. for 18 hours, and then diluted with water, and extracted with EA. Moisture was removed from an organic layer with MgSO₄, and the organic layer was filtered and concentrated under reduced pressure, thereby obtaining the desired form of the compound, methyl 2,6-difluoro-4-(3-(1-(3-isopropyl-1,2,4-oxadiazol-5-yl)propoxy)benzoate in a yield of 85%.

[M+1]⁺=424.2m/z(ESI).

(Step 1-6) Preparation of 2,6-difluoro-4-(3-(1-(3-isopropyl-1,2,4-oxadiazol-5-yl)piperidin-4-yl)propoxy)benzoic acid

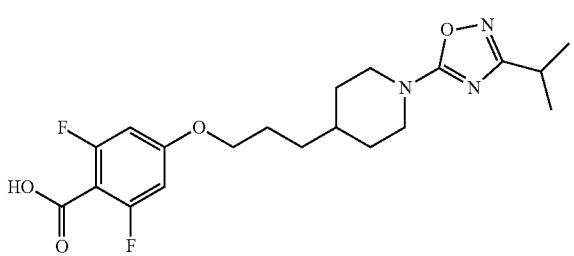 [SMILES: CC(C)c1noc(N2CCC(CCCOc3cc(F)c(C(=O)O)c(F)c3)CC2)n1]

The compound obtained in the above step 1-5, methyl 2,6-difluoro-4-(3-(1-(3-isopropyl-1,2,4-oxadiazol-5-yl)propoxy)benzoate (88.9 g, 0.21 mol) was dissolved in a 1,4-dioxane solvent (1.5 L), and then a 2N aqueous NaOH solution (312 ml, 0.62 mol) was slowly dropped thereto. The reaction solution was stirred at 80° C. for 3 hours, and then diluted with water, and a 2N aqueous HCl solution (800 ml) was added thereto, to acidify the solution. A mixed solution was extracted with EA (1.7 L), and then Moisture was removed from an organic layer with MgSO₄, and the organic layer was filtered and concentrated under reduced pressure, thereby obtaining the desired form of the compound, 2,6-difluoro-4-(3-(1-(3-isopropyl-1,2,4-oxadiazol-5-yl)piperidin-4-yl)propoxy)benzoic acid in a yield of 97%.

[M+1]⁺=410.2m/z(ESI).

(Step 1-7) Preparation of (R)-2,6-difluoro-N-(2-hydroxypropyl)-4-(3-(1-(3-isopropyl-1,2,4-oxadiazol-5-yl)piperidin-4-yl)propoxy)benzamide

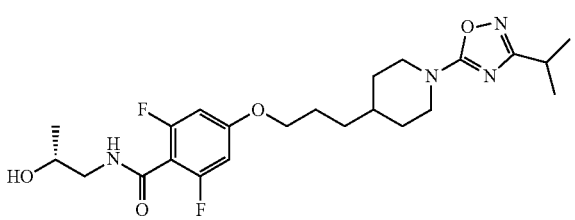 [SMILES: CC(C)c1noc(N2CCC(CCCOc3cc(F)c(C(=O)NC[C@@H](C)O)c(F)c3)CC2)n1]

2,6-difluoro-4-(3-(1-(3-isopropyl-1,2,4-oxadiazol-5-yl)piperidin-4-yl)propoxy)benzoic acid obtained in the above step 1-6 (0.41 g, 0.001 mol) was dissolved in THF, and 1-ethyl-3-(3-dimethylaminopropyl)carbodiimide hydrochloride (EDC.HCl, 0.38 g, 0.002 mol) and hydroxybenzotriazole monohydrate (HOBt..H₂O, 0.27 g, 0.002 mol) were added thereto. After stirring at room temperature for 1 hour, triethylamine (0.42 ml, 0.003 mol) and (R)-1-aminopropan-2-ol (0.38 g, 0.005 mol) were added thereto. After stirring at room temperature for 4 hours, dilution with water and extraction with EA were carried out. Moisture was removed from an organic layer with MgSO₄, and the organic layer was filtered and concentrated under reduced pressure, thereby obtaining the desired form of the compound, (R)-2,6-difluoro-N-(2-hydroxypropyl)-4-(3-(1-(3-isopropyl-1,2,4-oxadiazol-5-yl)piperidin-4-yl)propoxy)benzamide in a yield of 85%.

[M+1]⁺=467.2m/z(ESI).

(Step 1-8) Preparation of (R)-5-(4-(3(3,5-difluoro-4-(4-methyl-4,5-dihydrooxazol-2-yl)phenoxy)propyl)piperidin-1-yl) -3-isopropyl-1,2,4-oxadiazole (Preparation Example 1)

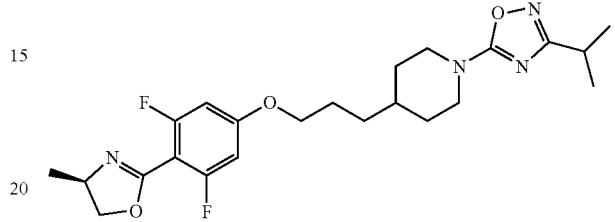

Above 2,6-difluoro-N-(2-hydroxyethyl)-4-(3-(1-(5-(5-isobutyl-1,2,4-oxadiazol-3-yl)pyrimidin-2-yl) piperidin-4-yl)propoxy)benzamide (42.9 mg, 0.092 mmol) was dissolved in MC, and then triphenylphosphine (PPh₃, 36.2 mg, 0.138 mmol) and 2,3-dichloro-5,6-dicyano-1,4-benzoquinone (DDQ, 31.3 mg, 0.138 mmol) were added to the reaction solution. The reaction solution was stirred at room temperature for 1 hour, diluted with EA, and washed with water. The mixed solution was extracted with EA, and then Moisture was removed from an organic layer with MgSO₄, the organic layer was filtered and concentrated under reduced pressure, and the residue was purified by silica gel column chromatography to obtain the desired form of the compound, (R)-5-(4-(3(3,5-difluoro-4-(4-methyl-4,5-dihydrooxazol-2-yl)phenoxy)propyl)piperidin-1-yl) -3-isopropyl-1,2,4-oxadiazole in a yield of 85%.

¹H NMR(600 MHz, CDCl₃) δ6.45(d, 2H, J=9.6 Hz), 4.48(dd, 1H, J=9.0 Hz, 8.4 Hz), 4.37(m, 1H), 4.12(d, 2H, J=12.6 Hz), 3.94(m, 2H), 3.01(td, 2H, J=13.2, 2.4 Hz), 2.86(q, 1H, J=7.2 Hz), 1.79(m, 4H), 1.50(m, 1H), 1.41(m, 2H), 1.36(d, 3H, J=6.6 Hz), 1.26(d, 6H, J=7.2 Hz), 1.26(td, 2H, J=18.6 Hz, 4.2 Hz); [M+1]⁺=449.2m/z(ESI)

<Preparation Example 2>Preparation of 3-(2,6-difluoro-4-(3-(1-(5-(5-isobutyl-1,2,4-oxadiazol-3-yl)pyrimidin-2-yl)piperidin-4-yl)propoxy)phenyl) -5-methyl-1,2,4-oxadiazole (Step 2-1) Preparation of 3-(1-(5-bromopyrimidin-2-yl)piperidin-4-yl)propan-1-ol

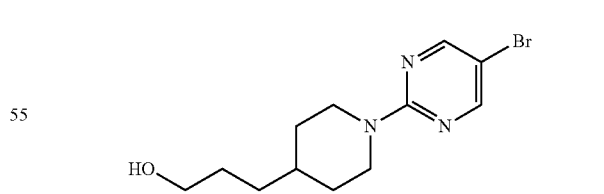

3-(Piperidin-4-yl)propan-1-ol of the Chemical Formula 2 (10 g, 69.8 mmol) and 5-bromo-2-chloropyrimidine (13.5 g, 69.8 mmol) were dissolved in N,N-dimethyl formamide (DMF, 10 ml), and then potassium carbonate (K₂CO₃, 10.6 g, 76.8 mmol) was added thereto, and the reaction was carried out at 80° C. for 12 hours. The reaction solution was cooled down to a room temperature, diluted with water, extracted with ethyl acetate (EA, 150 ml), and then washed with brine. Moisture was removed from an organic layer with MgSO₄, and the organic layer was filtered and concentrated under reduced pressure. The residue was purified with silica gel column chromatography to obtain the desired form of the compound, 3-(1-(5-bromopyrimidin-2-yl)piperidin-4-yl)propan-1-ol in a yield of 82%.

$^1$H NMR (400 MHz, CDCl₃) δ8.24 (s, 2H), 4.64 (d, 2H, J=15.2 Hz), 3.66-3.61 (m, 2H) 2.86-2.79 (m, 2H) 1.75 (d, 2H, J=12.4 Hz), 1.63-1.56 (m, 2H), 1.53-1.50 (m, 1H), 1.34-1.27 (m, 2H), 1.18-1.11 (m, 2H); [M+1]⁺=300.1 m/z (ESI).

(Step 2-2) Preparation of 2-(4-(3-hydroxypropyl)piperidin-1-yl)pyrimidin-5-carbonitrile

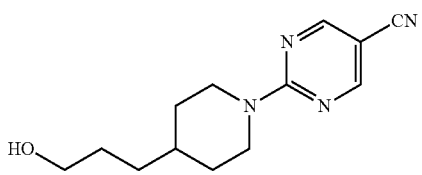 [SMILES: N#Cc1cnc(N2CCC(CCCO)CC2)nc1]

Copper cyanide (KCN, 222 g, 3.0 mol) and copper iodide (CuI, 22 g) were added to N-methyl-2-pyrrolidone (NMP, 750 ml), and then heated to 160° C. A solution of 3-(1-(5-bromopyrimidin-2-yl)piperidin-4-yl)propan-1-ol of Chemical Formula 9 synthesized in the above step 2-1 (222.0 g, 0.90 mol) dissolved in NMP (750 ml) was slowly added to the reaction solution. After stirring 3 hours, the reaction solution was diluted with EA, and washed with water (7500 ml). Moisture was removed from an organic layer with MgSO₄, and the organic layer was filtered and concentrated under reduced pressure, thereby obtaining the desired form of the compound, 2-(4-(3-hydroxypropyl)piperidin-1-yl)pyrimidin-5-carbonitrile in a yield of 83%.

$^1$H NMR (400 MHz, CDCl₃) δ8.46 (s, 2H), 4.84-4.81 (m, 2H), 3.67-3.64 (m, 2H), 2.95-2.90 (m, 2H), 1.84-1.82 (m, 2H), 1.64-1.59 (m, 2H), 1.36-1.33 (m, 2H), 1.29-1.27 (m, 1H), 1.20-1.13 (m, 2H); [M+1]⁺=247.2 m/z (ESI).

(Step 2-3) Preparation of N-hydroxy-2-(4-(3-hydroxypropyl)piperidin-1-yl)pyrimidin-5-carboxyimideamide

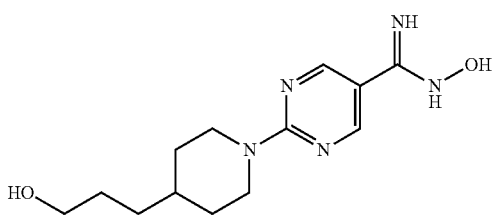 [SMILES: N=C(NO)c1cnc(N2CCC(CCCO)CC2)nc1]

2-(4-(3-Hydroxypropyl)piperidin-1-yl)pyrimidin-5-carbonitrile synthesized in the above step 2-2 (150.0 g, 0.61 mol) was dissolved in ethanol (1800 ml), and then hydroxyamine hydrate (430 g, 6.09 mol) was slowly dropped thereto. The reactant was stirred at room temperature for 18 hours, and then concentrated under reduced pressure, and water (1000 ml) was added thereto, and the reactant was stirred at 0-10° C. for 1 hour. The produced solid was filtered to obtain the desired form of the compound, N-hydroxy-2-(4-(3-hydroxypropyl)piperidin-1-yl)pyrimidin-5-carboxyimideamide in a yield of 85%.

[M+1]⁺=280.2 m/z (ESI).

(Step 2-4) Preparation of 2-(4-(3-hydroxypropyl)piperidin-1-yl)-N-((3-methylbutanoyl)oxy) pyrimidin-5-carboxyimideamide

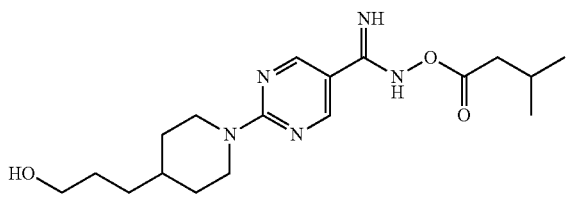 [SMILES: CC(C)CC(=O)ONC(=N)c1cnc(N2CCC(CCCO)CC2)nc1]

N-hydroxy-2-(4-(3-hydroxypropyl)piperidin-1-yl)pyrimidin-5-carboxyimideamide synthesized in the above step 2-3 (144.1 g, 0.516 mol) was dissolved in pyrimidine (3,000 ml), and then isovaleric acid (96.1 g, 0.516 mol) was slowly dropped thereto at 0-5° C. The reaction solution was stirred for 30 minutes to obtain the desired form of the compound, 2-(4-(3-hydroxypropyl)piperidin-1-yl)-N-((3-methylbutanoyl)oxy)pyrimidin-5-carboxyimideamide, which was used in the next reaction, without purification.

(Step 2-5) Preparation of 3-(1-(5-(5-isobutyl-1,2,4-oxadiazol-3-yl)pyrimidin-2-yl)piperidin-4-yl)propan-1-ol

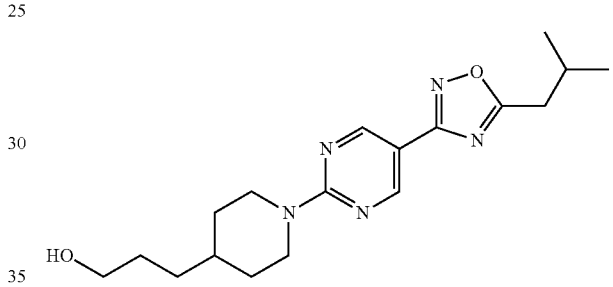

A reaction solution of 2-(4-(3-hydroxypropyl)piperidin-1-yl)-N-((3-methylbutanoyl)oxy)pyrimidin-5-carboxyimideamide synthesized in the above step 2-4 was heated to be stirred under reflux for 18 hours. The reaction solution was concentrated under reduced pressure, water (2500 ml) was dropped thereto at room temperature for 30 minutes, and then the reaction solution was stirred at 0-5° C. for 1 hour. The obtained solid was filtered to obtain the desired compound, 3-(1-(5-(5-isobutyl-1,2,4-oxadiazol-3-yl)pyrimidin-2-yl)piperidin-4-yl)propan-1-ol in a yield of 94%.

$^1$H NMR (600 MHz, CDCl₃) δ8.89 (s, 2H), 4.86 (d, 2H, J=13.2 Hz), 3.66 (t, 2H, J=13.2 Hz), 2.95-2.90 (m, 2H), 2.80 (d, 2H, J=7.2 Hz), 2.28-2.24 (m, 1H), 1.81(d, 2H, J=11.4 Hz), 1.65-1.61 (m, 2H), 1.60-1.36 (m, 1H), 1.35-1.22 (m, 2H), 1.22-1.15 (m, 2H), 1.04(d, 6H, J=6.0 Hz); [M+1]⁺=345.2 m/z (ESI).

(Step 2-6) Preparation of 3-(1-(5-(5-isobutyl-1,2,4-oxadiazol-3-yl)pyrimidin-2-yl) piperidin-4-yl)propyl methane sulfonate

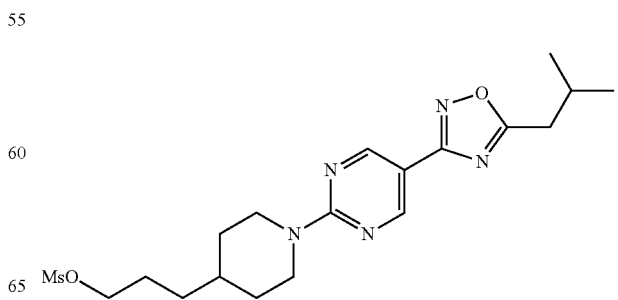

3-(1-(5-(5-isobutyl-1,2,4-oxadiazol-3-yl)pyrimidin-2-yl)piperidin-4-yl)propan-1-ol synthesized in the above step 2-5 (146.9 g, 0.43 mol) was dissolved in MC, and cooled down to 0° C. Triethylamine (89.1 ml, 0.64 mol) and methane sulfonyl chloride (39.7 ml, 0.51 mol) were slowly dropped to the reaction solution. The reaction solution was stirred at room temperature for 1 hour, diluted with EA, and washed with water. Moisture was removed from an organic layer with MgSO$_4$, and the organic layer was filtered and concentrated under reduced pressure, thereby obtaining the desired form of the compound, 3-(1-(5-(5-isobutyl-1,2,4-oxadiazol-3-yl)pyrimidin-2-yl)piperidin-4-yl)propylmethanesulfonate in a quantitative yield.

$^1$H NMR (600 MHz, CDCl$_3$) δ8.90 (s, 2H), 4.87 (d, 2H, J=13.8 Hz), 4.24 (t, 2H, J=13.2 Hz), 3.01 (s, 3H), 2.94-2.90 (m, 2H), 2.80 (d, 2H, J=7.2 Hz), 2.27-2.25 (m, 1H), 1.83-1.79 (m, 4H), 1.59 (m, 1H), 1.41-1.37 (m, 2H), 1.21-1.18 (m, 2H), 1.04 (d, 6H, J=6.0 Hz); [M+1]$^+$=242.2 m/z (ESI).

(Step 2-7) Preparation of 2,6-difluoro-4-(3-(1-(5-(5-isobutyl-1,2,4-oxadiazol-3-yl) pyrimidin-2-yl)piperidin-4-yl)propoxy)benzonitrile

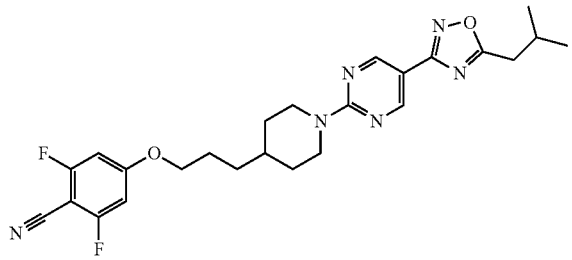 [SMILES: CC(C)Cc1nc(-c2cnc(N3CCC(CCCOc4cc(F)c(C#N)c(F)c4)CC3)nc2)no1]

2,6-Difluoro-4-hydroxybenzonitrile (6.6 g, 0.042 mol) was dissolved in N,N-dimethyl formamide (DMF, 0.3 L), and 3-(1-(5-(5-isobutyl-1,2,4-oxadiazol-3-yl)pyrimidin-2-yl)piperidin-4-yl)propyl methane sulfonate synthesized in the above step 2-6 (15 g, 0.035 mol) and potassium carbonate (K$_2$CO$_3$, 14.7 g, 0.11 mol) were added to the reaction solution. The reaction solution was stirred at 60° C. for 18 hours, and then diluted with water, and extracted with EA. Moisture was removed from an organic layer with MgSO$_4$, and the organic layer was filtered and concentrated under reduced pressure. The residue was purified with silica gel column chromatography to obtain the desired form of the compound, 2,6-difluoro-4-(3-(1-(5-(5-isobutyl-1,2,4-oxadiazol-3-yl)pyrimidin-2-yl)piperidin-4-yl)propoxy) benzonitrile in a yield of 85%.

$^1$H NMR (600 MHz, CDCl$_3$) δ8.88 (s, 2H), 6.44 (d, 2H, J$_{HF}$=10.2 Hz), 4.86 (d, 2H, J=13.2 Hz), 3.95-3.93 (m, 2H), 3.89 (s, 3H), 2.94-2.89 (m, 2H), 2.79 (d, 2H, J=7.8 Hz), 2.27-2.22 (m, 1H), 1.85-1.80 (m, 4H), 1.61-1.59 (m, 1H), 1.43-1.39 (m, 2H), 1.23-1.19 (m, 2H), 1.02 (d, 6H, J=7.2 Hz); [M+1]$^+$=516.3 m/z (ESI).

(Step 2-8) Preparation of 2,6-difluoro-N-hydroxy-4-(3-(1-(5-(5-isobutyl-1,2,4-oxadiazol-3-yl)pyrimidin-2-yl)piperidin -4-yl)propoxy)benzimideamide

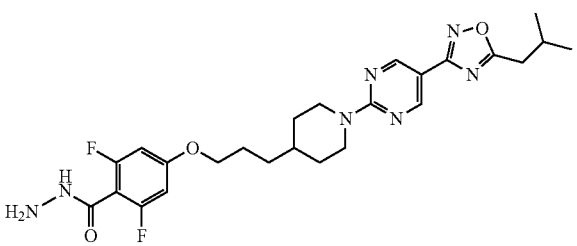 [SMILES: CC(C)Cc1nc(-c2cnc(N3CCC(CCCOc4cc(F)c(C(=O)NN)c(F)c4)CC3)nc2)no1]

2,6-Difluoro-4-(3-(1-(5-(5-isobutyl-1,2,4-oxadiazol-3-yl)pyrimidin-2-yl)piperidin-4-yl) propoxy)benzonitrile synthesized in the above step 2-7 (5.7 g, 11.81 mmol) was dissolved in ethanol (68 ml), and then a 50% aqueous hydroxylamine solution (7.24 ml, 118.1 mmol) was added thereto. The reaction solution was stirred at 100° C. for 5 hours, then cooled down to room temperature, and concentrated to a ¹/₁₀ volume. To the concentrate, water (38 ml) was dropped, then stirring was carried out for 1 hour, and the produced solid was filtered out therefrom, thereby obtaining the desired form of the compound, 2,6-difluoro-N-hydroxy-4-(3-(1-(5-(5-isobutyl-1,2,4-oxadiazol-3-yl)pyrimidin-2-yl)piperidin -4-yl)propoxy)benzimideamide in a quantitative yield.

$^1$H NMR (600 MHz, CDCl$_3$) δ8.88 (s, 2H), 6.44 (d, 2H, J$_{HF}$=10.2 Hz), 4.86 (d, 2H, J=13.2 Hz), 3.95-3.93 (m, 2H), 3.89 (s, 3H), 2.94-2.89 (m, 2H), 2.79 (d, 2H, J=7.8 Hz), 2.27-2.22 (m, 1H), 1.85-1.80 (m, 4H), 1.61-1.59 (m, 1H), 1.43-1.39 (m, 2H), 1.23-1.19 (m, 2H), 1.02 (d, 6H, J=7.2 Hz); [M+1]$^+$=516.3 m/z (ESI).

(Step 2-9) Preparation of 3-(2,6-difluoro-4-(3-(1-(5-(5-isobutyl-1,2,4-oxadiazol-3-yl) pyrimidin-2-yl)piperidin-4-yl)propoxy)phenyl)-5-methyl-1,2,4-oxadiazole (Example 2)

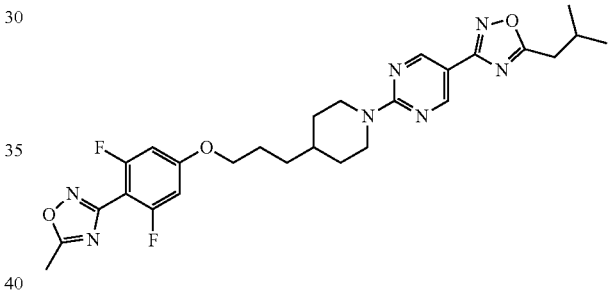

2,6-Difluoro-N-hydroxy-4-(3-(1-(5-(5-isobutyl-1,2,4-oxadiazol-3-yl)pyrimidin-2-yl) piperidin-4-yl)propoxy)benzimideamide obtained in the above step 2-8 (70 mg, 0.14 mmol) was dissolved in N,N-dimethyl formamide (DMF, 4 ml), and then triethylamine (0.023 ml, 0.16 mmol) and acetyl chloride (0.013 ml, 0.16 mmol) were dropped thereto. The reaction solution was stirred at room temperature for 1 hour, and then further stirred at 140° C. for 3 hours. After cooling down to room temperature, the solution was diluted with water, and extracted with EA. Moisture was removed from an organic layer with MgSO$_4$, and the organic layer was filtered and concentrated under reduced pressure. The residue was purified with silica gel column chromatography to obtain the desired form of the compound, 3-(2,6-difluoro-4-(3-(1-(5-(5-isobutyl-1,2,4-oxadiazol-3-yl)pyrimidin-2-yl)piperidin-4-yl)prop oxy)phenyl)-5-methyl-1,2,4-oxadiazole in a yield of 85%.

$^1$H NMR (600 MHz, CDCl$_3$) δ8.88 (s, 2H), 6.55 (d, 2H, J$_{HF}$=10.2 Hz), 4.86 (d, 2H, J=13.8 Hz), 3.95-3.93 (m, 2H), 3.97 (t, 2H, J=13.2 Hz), 2.94-2.89 (m, 2H), 2.79 (d, 2H, J=7.8 Hz), 2.64 (s, 3H), 2.25-2.23 (m, 1H), 1.85-1.81 (m, 4H), 1.56 (m, 1H), 1.44-1.40 (m, 2H), 1.21-1.19 (m, 2H), 1.02 (d, 6H, J=6.7 Hz); [M+1]$^+$=540.2 m/z (ESI).

<Preparation Example 3>Preparation of 2-(4-(3-(1-(5-ethylpyrimidin-2-yl)piperidin-4-yl)propoxy)-2,6-difluorophenyl)-5-methyl-1,3,4-oxadiazole (Step 3-1) Preparation of methyl 4-(3-(1-(5-ethylpyrimidin-2-yl)piperidin-4-yl) propoxy)-2,6-difluorobenzoate

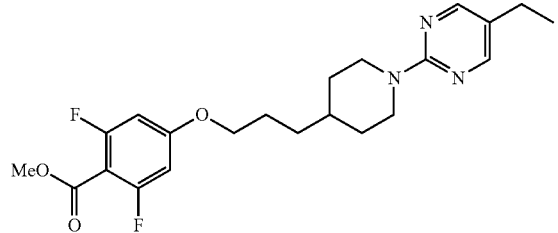 [SMILES: CCc1cnc(N2CCC(CCCOc3cc(F)c(C(=O)OC)c(F)c3)CC2)nc1]

Methyl 2,6-difluoro-4-hydroxybenzoate (1.72 g, 9.16 mmol) was dissolved in N,N-dimethyl formamide (DMF, 30 ml), and then 3-(1-(5-ethylpyrimidin-2-yl)piperidin-4-yl) propyl methane sulfonate (3.3 g, 10.08 mmol) and potassium carbonate ($K_2CO_3$, 3.8 g, 27.5 mmol) were added to the reaction solution. The reaction solution was stirred at 65° C. for 12 hours, and then diluted with water, and extracted with EA. Moisture was removed from an organic layer with $MgSO_4$, the organic layer was filtered and concentrated under reduced pressure, and the residue was purified with silica gel column chromatography to obtain the desired form of the compound, methyl 4-(3-(1-(5-ethylpyrimidin-2-yl)piperidin-4-yl)propoxy)-2,6-difluorobenzoate in a yield of 93%.

$^1$H NMR(400 MHz, $CDCl_3$) δ8.13(s, 2H), 6.43(d, 2H, J=10.8 Hz), 4.68(d, 2H, J=12.8 Hz), 3.93(t, 2H, J=6.4 Hz), 3.88(s, 3H), 2.82(t, 2H, J=12.8 Hz), 2.42(q, 2H, J=7.6 Hz), 1.79(m, 4H), 1.53(m, 1H), 1.38(m, 2H), 1.19(m, 2H), 1.15(t, 3H, J=7.6 Hz); [M+1]$^+$=420.2 m/z(ESI).

(Step 3-2) Preparation of 4-(3-(1-(5-ethylpyrimidin-2-yl)piperidin-4-yl-propoxy) -2,6-difluorobenzoic acid

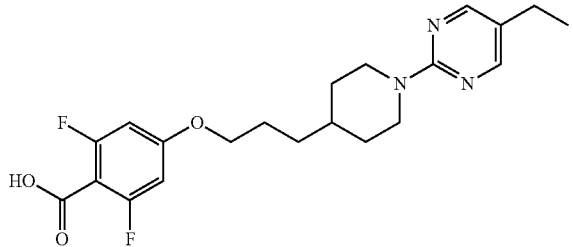 [SMILES: CCc1cnc(N2CCC(CCCOc3cc(F)c(C(=O)O)c(F)c3)CC2)nc1]

Methyl 4-(3-(1-(5-ethylpyrimidin-2-yl)piperidin-4-yl) propoxy)-2,6-difluorobenzoate synthesized in the above step 3-1 (14.26 g, 34 mmol) was dissolved in ethanol (250 ml), and then 2N aqueous sodium hydroxide solution (85 ml, 170 mmol) was added thereto. The reaction solution was stirred at 70° C. for 15 hours, and then diluted with water, and a 2N aqueous HCl solution was added thereto, to acidify the solution. The mixed solution was extracted with EA, moisture was removed from an organic layer with $MgSO_4$, and the organic layer was filtered and concentrated under reduced pressure, thereby obtaining the desired form of the compound, 4-(3-(1-(5-ethylpyrimidin-2-yl)piperidin-4-yl) propoxy)-2,6-difluorobenzoic acid in a quantitative yield.

$^1$H NMR (600 MHz, $CDCl_3$) δ8.15(s, 2H), 6.48(d, 2H, J=8.0 Hz), 4.69(d, 2H, J=8.8 Hz), 3.79(t, 2H, J=4.4 Hz), 2.87(t, 2H, J=8.4 Hz), 2.46(q, 2H, J=4.4 Hz), 1.85(m, 2H), 1.84(d, 2H, J=8.4 Hz), 1.57(m, 1H), 1.42(m, 2H), 1.24(m, 2H), 1.20(m, 3H); [M+1]$^+$=406.2 m/z (ESI).

(Step 3-3) Preparation of 4-(3-(1-(5-ethylpyrimidin-2-yl) piperidin-4-yl)propoxy) -2,6-difluorobenzohydrazide

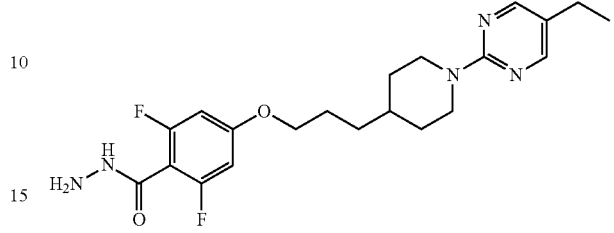

4-(3-(1-(5-Ethylpyrimidin-2-yl)piperidin-4-yl)propoxy)-2,6-difluoro benzoic acid synthesized in the above step 3-2 (12.16 g, 30 mmol) was dissolved in dichloromethane (300 ml), and then 1-ethyl-3-(3-dimethylaminopropyl)carbodiimide hydrochloride (11.5 g, 60 mmol) and hydroxybenzotriazole (9.19 g, 60 mmol) were added thereto, and stirred at room temperature for 30 minutes. Thereafter, hydrazine hydrate (65%, 2.73 ml, 36 mmol) was dropped thereto, and then further stirred for 15 minutes. The mixed solution was extracted with dichloromethane, moisture was removed from an organic layer with $MgSO_4$, and the organic layer was filtered and concentrated under reduced pressure, thereby obtaining the desired form of the compound, 4-(3-(1-(5-ethylpyrimidin-2-yl)piperidin-4-yl)propoxy)-2,6-difluorobenzohydrazide in a quantitative yield, which was used in the next reaction, without purification.

[M+1]$^+$=420.2 m/z (ESI).

(Step 3-4) Preparation of 2-(4-(3-(1-(5-ethylpyrimidin-2-yl)piperidin-4-yl)propoxy) -2,6-difluorophenyl)-5-methyl-1,3,4-oxadiazole (Preparation Example 3)

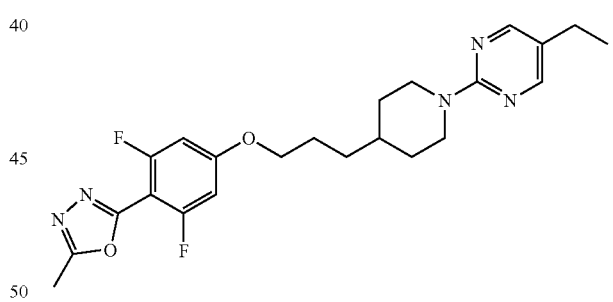

4-(3-(1-(5-Ethylpyrimidin-2-yl)piperidin-4-yl)propoxy)-2,6-difluoro benzohydrazide obtained in the above step 3-3 (12.6 g) was dissolved in triethylorthoacetate (50 ml), and then stirred at 120° C. for 6 hours. The reaction solution was concentrated under reduced pressure, and the residue was purified with silica gel column chromatography, thereby obtaining the desired form of the compound, 2-(4-(3-(1-(5-ethylpyrimidin-2-yl)piperidin-4-yl)propoxy)-2,6-difluorophenyl)-5-methyl-1,3,4-oxadiazole (9.09 g, 20.49 mmol) in a yield of 68%.

$^1$H NMR(600 MHz, $CDCl_3$) δ8.15(appr-s, 2H), 6.57 (appr-d, 2H, J=10.2 Hz), 4.69(d, 2H, J=11.4 Hz), 3.98(t, 2H, J=6.0 Hz), 2.85(appr-t, 2H, J=5.4 Hz), 2.61(s, 3H), 2.44(q, 2H, J=7.8 Hz), 1.84(m, 3H), 1.78(d, 2H, J=12.0 Hz), 1.41(m, 2H), 1.22(m, 2H), 1.18(t, 3H, J=7.8 Hz); [M+1]$^+$=444.2 m/z(ESI).

<Preparation Example 4>Preparation of 2-(4-(3-(1-(5-ethylpyrimidin-2-yl)piperidin-4-yl)propoxy)-2,6-difluorophenyl)-5-isopropyl-1,3,4-thiadiazole (Step 4-1) Preparation of 4-(3-(1-(5-ethylpyrimidin-2-yl)piperidin-4-yl)propoxy) -2,6-difluoro-N'-isobutyrylbenzohydrazide

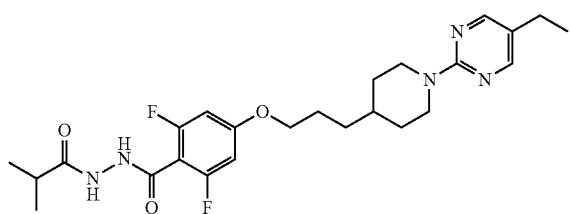 [SMILES: CCc1cnc(N2CCC(CCCOc3cc(F)c(C(=O)NNC(=O)C(C)C)c(F)c3)CC2)nc1]

4-(3-(1-(5-ethylpyrimidin-2-yl)piperidin-4-yl-propoxy)-2,6-difluorobenzoic acid synthesized in the above step 3-2 of <Preparation Example 3>was dissolved in dichloromethane (4 ml), and then EDC(70.9 mg, 0.37 mmol) and HOBt·H$_2$O (56.7 mg, 0.37 mmol) were added thereto. After activating at room temperature for 1 hour, isobutyrohydrazide (37.8 mg, 0.37 mmol) was dropped thereto, and stirring was carried out for 18 hours. After completion of the reaction, the reactant was filtered through celite, and then concentrated under reduced pressure to obtain the desired form of the compound, 4-(3-(1-(5-ethylp yrimidin-2-yl)piperidin-4-yl)propoxy)-2,6-difluoro-N'-is obutyrylbenzohydra zide in a yield of 88%.

[M+1]$^+$=490.3 m/z(ESI). (Step 4-2) Preparation of 2-(4-(3-(1-(5-ethylpyrimidin-2-yl)piperidin-4-yl)propoxy) -2,6-difluorophenyl)-5-isopropyl-1,3,4-thiadiazole (Preparation Example 4)

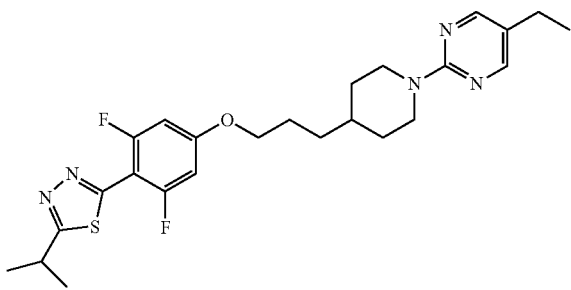 [SMILES: CCc1cnc(N2CCC(CCCOc3cc(F)c(-c4nnc(C(C)C)s4)c(F)c3)CC2)nc1]

4-(3-(1-(5-Ethylpyrimidin-2-yl)piperidin-4-yl)propoxy)-2,6-difluoro-N'-isobutyrylben zohydrazide obtained in the above step 4-1 (22 mg, 0.05 mmol) was dissolved in xylene (4 ml), Lawesson's reagent (27.3 mg, 0.07 mmol) was added thereto, and stirring was carried out at 140° C. for 30 minutes. After completion of the reaction, dilution with water, and extraction with ethyl acetate were carried out. Moisture was removed from an organic layer with MgSO$_4$, the organic layer was filtered and concentrated under reduced pressure, and then the residue was purified with silica gel column chromatography, thereby obtaining the desired form of the compound, 2-(4-(3-(1-(5-ethylpyrimidin-2-yl)piperidin-4-yl)propoxy)-2,6-difluoro phenyl)-5-isopropyl-1,3,4-thiadiazole in a yield of 44%.

$^1$H NMR (600 MHz, CDCl$_3$) δ8.14 (s, 2H), 6.56 (d, 2H, J=10.4 Hz), 4.68 (d, 2H, J=13.2 Hz), 3.96 (t, 2H, J=12.8 Hz), 3.50 (m, 1H), 2.83 (td, 2H, J=12.4 Hz, 1.6 Hz), 2.42 (m, 2H), 1.81 (m, 4H), 1.52 (m, 1H), 1.44 (d, 6H, J=10.0 Hz), 1.40 (m, 2H), 1.20 (m, 2H), 1.16 (m, 3H); [M+1]$^+$=488.3 m/z (ESI).

<Preparation Example 5>Preparation of 4-ethyl-2-(4-(3-(1-(5-ethylpyrimidin-2-yl)piperidin-4-yl)propoxy)-2,6-difluorophenyl)thiazole (Step 5-1) Preparation of 4-(3-(1-(5-ethylpyrimidin-2-yl)piperidin-4-yl) propoxy)-2,6-difluorobenzoyl chloride

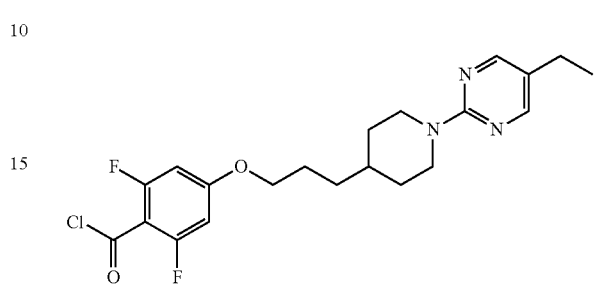

4-(3-(1-(5-ethylpyrimidin-2-yl)piperidin-4-yl-propoxy)-2,6-difluorobenzoic acid synthesized in the above step 3-2 of <Preparation Example 3>(1.39 g, 3.42 mmol) was dissolved in dichloromethane (15 ml), then thionyl chloride (0.75 ml, 10.27 mmol) was dropped thereto, and stirring was carried out at 65° C. for 4 hours. After completion of the reaction, dilution with water, extraction with dichloromethane, and then washing with brine were carried out. Moisture was removed from an organic layer with MgSO$_4$, and the organic layer was filtered and concentrated under reduced pressure, thereby obtaining the desired form of the compound, 4-(3-(1-(5-ethylpyrimidin-2-yl)piperidin-4-yl)propoxy)-2,6-difluorobenzoyl chloride in a quantitative yield.

[M+1]$^+$=424.2 m/z(ESI).

(Step 5-2) Preparation of 4-(3-(1-(5-ethylpyrimidin-2-yl)piperidin-4-yl) propoxy)-2,6-difluorobenzamide

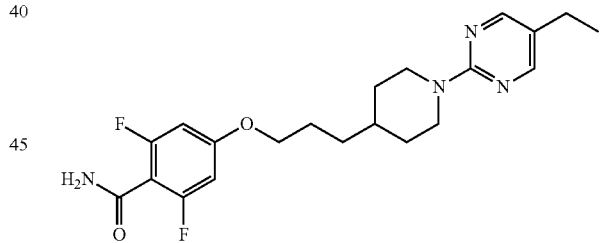

4-(3-(1-(5-Ethylpyrimidin-2-yl)piperidin-4-yl)propoxy)-2,6-difluorobenzoyl chloride synthesized in the above step 5-1 (1.46 g, 3.44 mmol) was dissolved in benzene (10 ml), then sodium hydroxide (0.83 g, 20.65 mmol) and ammonium chloride (0.55 g, 10.32 mmol) were added thereto, and stirred for 2 hours. After completion of the reaction, dilution with water, extraction with ethyl acetate, and then washing with brine were carried out. Moisture was removed from an organic layer with MgSO$_4$, and the organic layer was filtered and concentrated under reduced pressure. The concentrated residue was purified with silica gel column chromatography to obtain the desired form of the compound, 4-(3-(1-(5-ethylpyrimidin-2-yl)piperidin-4-yl)propoxy)-2,6-difluorobenzamide in a yield of 84%.

$^1$H NMR (400 MHz, CDCl$_3$) δ8.14 (s, 2H), 6.46 (dd, 2H, J=5.2 Hz, 15.6 Hz), 6.03 (s, 1H), 5.83 (s, 1H), 4.68 (d, 2H, J=13.2 Hz), 3.93 (t, 2H, J=12.8 Hz), 2.83 (m, 2H), 2.4 3(m,

2H), 1.82 (m, 4H), 1.63 (m, 1H), 1.54 (m, 1H), 1.39 (m, 2H), 1.16 (m, 4H); [M+1]⁺=405.2 m/z (ESI).

(Step 5-3) Preparation of 4-(3-(1-(5-ethylpyrimidin-2-yl)piperidin-4-yl)propoxy) -2,6-difluorobenzothioamide

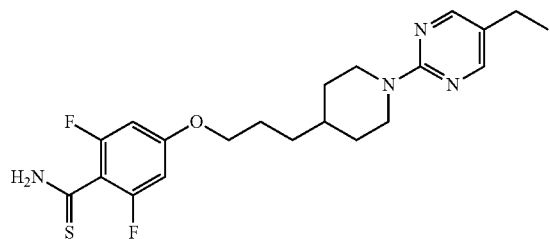 [SMILES: CCc1cnc(N2CCC(CCCOc3cc(F)c(C(N)=S)c(F)c3)CC2)nc1]

4-(3-(1-(5-ethylpyrimidin-2-yl)piperidin-4-yl)propoxy)-2,6-difluorobenzamide synthesized in the above step 5-2 (1.17 g, 2.88 mmol) was dissolved in tetrahydrofuran (THF, 10 ml), then Lawesson's reagent (1.75 g, 4.32 mmol) was added thereto, and stirred at 50° C. for 3 hours. After completion of the reaction, dilution with water, and extraction with ethyl acetate were carried out. Moisture was removed from an organic layer with MgSO₄, the organic layer was filtered and concentrated under reduced pressure, and the residue was purified with silica gel column chromatography to obtain the desired form of the compound, 4-(3-(1-(5-ethylpyrimidin-2-yl)piperidin-4-yl)propoxy)-2,6-difluorobenzothioamide in a yield of 32%.

[M+1]⁺=421.2 m/z(ESI).

(Step 5-4) Preparation of 4-ethyl-2-(4-(3-(1-(5-ethylpyrimidin-2-yl)piperidin-4-yl) propoxy)-2,6-difluorophenyl)thiazole (Preparation Example 5)

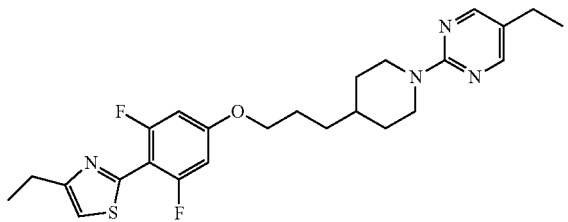 [SMILES: CCc1cnc(N2CCC(CCCOc3cc(F)c(-c4nc(CC)cs4)c(F)c3)CC2)nc1]

4-(3-(1-(5-Ethylpyrimidin-2-yl)piperidin-4-yl)propoxy)-2,6-difluorobenzothioamide (0.38 g, 0.91 mmol), the compound synthesized in the above step 5-3 was dissolved in ethanol (6 ml), and then 1-bromobutan-2-on (3.3 μl, 0.91 mmol) was dropped thereto at room temperature. The reactant was stirred under reflux at 100° C. After completion of the reaction, the solvent was concentrated under reduced pressure, and an organic layer was extracted using water and ethyl acetate. Moisture was removed from an organic layer with MgSO₄, the organic layer was filtered and concentrated under reduced pressure, and the residue was purified with silica gel column chromatography to obtain the desired form of the compound, 4-ethyl-2-(4-(3-(1-(5-ethylpyrimidin-2-yl)piperidin-4-yl)propoxy)-2,6-difluorophenyl)thiazole in a yield of 62%.

¹H NMR (400 MHz, CDCl₃) δ8.11 (s, 2H), 6.98 (s, 1H), 6.49 (d, 2H, J=15.6 Hz), 4.66 (d, 2H, J=13.2 Hz), 3.91 (m, 2H), 2.82 (m, 4H), 2.40 (m, 2H), 1.78 (m, 4H), 1.51 (m, 1H), 1.37 (m, 2H), 1.29 (m, 3H), 1.18 (m, 2H), 1.13 (m, 3H); [M+1]⁺=473.2 m/z (ESI).

<Preparation Example 6>Preparation of 3-(4-(3-(1-(5-ethylpyrimidin-2-yl)piperidin-4-yl)propoxy)-2,6-difluorophenyl)-5-isopropyl-1,2,4-oxadiazole (Step 6-1) Preparation of 2,6-difluoro-N',4-dihydrobenzimidamide

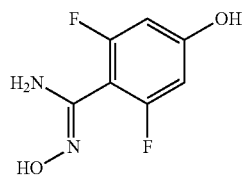

2,6-Difluoro-4-hydroxybenzonitrile (3.0 g, 19.3 mmol) was dissolved in ethanol (12mL), and then a 50% aqueous hydroxyamine solution (NH₂OH, 12.6 g, 193.0 mmol) was added to the reaction solution. The reaction solution was stirred under reflux for 3 hours, then concentrated under reduced pressure to remove the solvent, water was added thereto, and filtering was carried out, thereby obtaining the desired form of the compound, 2,6-difluoro-N',4-dihydrobenzimidamide in a yield of 75%.

[M+1]⁺=189.0 m/z(ESI).

(Step 6-2) Preparation of 3,5-difluoro-4-(5-isopropyl-1,2,4-oxadiazol-3-yl)phenol

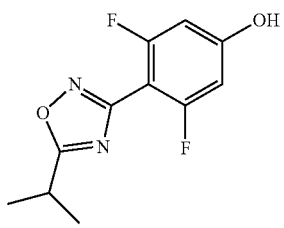 [SMILES: CC(C)c1nc(-c2c(F)cc(O)cc2F)no1]

2,6-Difluoro-N',4-dihydrobenzimidamide (2.6 g, 10.6 mmol), the compound synthesized in the above step 6-1 was dissolved in 1,4-dioxane (80 ml), and then isobutyric anhydride (1.7 g, 10.6 mmol) was added to the reaction solution. The reaction solution was stirred for 1 hour, magnesium sulfate (MgSO₄, 2.6 g) was added thereto, and stirred under reflux for 18 hours. The reaction solution was concentrated under reduced pressure, then the residue was purified with silica gel column chromatography, and further ether was added thereto, then filtering was carried out, thereby obtaining the desired form of the compound, 3,5-difluoro-4-(5-isopropyl-1,2,4-oxadiazol-3-yl)phenol in a yield of 48%.

¹H NMR(400 MHz, DMSO-d₆) δ11.07 (br s, 1H), 6.68 (d, 2H, J=14.8 Hz), 3.37 (m, 1H), 1.38 (d, 6H, J=6.8 Hz)

(Step 6-3) Preparation of 3-(1-(5-ethylpyrimidin-2-yl)piperidin-4-yl)propan-1-ol

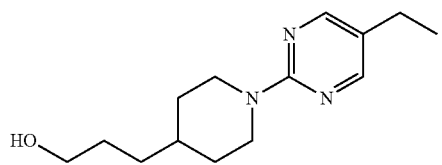 [SMILES: CCc1cnc(N2CCC(CCCO)CC2)nc1]

2-chloro-5-ethyl pyrimidine (1.0 g, 7.0 mmol) was dissolved in N,N-dimethyl formamide (DMF, 15 ml), and then 3-(piperidin-4-yl)propan-1-ol (1.1 g, 7.7 mmol) and potassium carbonate (K$_2$CO$_3$, 2.9 g, 21.0 mmol) were added to the reaction solution. The reaction solution was stirred at 65° C. for 12 hours, and then diluted with water, and extracted with EA. Moisture was removed from an organic layer with MgSO$_4$, the organic layer was filtered and concentrated under reduced pressure, and the residue was purified with silica gel column chromatography to obtain the desired form of the compound, 3-(1-(5-ethylpyrimidin-2-yl)piperidin-4-yl)propan-1-ol in a yield of 75%.

$^1$H NMR(400 MHz, CDCl$_3$) δ8.15 (s, 2H), 4.67 (d, 2H, J=13.6 Hz), 2.87 (m, 2H), 2.83 (t, 2H, J=12.6 Hz), 2.44 (q, 2H, J=7.6 Hz), 1.46-1.38 (m, 9H), 1.21 (t, 3H, J=7.6 Hz)

(Step 6-4) Preparation of 3-(1-(5- ethylpyrimidin-2-yl)piperidin-4-yl)propyl methane sulfonate

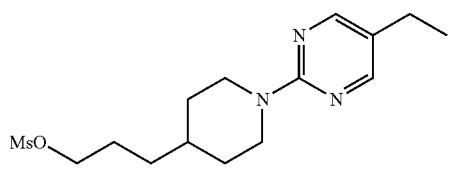 [SMILES: CCc1cnc(N2CCC(CCCOS(C)(=O)=O)CC2)nc1]

3-(1-(5-ethylpyrimidin-2-yl)piperidin-4-yl)propan-1-ol synthesized in the above step 6-3 (1.0 g, 4.0 mmol) was dissolved in MC, and cooled down to 0° C. Triethylamine (0.6 g, 6.0 mmol) and methane sulfonyl chloride (0.6 g, 4.8 mmol) were slowly dropped to the reaction solution. The reaction solution was stirred at room temperature for 1 hour, diluted with MC, and washed with water. Moisture was removed from an organic layer with MgSO$_4$, and the organic layer was filtered and concentrated under reduced pressure, thereby obtaining the desired form of the compound, 3-(1-(5-ethylpyrimidin-2-yl)piperidin-4-yl)propyl methane sulfonate in a quantitative yield.

$^1$H NMR(400 MHz, CDCl$_3$) δ8.13 (s, 2H), 4.69 (d, 2H, J=13.2 Hz,), 4.22 (t, 2H, J=6.8 Hz), 2.98 (s, 3H), 2.84 (t, 2H, J=13.2 Hz), 2.45 (q, 2H, J=7.6 Hz), 1.82 (m, 4H), 1.55 (m, 2H), 1.37 (m, 2H), 1.20 (t, 3H, J=7.6 Hz)

(Step 6-5) Preparation of 3-(4-(3-(1-(5-ethylpyrimidin-2-yl)piperidin-4-yl)propoxy) -2,6-difluorophenyl)-5-isopropyl-1,2,4-oxadiazole (Preparation Example 6)

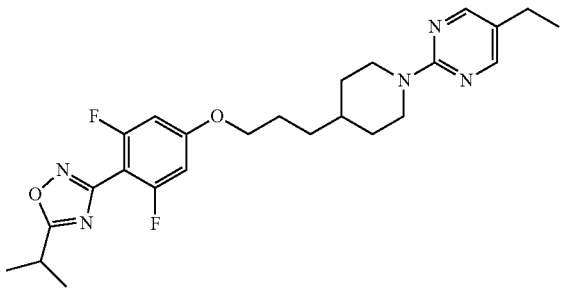 [SMILES: CCc1cnc(N2CCC(CCCOc3cc(F)c(-c4noc(C(C)C)n4)c(F)c3)CC2)nc1]

3,5-Difluoro-4-(5-isopropyl-1,2,4-oxadiazol-3-yl)phenol synthesized in the above step 6-2 (10. g, 4.1 mmol) was dissolved in N,N-dimethylform amide (DMF, 15 ml), and then 3-(1-(5- ethylpyrimidin-2-yl)piperidin-4-yl)propyl methane sulfonate synthesized in the above step 6-4 (1.2 g, 3.7 mmol) and potassium carbonate (K$_2$CO$_3$, 1.7 g, 12.4 mmol) were added to the reaction solution. The reaction solution was stirred at 65° C. for 17 hours, and then diluted with water, and extracted with EA. Moisture was removed from an organic layer with MgSO$_4$, the organic layer was filtered and concentrated under reduced pressure, and then the residue was purified with silica gel column chromatography, thereby obtaining the desired form of the compound, 3-(4-(3-(1-(5-ethylpyrimidin-2-yl)piperidin-4-yl)propoxy)-2,6-difluorophenyl)-5-isopropyl-1,2,4-oxadiazole in a yield of 73%.

$^1$H NMR(400 MHz, CDCl$_3$) δ8.14 (s, 2H), 6.54 (d, 2H, J=9.6 Hz), 4.67 (d, 2H, J=13.2 Hz), 3.96 (t, 2H, J=6.6H), 3.30 (m, 1H), 2.83 (m, 2H), 2.43 (q, 2H, J=7.4 Hz), 1.83 (m, 2H), 1.77 (m, 2H), 1.52 (m, 1H), 1.44 (d, 6H, J=7.2 Hz), 1.39 (m, 2H), 1.21 (m, 2H), 1.16 (t, 3H, J=7.4 Hz)

According to the preparation processes of the above Examples, a reagent corresponding to each substituent of each Example was used to prepare the compounds of Examples 1 to 67 in the following Table 1.

TABLE 1

| No. of Example | Chemical structure | Chemical name | Mass [M + 1]$^+$ |
|---|---|---|---|
| 1 | 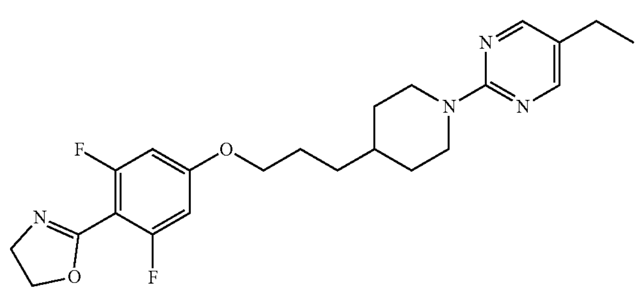 [SMILES: CCc1cnc(N2CCC(CCCOc3cc(F)c(C4=NCCO4)c(F)c3)CC2)nc1] | 2-(4-(3-(1-(5-ethylpyrimidin-2-yl)piperidin-4-yl)propoxy)-2,6-difluorophenyl)-4,5-dihydrooxazole, | 431.2 |

TABLE 1-continued

| No. of Example | Chemical structure | Chemical name | Mass [M + 1]+ |
|---|---|---|---|
| 2 | 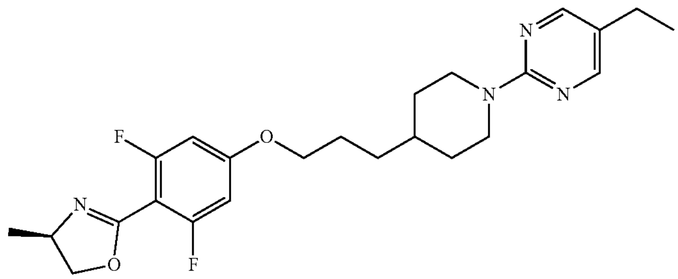 [SMILES: CCc1cnc(N2CCC(CCCOc3cc(F)c(C4=N[C@H](C)CO4)c(F)c3)CC2)nc1] | (R)-2-(4-(3-(1-(5-ethylpyrimidin-2-yl)piperidin-4-yl)propoxy)-2,6-difluorophenyl)-4-methyl-4,5-dihydrooxazole | 445.2 |
| 3 | 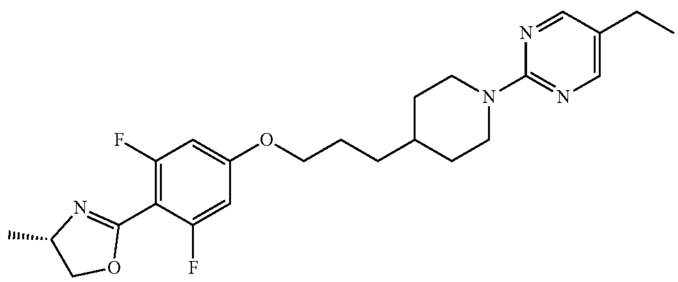 [SMILES: CCc1cnc(N2CCC(CCCOc3cc(F)c(C4=N[C@@H](C)CO4)c(F)c3)CC2)nc1] | (S)-2-(4-(3-(1-(5-ethylpyrimidin-2-yl)piperidin-4-yl)propoxy)-2,6-difluorophenyl)-4-methyl-4,5-dihydrooxazole | 445.2 |
| 4 | 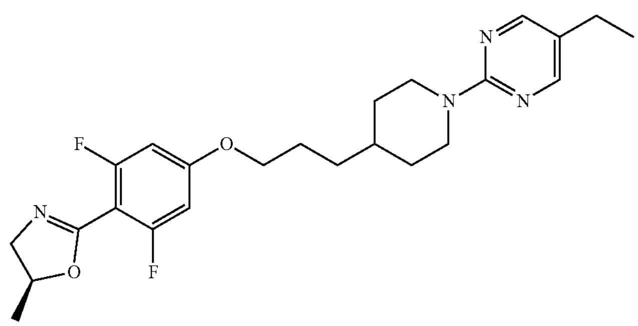 [SMILES: CCc1cnc(N2CCC(CCCOc3cc(F)c(C4=NC[C@H](C)O4)c(F)c3)CC2)nc1] | (S)-2-(4-(3-(1-(5-ethylpyrimidin-2-yl)piperidin-4-yl)propoxy)-2,6-difluorophenyl)-5-methyl-4,5-dihydrooxazole | 445.2 |
| 5 | 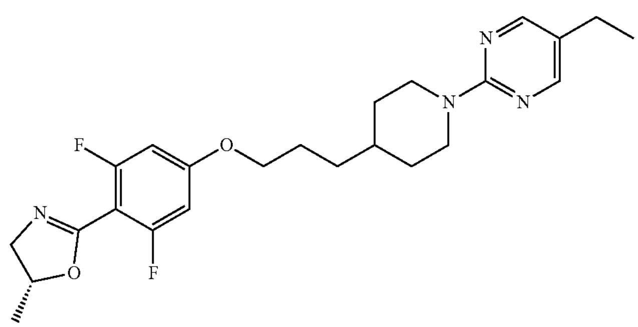 [SMILES: CCc1cnc(N2CCC(CCCOc3cc(F)c(C4=NC[C@@H](C)O4)c(F)c3)CC2)nc1] | (R)-2-(4-(3-(1-(5-ethylpyrimidin-2-yl)piperidin-4-yl)propoxy)-2,6-difluorophenyl)-5-methyl-4,5-dihydrooxazole | 445.2 |
| 6 | 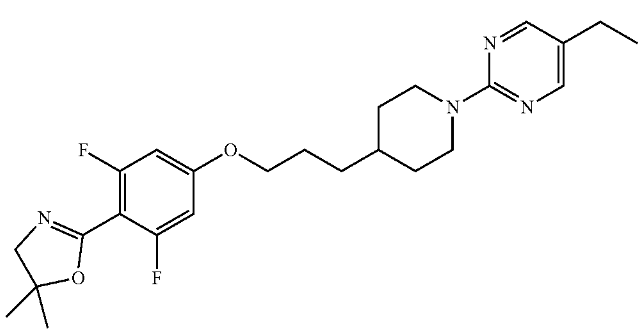 [SMILES: CCc1cnc(N2CCC(CCCOc3cc(F)c(C4=NCC(C)(C)O4)c(F)c3)CC2)nc1] | 2-(4-(3-(1-(5-ethylpyrimidin-2-yl)piperidin-4-yl)propoxy)-2,6-difluorophenyl)-5,5-dimethyl-4,5-dihydrooxazole | 459.3 |

TABLE 1-continued

| No. of Example | Chemical structure | Chemical name | Mass [M + 1]+ |
|---|---|---|---|
| 7 | 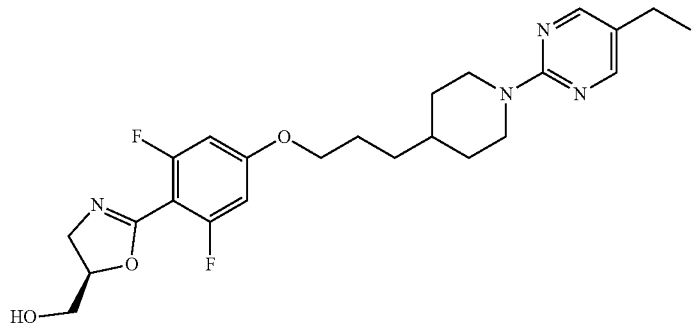 [SMILES: CCc1cnc(N2CCC(CCCOc3cc(F)c(C4=NC[C@H](CO)O4)c(F)c3)CC2)nc1] | (R)-(2-(4-(3-(1-(5-ethylpyrimidin-2-yl)piperidin-4-yl)propoxy)-2,6-difluorophenyl)-4,5-dihydrooxazol-5-yl)methanol | 461.2 |
| 8 | 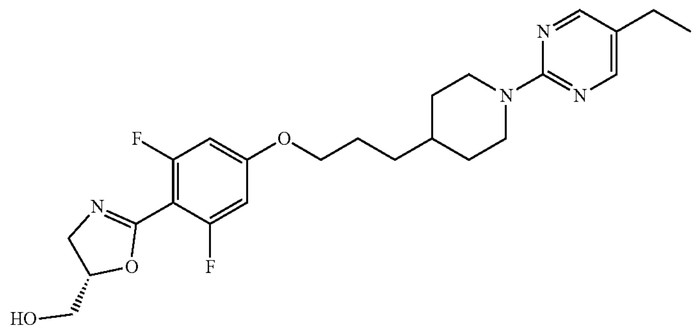 [SMILES: CCc1cnc(N2CCC(CCCOc3cc(F)c(C4=NC[C@@H](CO)O4)c(F)c3)CC2)nc1] | (S)-(2-(4-(3-(1-(5-ethylpyrimidin-2-yl)piperidin-4-yl)propoxy)-2,6-difluorophenyl)-4,5-dihydrooxazol-5-yl)methanol | 461.2 |
| 9 | 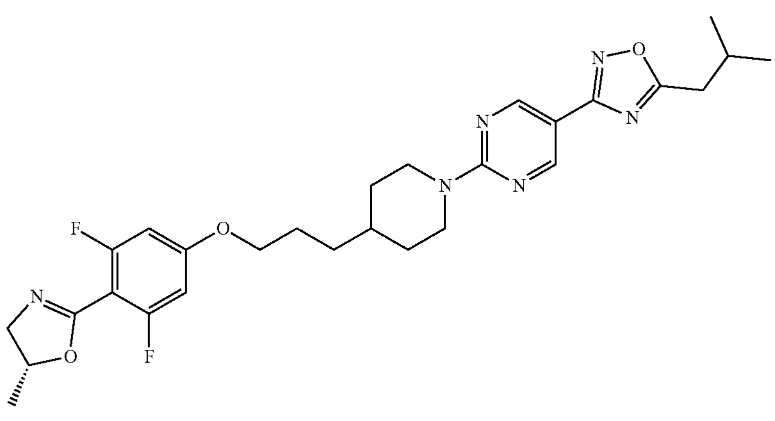 [SMILES: CC(C)Cc1nc(-c2cnc(N3CCC(CCCOc4cc(F)c(C5=NC[C@@H](C)O5)c(F)c4)CC3)nc2)no1] | (R)-3-(2-(4-(3-(3,5-difluoro-4-(5-methyl-4,5-dihydrooxazol-2-yl)phenoxy)propyl)piperidin-1-yl)pyrimidin-5-yl)-5-isobuty-1,2,4-oxadiazole | 541.3 |
| 10 | 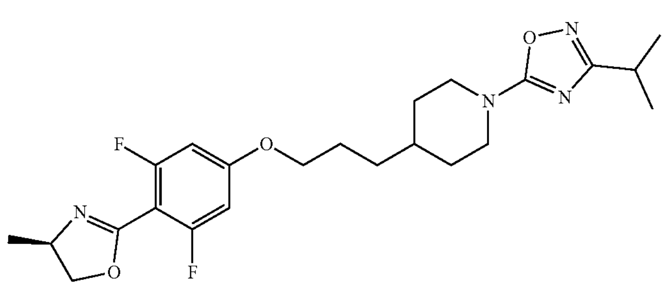 [SMILES: CC(C)c1noc(N2CCC(CCCOc3cc(F)c(C4=N[C@H](C)CO4)c(F)c3)CC2)n1] | (R)-5-(4-(3-(3,5-difluoro-4-(4-methyl-4,5-dihydrooxazol-2-yl)phenoxy)propyl)piperidin-1-yl)-3-isopropyl-1,2,4-oxadiazole | 449.2 |

TABLE 1-continued

| No. of Example | Chemical structure | Chemical name | Mass [M + 1]+ |
|---|---|---|---|
| 11 | 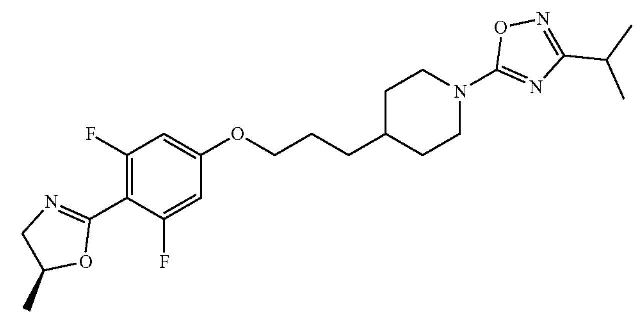 [SMILES: CC(C)c1noc(N2CCC(CCCOc3cc(F)c(C4=NC[C@H](C)O4)c(F)c3)CC2)n1] | (S)-5-(4-(3-(3,5-difluoro-4-(5-methyl-4,5-dihydrooxazol-2-yl)phenoxy)propyl)piperidin-1-yl)-3-isopropyl-1,2,4-oxadiazole | 449.2 |
| 12 | 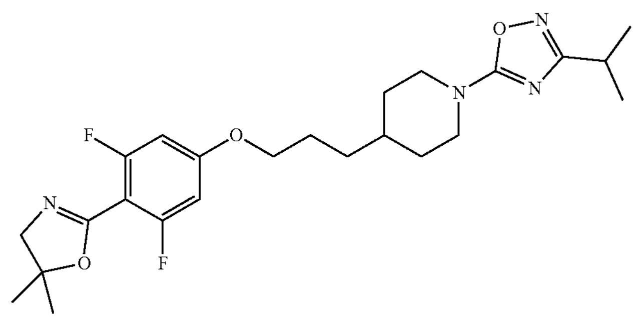 [SMILES: CC(C)c1noc(N2CCC(CCCOc3cc(F)c(C4=NCC(C)(C)O4)c(F)c3)CC2)n1] | 5-(4-(3-(4-(5,5-dimethyl-4,5-dihydrooxazol-2-yl)-3,5-difluoro phenoxy)propyl)piperidin-1-yl)-3-isopropyl-1,2,4-oxadiazole | 463.2 |
| 13 | 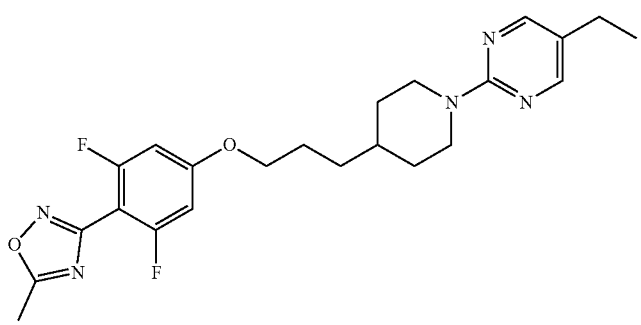 [SMILES: CCc1cnc(N2CCC(CCCOc3cc(F)c(-c4noc(C)n4)c(F)c3)CC2)nc1] | 3-(4-(3-(1-(5-ethylpyrimidin-2-yl)piperidin-4-yl)propoxy)-2,6-difluorophenyl)-5-methyl-1,2,4-oxadiazole | 444.2 |
| 14 | 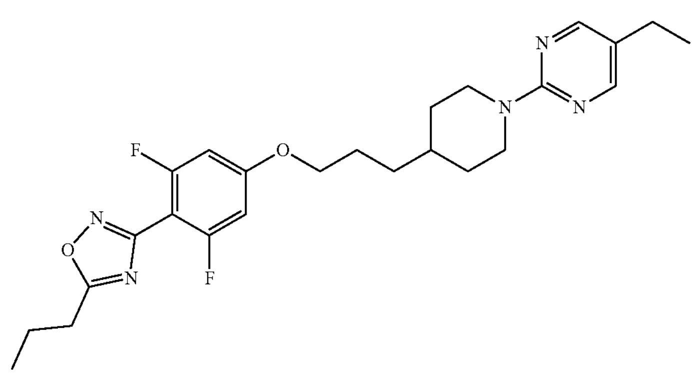 [SMILES: CCCc1nc(-c2c(F)cc(OCCCC3CCN(c4ncc(CC)cn4)CC3)cc2F)no1] | 3-(4-(3-(1-(5-ethylpyrimidin-2-yl)piperidin-4-yl)propoxy)-2,6-difluorophenyl)-5-propyl-1,2,4-oxadiazole | 472.2 |

TABLE 1-continued

| No. of Example | Chemical structure | Chemical name | Mass [M + 1]+ |
|---|---|---|---|
| 15 | 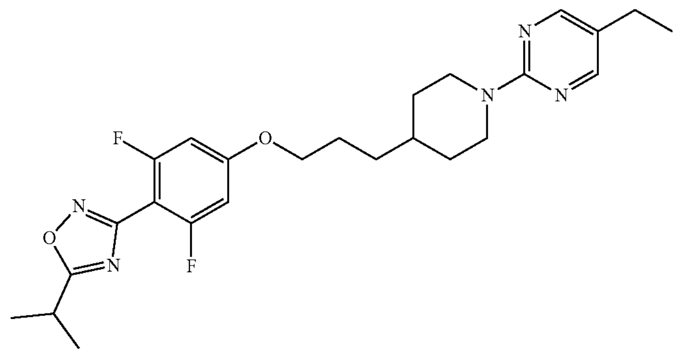 [SMILES: CCc1cnc(N2CCC(CCCOc3cc(F)c(-c4noc(C(C)C)n4)c(F)c3)CC2)nc1] | 3-(4-(3-(1-(5-ethylpyrimidin-2-yl)piperidin-4-yl)propoxy)-2,6-difluorophenyl)-5-isopropyl-1,2,4-oxadiazole | 472.2 |
| 16 | 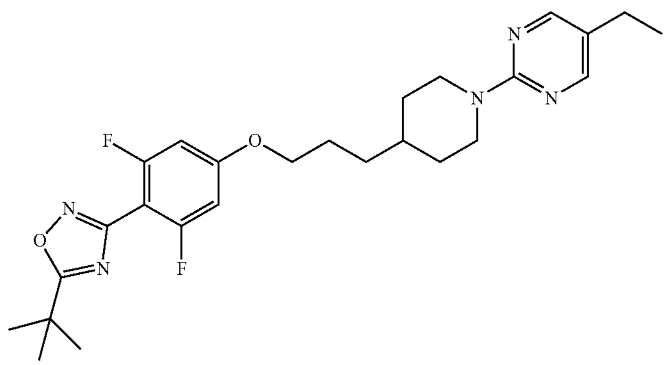 [SMILES: CCc1cnc(N2CCC(CCCOc3cc(F)c(-c4noc(C(C)(C)C)n4)c(F)c3)CC2)nc1] | 5-(tert-butyl)-3-(4-(3-(1-(5-ethylpyrimidin-2-yl)piperidin-4-yl)propoxy)-2,6-difluorophenyl)-1,2,4-oxadiazole | 486.3 |
| 17 | 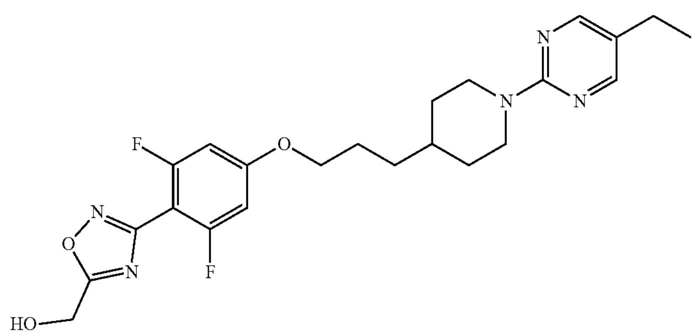 [SMILES: CCc1cnc(N2CCC(CCCOc3cc(F)c(-c4noc(CO)n4)c(F)c3)CC2)nc1] | (3-(4-(3-(1-(5-ethylpyrimidin-2-yl)piperidin-4-yl)propoxy)-2,6-difluorophenyl)-1,2,4-oxadiazol-5-yl)methanol | 460.2 |
| 18 | 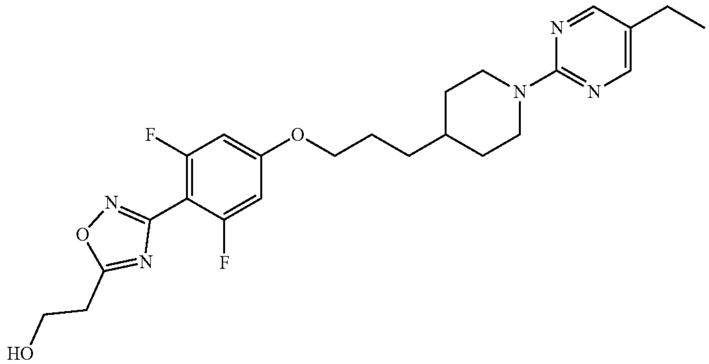 [SMILES: CCc1cnc(N2CCC(CCCOc3cc(F)c(-c4noc(CCO)n4)c(F)c3)CC2)nc1] | 2-(3-(4-(3-(1-(5-ethylpyrimidin-2-yl)piperidin-4-yl)propoxy)-2,6-difluorophenyl)-1,2,4-oxadiazol-5-yl)ethan-1-ol | 474.2 |

TABLE 1-continued

| No. of Example | Chemical structure | Chemical name | Mass [M + 1]+ |
|---|---|---|---|
| 19 | 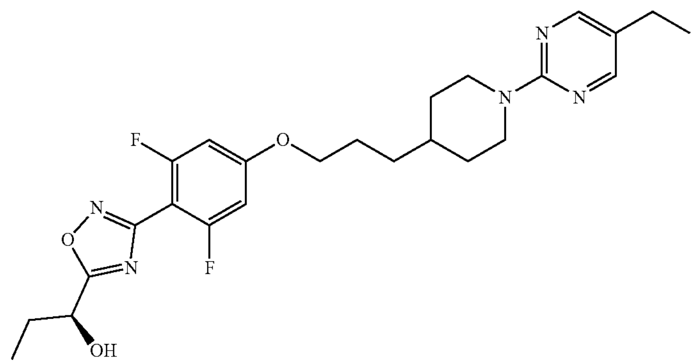 [SMILES: CCc1cnc(N2CCC(CCCOc3cc(F)c(-c4noc([C@@H](O)CC)n4)c(F)c3)CC2)nc1] | (S)-1-(3-(4-(3-(1-(5-ethylpyrimidin-2-yl)piperidin-4-yl)propoxy)-2,6-difluorophenyl)-1,2,4-oxadiazol-5-yl)propan-1-ol | 488.2 |
| 20 | 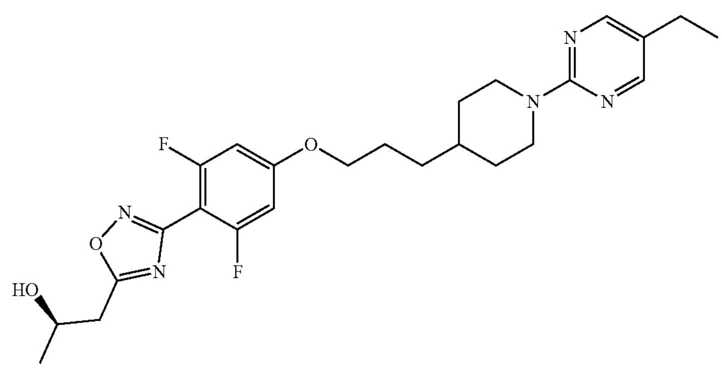 [SMILES: CCc1cnc(N2CCC(CCCOc3cc(F)c(-c4noc(C[C@@H](C)O)n4)c(F)c3)CC2)nc1] | (R)-1-(3-(4-(3-(1-(5-ethylpyrimidin-2-yl)piperidin-4-yl)propoxy)-2,6-difluorophenyl)-1,2,4-oxadiazol-5-yl)propan-2-ol | 488.2 |
| 21 | 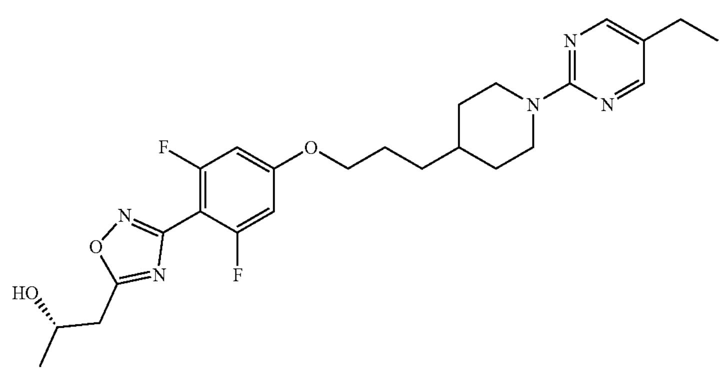 [SMILES: CCc1cnc(N2CCC(CCCOc3cc(F)c(-c4noc(C[C@H](C)O)n4)c(F)c3)CC2)nc1] | (S)-1-(3-(4-(3-(1-(5-ethylpyrimidin-2-yl)piperidin-4-yl)propoxyl)-2,6-difluorophenyl)-1,2,4-oxadiazol-5-yl)propan-2-ol | 488.2 |
| 22 | 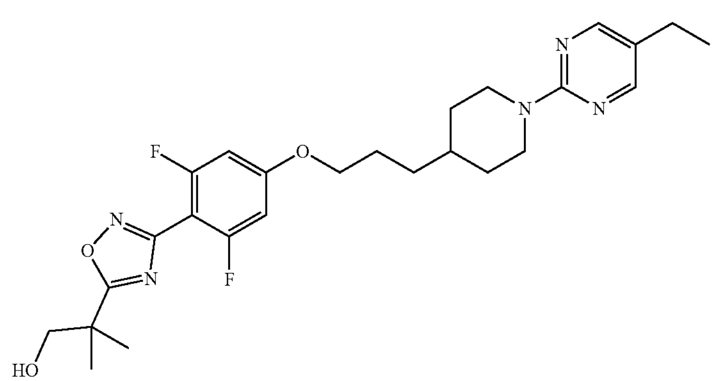 [SMILES: CCc1cnc(N2CCC(CCCOc3cc(F)c(-c4noc(C(C)(C)CO)n4)c(F)c3)CC2)nc1] | 2-(3-(4-(3-(1-(5-ethylpyrimidin-2-yl)piperidin-4-yl)propoxy)-2,6-difluorophenyl)-1,2,4-oxadiazol-5-yl)-2-methylpropan-1-ol | 502.3 |

TABLE 1-continued

| No. of Example | Chemical structure | Chemical name | Mass [M + 1]+ |
|---|---|---|---|
| 23 | 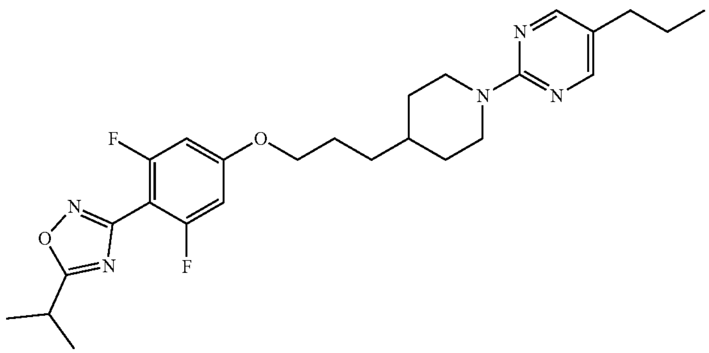 [SMILES: CCCc1cnc(N2CCC(CCCOc3cc(F)c(-c4noc(C(C)C)n4)c(F)c3)CC2)nc1] | 3-(2,6-difluoro-4-(3-(1-(5-propylpyrimidin-2-yl)piperidin-4-yl)propoxy)phenyl)-5-isopropyl-1,2,4-oxadiazole | 486.3 |
| 24 | 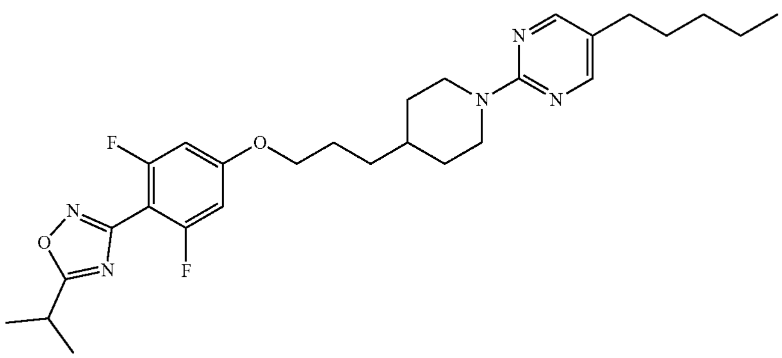 [SMILES: CCCCCc1cnc(N2CCC(CCCOc3cc(F)c(-c4noc(C(C)C)n4)c(F)c3)CC2)nc1] | 3-(2,6-difluoro-4-(3-(1-(5-pentylpyrimidin-2-yl)piperidin-4-yl)propoxy)phenyl)-5-isopropyl-1,2,4-oxadiazole | 514.3 |
| 25 | 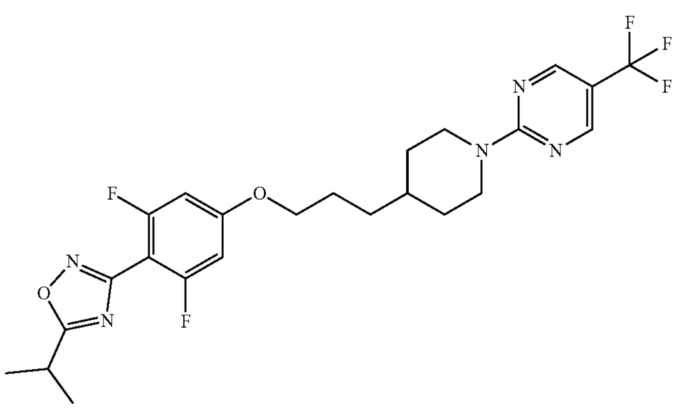 [SMILES: CC(C)c1nc(-c2c(F)cc(OCCCC3CCN(c4ncc(C(F)(F)F)cn4)CC3)cc2F)no1] | 3-(2,6-difluoro-4-(3-(1-(5-(trifluoromethyl)pyrimidin-2-yl)piperidin-4-yl)propoxy)phenyl)-5-isopropyl-1,2,4-oxadiazole | 512.2 |
| 26 | 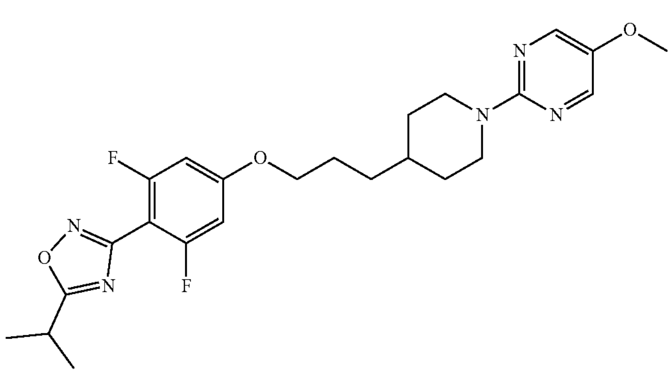 [SMILES: COc1cnc(N2CCC(CCCOc3cc(F)c(-c4noc(C(C)C)n4)c(F)c3)CC2)nc1] | 3-(2,6-difluoro-4-(3-(1-(5-methoxypyrimidin-2-yl)piperidin-4-yl)propoxy)phenyl)-5-isopropyl-1,2,4-oxadiazole | 474.2 |

TABLE 1-continued

| No. of Example | Chemical structure | Chemical name | Mass [M + 1]⁺ |
|---|---|---|---|
| 27 | 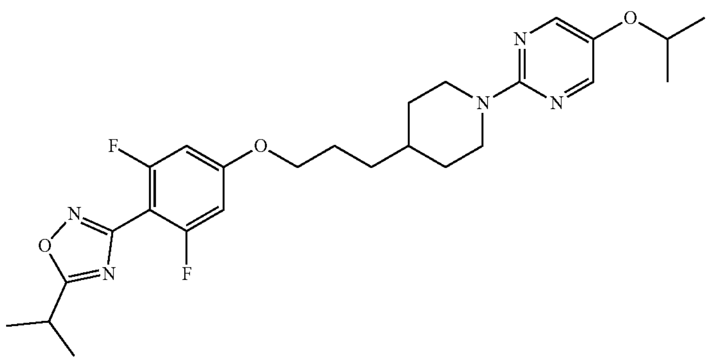 [SMILES: CC(C)Oc1cnc(N2CCC(CCCOc3cc(F)c(-c4noc(C(C)C)n4)c(F)c3)CC2)nc1] | 3-(2,6-difluoro-4-(3-(1-(5-isopropoxypyrimidin-2-yl)piperidin-4-yl)propoxy)phenyl)-5-isopropyl-1,2,4-oxadiazole | 502.3 |
| 28 | 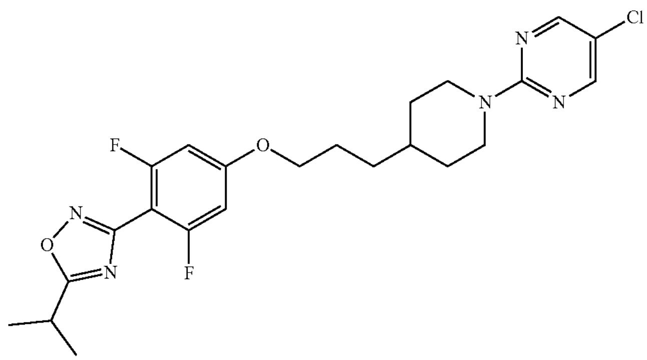 [SMILES: CC(C)c1nc(-c2c(F)cc(OCCCC3CCN(c4ncc(Cl)cn4)CC3)cc2F)no1] | 3-(4-(3-(1-(5-chloropyrimidin-2-yl)piperidin-4-yl)propoxy)-2,6-difluorophenyl)-5-isopropyl-1,2,4-oxadiazole | 478.2 |
| 29 | 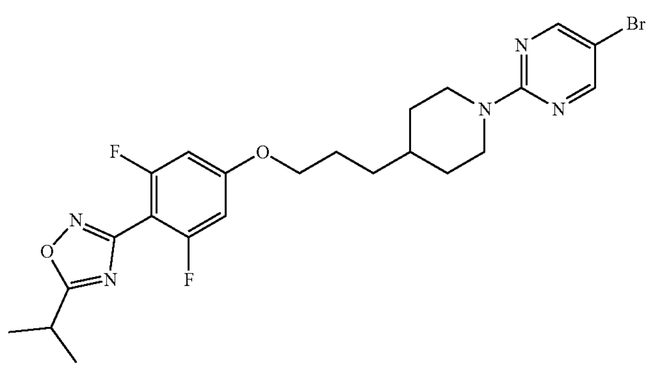 [SMILES: CC(C)c1nc(-c2c(F)cc(OCCCC3CCN(c4ncc(Br)cn4)CC3)cc2F)no1] | 3-(4-(3-(1-(5-bromopyrimidin-2-yl)piperidin-4-yl)propoxy)-2,6-difluorophenyl)-5-isopropyl-1,2,4-oxadiazole | 522.1 |
| 30 | 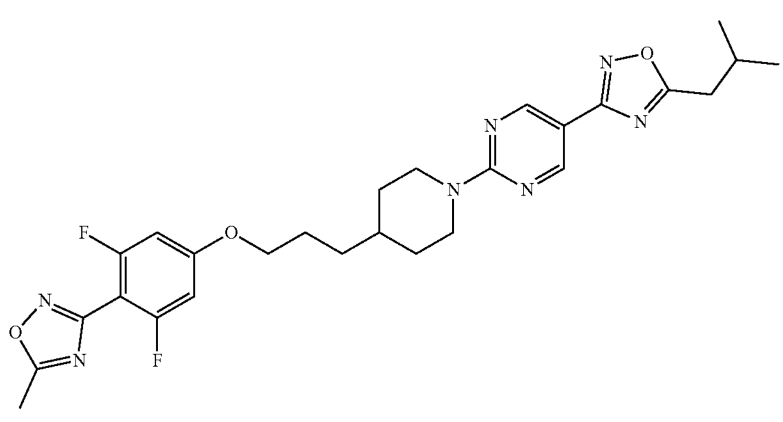 [SMILES: Cc1nc(-c2c(F)cc(OCCCC3CCN(c4ncc(-c5noc(CC(C)C)n5)cn4)CC3)cc2F)no1] | 3-(2,6-difluoro-4-(3-(1-(5-(5-isobutyl-1,2,4-oxadiazol-3-yl)pyrimidin-2-yl)piperidin-4-yl)propoxy)phenyl)-5-methyl-1,2,4-oxadiazole | 540.3 |

TABLE 1-continued

| No. of Example | Chemical structure | Chemical name | Mass [M + 1]+ |
|---|---|---|---|
| 31 | 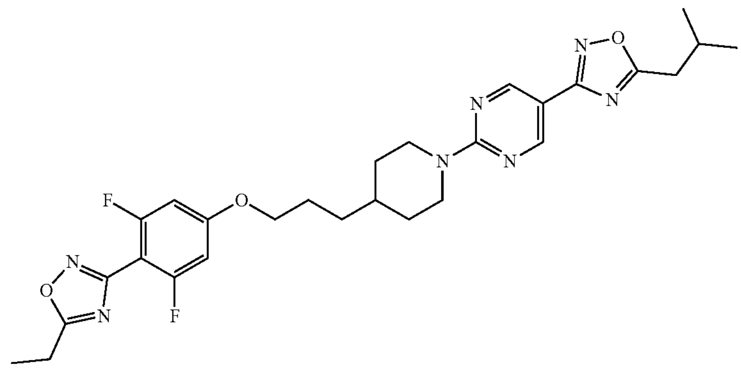 [SMILES: CCc1nc(-c2c(F)cc(OCCCC3CCN(c4ncc(-c5noc(CC(C)C)n5)cn4)CC3)cc2F)no1] | 3-(2,6-difluoro-4-(3-(1-(5-(5-isobutyl-1,2,4-oxadiazol-3-yl)pyrimidin-2-yl)piperidin-4-yl)propoxy)phenyl)-5-ethyl-1,2,4-oxadiazole | 554.3 |
| 32 | 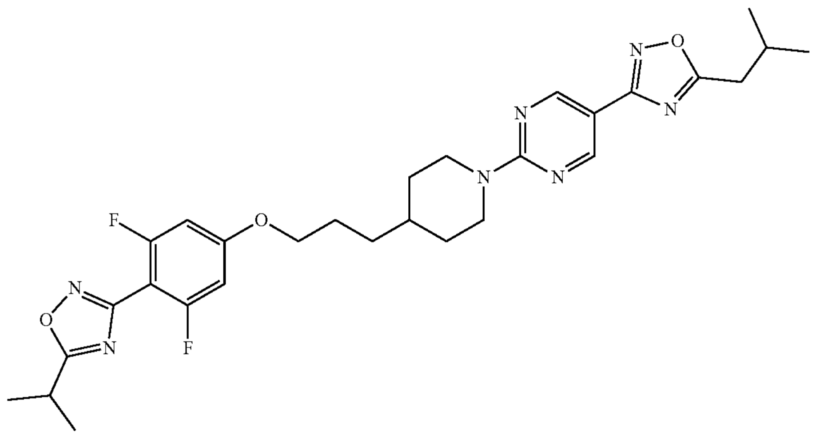 [SMILES: CC(C)Cc1nc(-c2cnc(N3CCC(CCCOc4cc(F)c(-c5noc(C(C)C)n5)c(F)c4)CC3)nc2)no1] | 3-(2,6-difluoro-4-(3-(1-(5-(5-isobutyl-1,2,4-oxadiazol-3-yl)pyrimidin-2-yl)piperidin-4-yl)propoxy)phenyl)-5-isopropyl-1,2,4-oxadiazole | 568.3 |
| 33 | 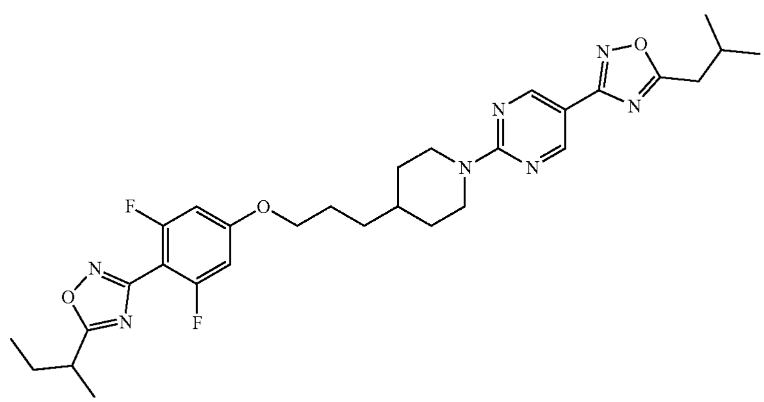 [SMILES: CCC(C)c1nc(-c2c(F)cc(OCCCC3CCN(c4ncc(-c5noc(CC(C)C)n5)cn4)CC3)cc2F)no1] | 5-(sec-butyl)-3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazole | 582.3 |
| 34 | 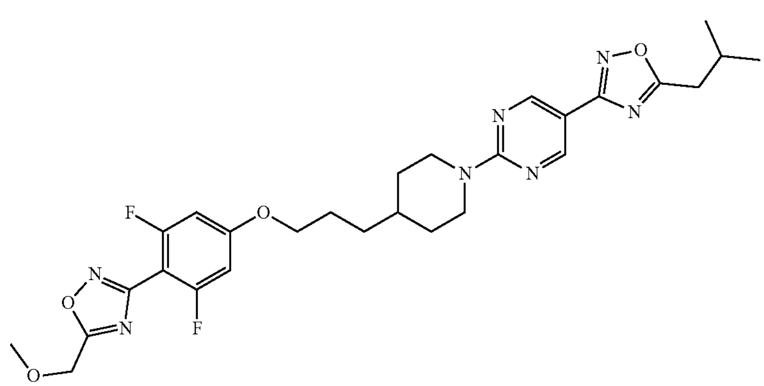 [SMILES: COCc1nc(-c2c(F)cc(OCCCC3CCN(c4ncc(-c5noc(CC(C)C)n5)cn4)CC3)cc2F)no1] | 3-(2,6-difluoro-4-(3-(1-(5-(5-isobutyl-1,2,4-oxadiazol-3-yl)pyrimidin-2-yl)piperidin-4-yl)propoxy)phenyl)-5-(methoxymethyl)-1,2,4-oxadiazole | 570.3 |

TABLE 1-continued

| No. of Example | Chemical structure | Chemical name | Mass [M + 1]+ |
|---|---|---|---|
| 35 | 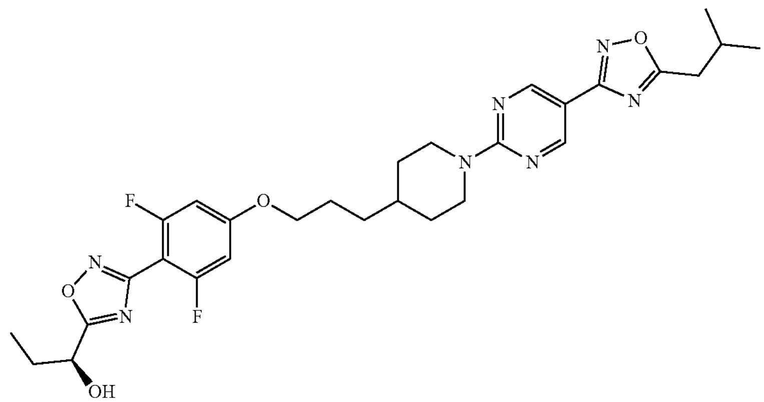 [SMILES: CC[C@H](O)c1nc(-c2c(F)cc(OCCCC3CCN(c4ncc(-c5noc(CC(C)C)n5)cn4)CC3)cc2F)no1] | (S)-1-(3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazol-5-yl)propan-1-ol | 584.3 |
| 36 | 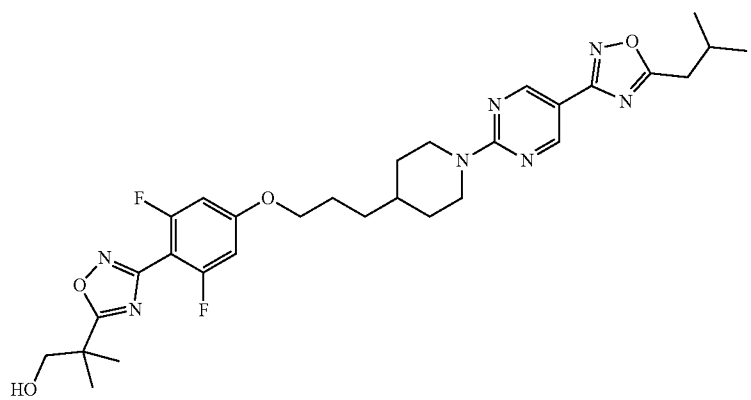 [SMILES: CC(C)Cc1nc(-c2cnc(N3CCC(CCCOc4cc(F)c(-c5noc(C(C)(C)CO)n5)c(F)c4)CC3)nc2)no1] | 2-(3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazol-5-yl)-2-methylpropan-1-ol | 598.3 |
| 37 | 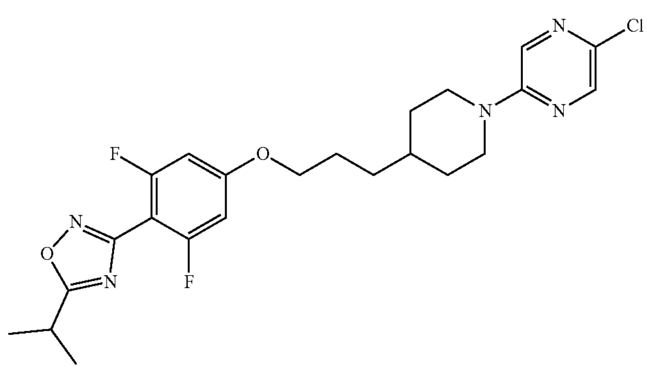 [SMILES: CC(C)c1nc(-c2c(F)cc(OCCCC3CCN(c4cnc(Cl)cn4)CC3)cc2F)no1] | 3-(4-(3-(1-(5-chloropyrazin-2-yl)piperidin-4-yl)propoxy)-2,6-difluorophenyl)-5-isopropyl-1,2,4-oxadiazole | 478.2 |
| 38 | 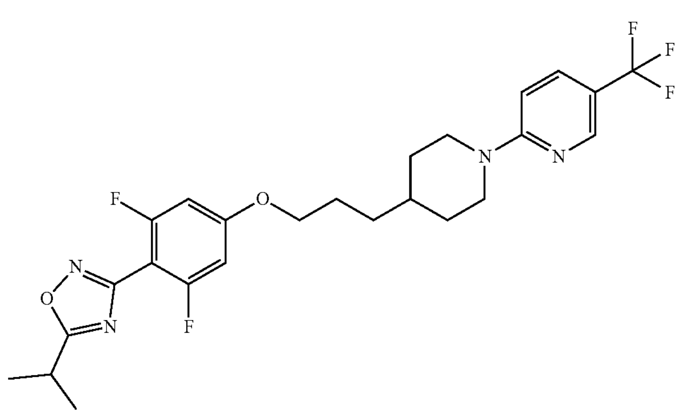 [SMILES: CC(C)c1nc(-c2c(F)cc(OCCCC3CCN(c4ccc(C(F)(F)F)cn4)CC3)cc2F)no1] | 3-(2,6-difluoro-4-(3-(1-(5-(trifluoromethyl)pyridin-2-yl)piperidin-4-yl)propoxy)phenyl)-5-isopropyl-1,2,4-oxadiazole | 511.2 |

TABLE 1-continued

| No. of Example | Chemical structure | Chemical name | Mass [M + 1]⁺ |
|---|---|---|---|
| 39 | 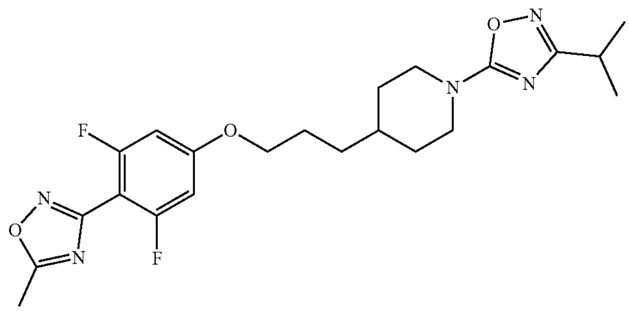 [SMILES: Cc1nc(-c2c(F)cc(OCCCC3CCN(c4nc(C(C)C)no4)CC3)cc2F)no1] | 3-(2,6-difluoro-4-(3-(1-(3-isopropyl-1,2,4-oxadiazol-5-yl)piperidin-4-yl)propoxy)phenyl)-5-methyl-1,2,4-oxadiazole | 448.2 |
| 40 | 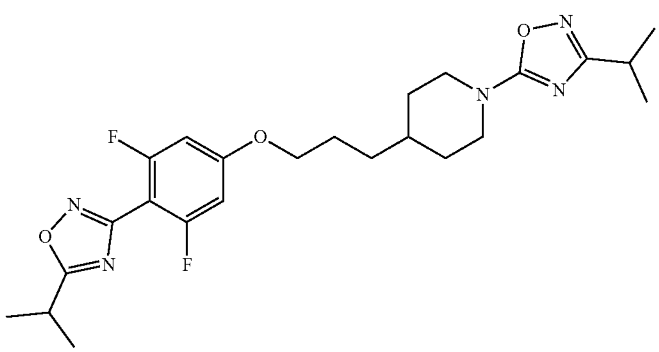 [SMILES: CC(C)c1noc(N2CCC(CCCOc3cc(F)c(-c4noc(C(C)C)n4)c(F)c3)CC2)n1] | 3-(2,6-difluoro-4-(3-(1-(3-isopropyl-1,2,4-oxadiazol-5-yl)piperidin-4-yl)propoxy)phenyl)-5-isopropyl-1,2,4-oxadiazole | 476.2 |
| 41 | 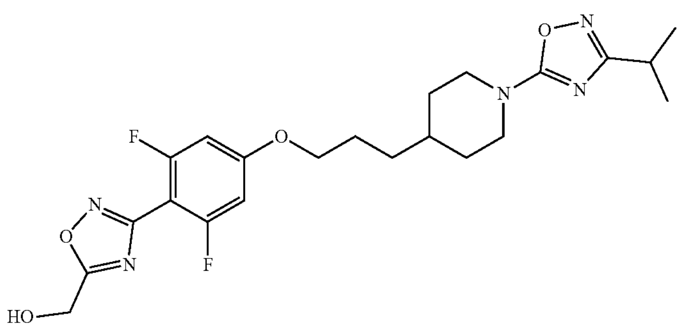 [SMILES: CC(C)c1noc(N2CCC(CCCOc3cc(F)c(-c4noc(CO)n4)c(F)c3)CC2)n1] | (3-(2,6-difluoro-4-(3-(1-(3-isopropyl-1,2,4-oxadiazol-5-yl)piperidin-4-yl)propoxy)phenyl)-1,2,4-oxadiazol-5-yl)methanol | 464.2 |
| 42 | 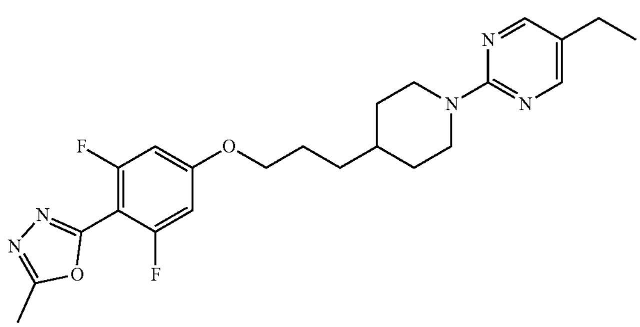 [SMILES: CCc1cnc(N2CCC(CCCOc3cc(F)c(-c4nnc(C)o4)c(F)c3)CC2)nc1] | 2-(4-(3-(1-(5-ethylpyrimidin-2-yl)piperidin-4-yl)propoxy)-2,6-difluorophenyl)-5-methyl-1,3,4-oxadiazole | 444.2 |

TABLE 1-continued

| No. of Example | Chemical structure | Chemical name | Mass [M + 1]+ |
|---|---|---|---|
| 43 | 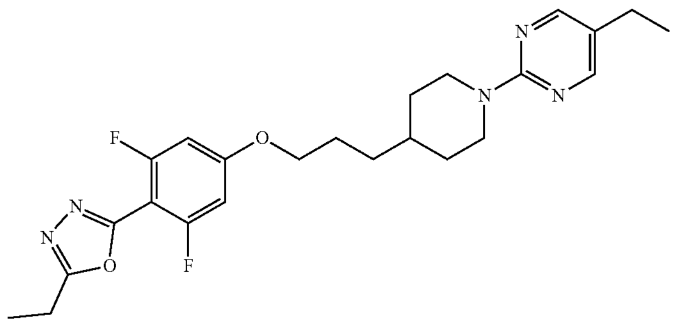 [SMILES: CCc1cnc(N2CCC(CCCOc3cc(F)c(-c4nnc(CC)o4)c(F)c3)CC2)nc1] | 2-ethyl-5-(4-(3-(1-(5-ethylpyrimidin-2-yl)piperidin-4-yl)propoxy)-2,6-difluorophenyl)-1,3,4-oxadiazole | 458.2 |
| 44 | 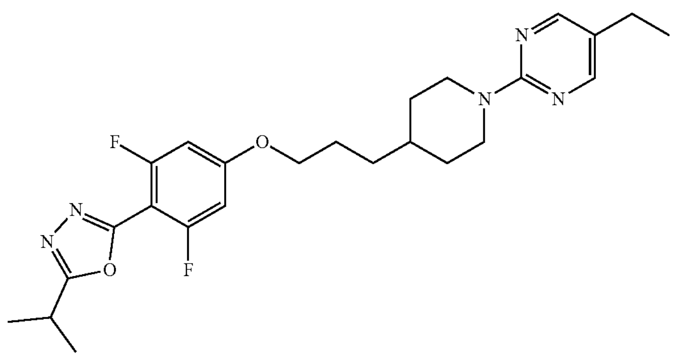 | 2-(4-(3-(1-(5-ethylpyrimidin-2-yl)piperidin-4-yl)propoxy)-2,6-difluorophenyl)-5-isopropyl-1,3,4-oxadiazole | 472.2 |
| 45 | 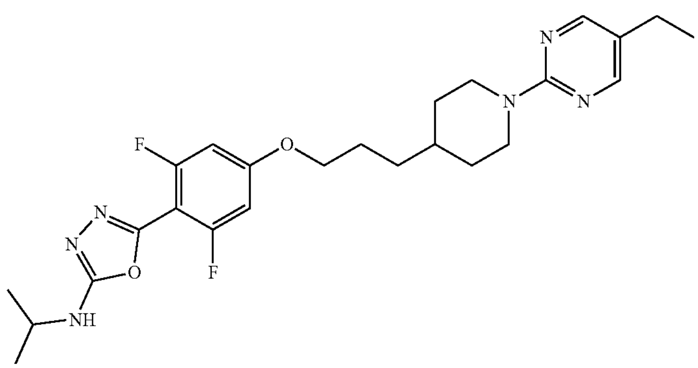 [SMILES: CCc1cnc(N2CCC(CCCOc3cc(F)c(-c4nnc(NC(C)C)o4)c(F)c3)CC2)nc1] | 5-(4-(3-(1-(5-ethylpyrimidin-2-yl)piperidin-4-yl)propoxy)-2,6-difluorophenyl)-N-isopropyl-1,3,4-oxadiazol-2-amine | 488.2 |
| 46 | 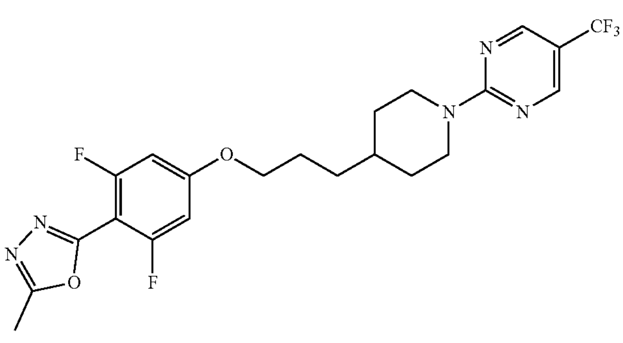 [SMILES: Cc1nnc(-c2c(F)cc(OCCCC3CCN(c4ncc(C(F)(F)F)cn4)CC3)cc2F)o1] | 2-(2,6-difluoro-4-(3-(1-(5-(trifluoromethyl)pyrimidin-2-yl)piperidin-4-yl)propoxy)phenyl)-5-methyl-1,3,4-oxadiazole | 484.2 |

TABLE 1-continued

| No. of Example | Chemical name | Mass [M + 1]+ |
|---|---|---|
| 47 | 2-(2,6-difluoro-4-(3-(1-(5-(trifluoromethyl)pyrimidin-2-yl)piperidin-4-yl)propoxy)phenyl)-5-ethyl-1,3,4-oxadiazole | 498.2 |
| 48 | 2-(2,6-difluoro-4-(3-(1-(5-(trifluoromethyl)pyrimidin-2-yl)piperidin-4-yl)propoxy)phenyl)-5-isopropyl-1,3,4-oxadiazole | 512.2 |
| 49 | 2-(4-(3-(1-(5-chloropyrazin-2-yl)piperidin-4-yl)propoxy)-2,6-difluorophenyl)-5-methyl-1,3,4-oxadiazole | 450.1 |
| 50 | 2-(4-(3-(1-(5-chloropyrazin-2-yl)piperidin-4-yl)propoxy)-2,6-difluorophenyl)-5-ethyl-1,3,4-oxadiazole | 464.2 |

TABLE 1-continued

| No. of Example | Chemical structure | Chemical name | Mass [M + 1]+ |
|---|---|---|---|
| 51 | 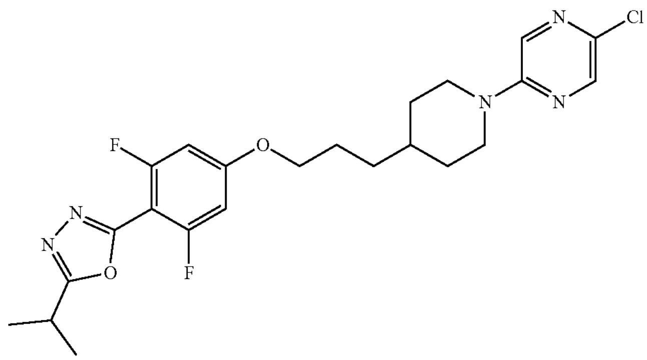 [SMILES: CC(C)c1nnc(-c2c(F)cc(OCCCC3CCN(c4cnc(Cl)cn4)CC3)cc2F)o1] | 2-(4-(3-(1-(5-chloropyrazin-2-yl)piperidin-4-yl)propoxy)-2,6-difluorophenyl)-5-isopropyl-1,3,4-oxadiazole | 478.2 |
| 52 | 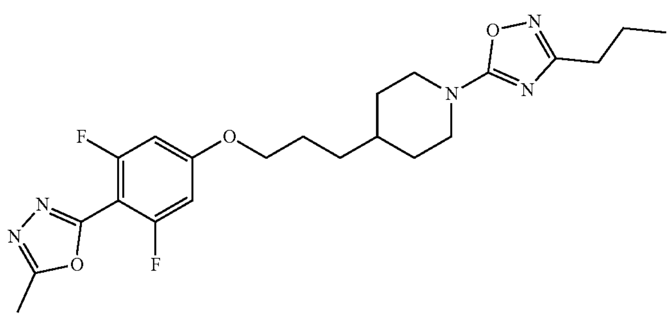 [SMILES: CCCc1noc(N2CCC(CCCOc3cc(F)c(-c4nnc(C)o4)c(F)c3)CC2)n1] | 5-(4-(3-(3,5-difluoro-4-(5-methyl-1,3,4-oxadiazol-2-yl)phenoxy)propyl)piperidin-1-yl)-3-propyl-1,2,4-oxadiazole | 448.2 |
| 53 | 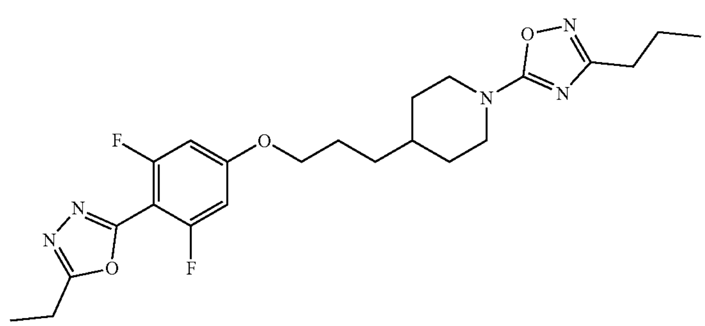 [SMILES: CCCc1noc(N2CCC(CCCOc3cc(F)c(-c4nnc(CC)o4)c(F)c3)CC2)n1] | 5-(4-(3-(3,5-difluoro-4-(5-ethyl-1,3,4-oxadiazol-2-yl)phenoxy)propyl)piperidin-1-yl)-3-propyl-1,2,4-oxadiazole | 462.2 |
| 54 | 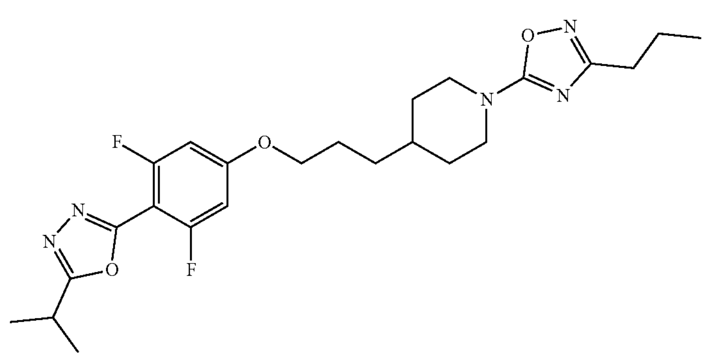 [SMILES: CCCc1noc(N2CCC(CCCOc3cc(F)c(-c4nnc(C(C)C)o4)c(F)c3)CC2)n1] | 5-(4-(3-(3,5-difluoro-4-(5-isopropyl-1,3,4-oxadiazol-2-yl)phenoxy)propyl)piperidin-1-yl)-3-propyl-1,2,4-oxadiazole | 476.2 |

TABLE 1-continued

| No. of Example | Chemical structure | Chemical name | Mass [M + 1]+ |
|---|---|---|---|
| 55 | 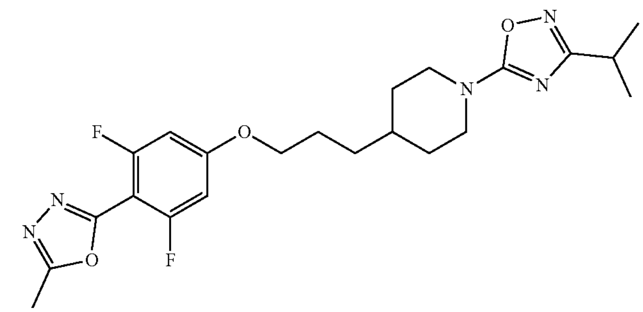 [SMILES: Cc1nnc(-c2c(F)cc(OCCCC3CCN(c4nc(C(C)C)no4)CC3)cc2F)o1] | 5-(4-(3-(3,5-difluoro-4-(5-methyl-1,3,4-oxadiazol-2-yl)phenoxy)propyl)piperidin-1-yl)-3-isopropyl-1,2,4-oxadiazole | 448.2 |
| 56 | 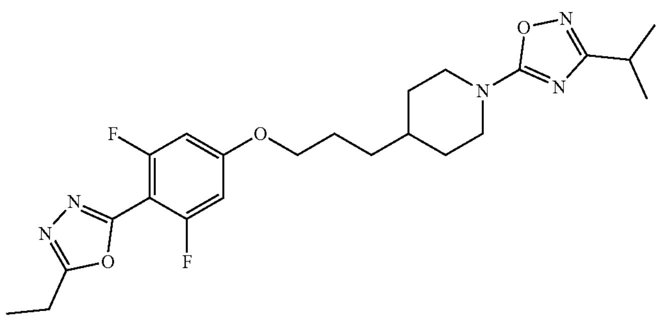 [SMILES: CCc1nnc(-c2c(F)cc(OCCCC3CCN(c4nc(C(C)C)no4)CC3)cc2F)o1] | 5-(4-(3-(4-(5-ethyl-1,3,4-oxadiazol-2-yl)-3,5-difluorophenoxy)propyl)piperidin-1-yl)-3-isopropyl-1,2,4-oxadiazole | 462.2 |
| 57 | 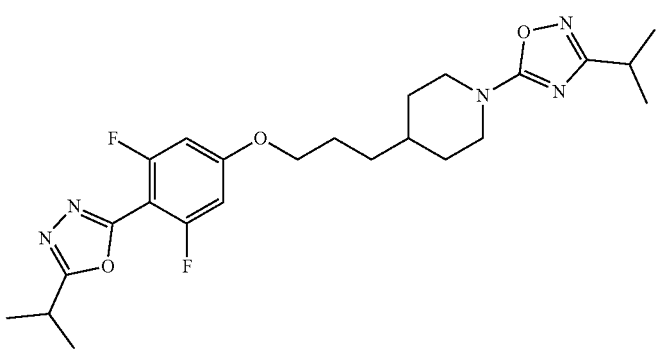 [SMILES: CC(C)c1noc(N2CCC(CCCOc3cc(F)c(-c4nnc(C(C)C)o4)c(F)c3)CC2)n1] | 5-(4-(3-(3,5-difluoro-4-(5-isopropyl-1,3,4-oxadiazol-2-yl)phenoxy)propyl)piperidin-1-yl)-3-isopropyl-1,2,4-oxadiazole | 476.2 |
| 58 | 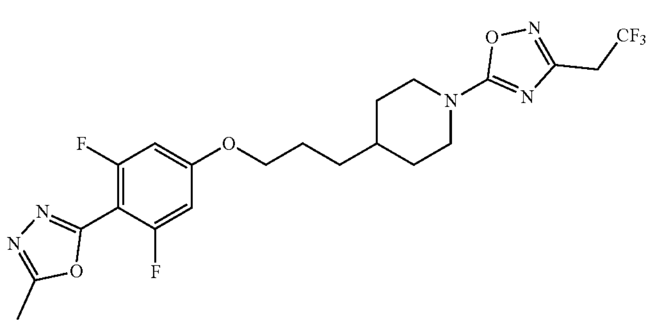 [SMILES: Cc1nnc(-c2c(F)cc(OCCCC3CCN(c4nc(CC(F)(F)F)no4)CC3)cc2F)o1] | 5-(4-(3-(3,5-difluoro-4-(5-methyl-1,3,4-oxadiazol-2-yl)phenoxy)propyl)piperidin-1-yl)-3-(2,2,2-trifluoroethyl)-1,2,4-oxadiazole | 488.1 |

TABLE 1-continued

| No. of Example | Chemical structure | Chemical name | Mass [M + 1]+ |
|---|---|---|---|
| 59 | 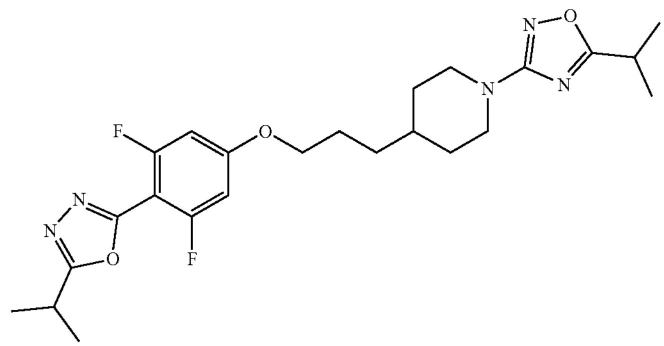 [SMILES: CC(C)c1nc(N2CCC(CCCOc3cc(F)c(-c4nnc(C(C)C)o4)c(F)c3)CC2)no1] | 3-(4-(3-(3,5-difluoro-4-(5-isopropyl-1,3,4-oxadiazol-2-yl)phenoxy)propyl)piperidin-1-yl)-5-isopropyl-1,2,4-oxadiazole | 498.2 |
| 60 | 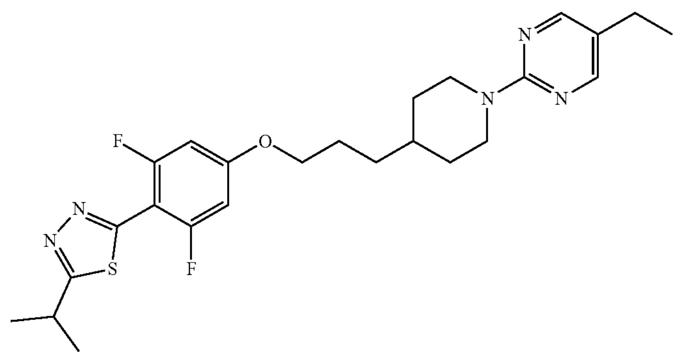 [SMILES: CCc1cnc(N2CCC(CCCOc3cc(F)c(-c4nnc(C(C)C)s4)c(F)c3)CC2)nc1] | 2-(4-(3-(1-(5-ethylpyrimidin-2-yl)piperidin-4-yl)propoxy)-2,6-difluorophenyl)-5-isopropyl-1,3,4-thiadiazole | 488.3 |
| 61 | 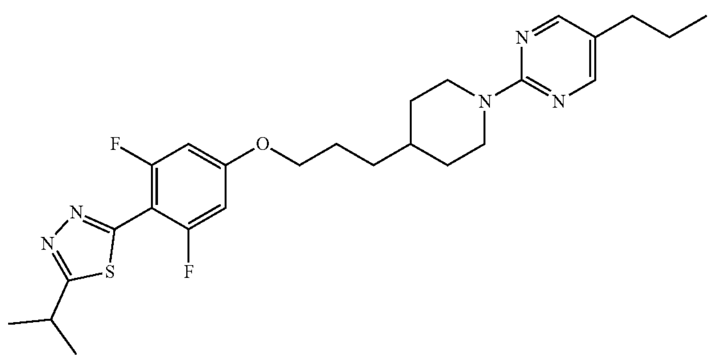 [SMILES: CCCc1cnc(N2CCC(CCCOc3cc(F)c(-c4nnc(C(C)C)s4)c(F)c3)CC2)nc1] | 2-(2,6-difluoro-4-(3-(1-(5-propylpyrimidin-2-yl)piperidin-4-yl)propoxy)phenyl)-5-isopropyl-1,3,4-thiadiazole | 502.3 |
| 62 | 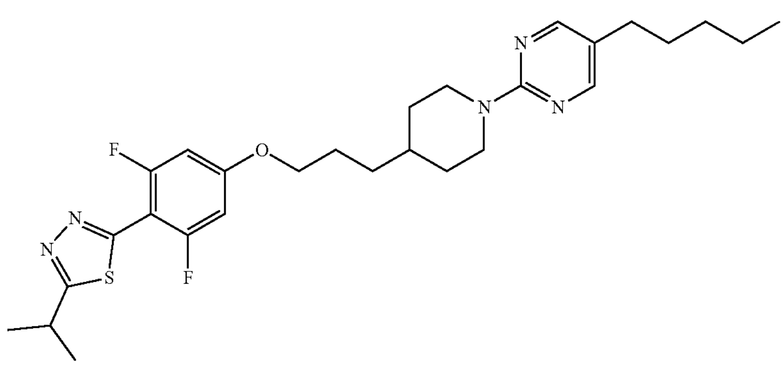 [SMILES: CCCCCc1cnc(N2CCC(CCCOc3cc(F)c(-c4nnc(C(C)C)s4)c(F)c3)CC2)nc1] | 2-(2,6-difluoro-4-(3-(1-(5-pentylpyrimidin-2-yl)piperidin-4-yl)propoxy)phenyl)-5-isopropyl-1,3,4-thiadiazole | 530.3 |

TABLE 1-continued

| No. of Example | Chemical structure | Chemical name | Mass [M + 1]+ |
|---|---|---|---|
| 63 | 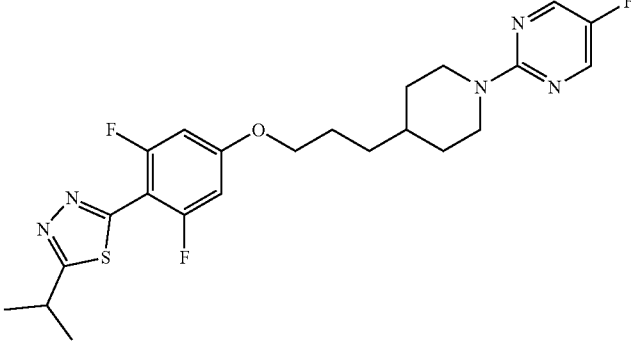 | 2-(2,6-difluoro-4-(3-(1-(5-fluoropyrimidin-2-yl)piperidin-4-yl)propoxy)phenyl)-5-isopropyl-1,3,4-thiadiazole | 478.2 |
| 64 | 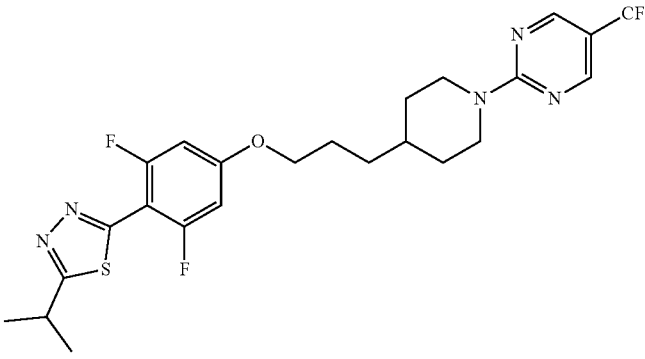 | 2-(2,6-difluoro-4-(3-(1-(5-(trifluoromethyl)pyrimidin-2-yl)piperidin-4-yl)propoxy)phenyl)-5-isopropyl-1,3,4-thiadiazole | 582.2 |
| 65 | 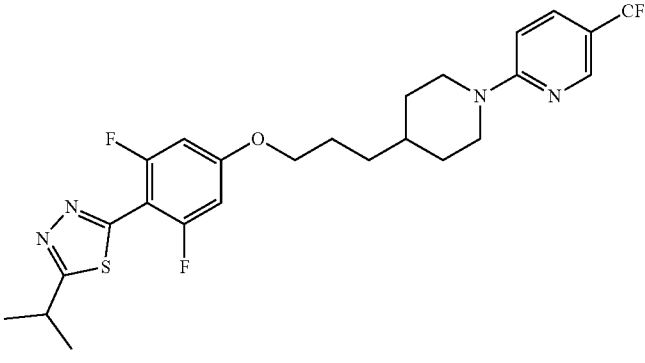 | 2-(2,6-difluoro-4-(3-(1-(5-(trifluoromethyl)pyridin-2-yl)piperidin-4-yl)propoxy)phenyl)-5-isopropyl-1,3,4-thiadiazole | 527.2 |
| 66 | 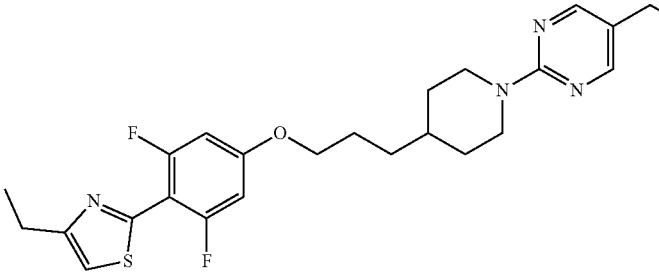 | 4-ethyl-2-(4-(3-(1-(5-ethylpyrimidin-2-yl)piperidin-4-yl)propoxy)-2,6-difluorophenyl)thiazole | 473.2 |

<Experimental Example 1>Human GPR119 activation assay

Human GPR119 was temporarily expressed on cells, thereby quantifying the amount of cyclic adenosine 3',5'-monophosphate (cAMP) increased upon activating GPR119 by the compound of the present invention, using the product from Cysbio, by a method of HTRF (homogeneous time resolved fluorescence), and such quantification was used to refer to efficacy on GPR119 activation.

Human GPR119 expression vector (Origene) was overexpressed in hamster renal epithelial cells (HEK293) (ATCC), and the cells were stabilized for 48 hours. With a solution of 11.1 mM glucose, 0.1% bovine serum albumin, and 0.5 mM IBMX (3-isobutyl-1-methylxanthine) which is a phosphodiesterase inhibitor being added to a KRBH (Krebs-Ringer Bicarbonate HEPES; Hou ZQ. et al., Mol Cell Endocrinol, 2008(291):71-78) buffer, the cells were pre-treated for 10 minutes. Thereafter, the cells were treated with the same solution containing a drug for 60 minutes, then the supernatant was removed, and the increase in cAMP in cells was quantified using a Cysbio cAMP HiRange kit.

As to the maximum efficacy of compounds tested, multiple concentration assessment for the compounds of the present invention was carried out, thereby assessing the relative activation level (%) to the maximum effect of oleoylethanolamide (OEA), an endogenous ligand of GPR119.

The results are shown in Table 2, and it can be seen therefrom that the 67 compounds of the Examples represent excellent activities with maximum activities at least equivalent to OEA at 1 nM to 10 nM.

TABLE 2

Screening result for human GPR119 activation ability

| Example | hGPR119 activation ability (cAMP assay) Relative Response % vs OEA | |
|---|---|---|
| | 1 nM | 10 nM |
| 1 | 50.7 | 115.8 |
| 2 | 34.8 | 113.3 |
| 3 | 192.0 | 47.8 |
| 4 | 79.6 | 166.8 |
| 5 | 44.6 | 150.5 |
| 6 | 33.5 | 102.2 |
| 7 | 51.3 | 170.1 |
| 8 | 143.8 | 393.1 |
| 9 | 97.1 | 240.8 |
| 10 | 192.5 | 266.0 |
| 11 | 184.0 | 265.8 |
| 12 | 116.3 | 232.5 |
| 13 | 49.4 | 126.0 |
| 14 | 96.0 | 130.9 |
| 15 | 87.7 | 183.8 |
| 16 | 108.5 | 321.0 |
| 17 | 116.2 | 216.2 |
| 18 | 303.0 | 436.3 |
| 19 | 46.5 | 312.9 |
| 20 | 235.0 | 413.1 |
| 21 | 159.7 | 335.7 |
| 22 | 54.9 | 177.8 |
| 23 | 78.3 | 141.3 |
| 24 | 132.3 | 309.1 |
| 25 | 158.9 | 274.0 |
| 26 | 67.8 | 164.6 |
| 27 | 9.4 | 122.8 |
| 28 | 23.8 | 114.8 |
| 29 | 75.3 | 172.8 |
| 30 | 102.9 | 171.6 |
| 31 | 59.4 | 115.8 |
| 32 | 200.6 | 288.1 |
| 33 | 66.8 | 108.5 |
| 34 | 82.1 | 133.6 |
| 35 | 52.5 | 118.2 |
| 36 | 66.4 | 174.1 |
| 37 | 52.1 | 306.9 |
| 38 | 102.5 | 119.5 |
| 39 | 120.5 | 200.6 |
| 40 | 63.7 | 206.2 |
| 41 | 74.4 | 203.4 |
| 42 | 127.1 | 150.2 |
| 43 | 260.1 | 538.0 |
| 44 | 492.7 | 830.3 |
| 45 | 155.9 | 329.7 |
| 46 | 208.8 | 238.6 |
| 47 | 66.0 | 218.5 |
| 48 | 162.8 | 441.0 |
| 49 | 83.4 | 120.7 |
| 50 | 120.2 | 308.2 |
| 51 | 90.7 | 179.8 |
| 52 | 191.1 | 294.8 |
| 53 | 94.3 | 154.4 |
| 54 | 75.1 | 240.6 |
| 55 | 168.2 | 266.5 |
| 56 | 264.8 | 372.8 |
| 57 | 255.3 | 394.9 |
| 58 | 698.9 | 1066.2 |
| 59 | 140.3 | 329.1 |
| 60 | 285.3 | 516.1 |
| 61 | 98.1 | 185.5 |
| 62 | 88.8 | 169.3 |
| 63 | 113.7 | 228.0 |
| 64 | 77.0 | 178.7 |
| 65 | 78.1 | 189.3 |
| 66 | 95.6 | 119.6 |

<Experimental Example 2>Assessment of glucose tolerance improvement effect in mouse As one of anti-diabetic effect indicators, the glucose tolerance improvement effect of the above compounds was evaluated in 7-week male laboratory mouse (C57BL/6 mouse), as the effect of improving postprandial glycemic control ability.

The laboratory mouse was fasted from the day before the experiment for 16-17 hours. The compound of the present invention was orally administered 30 minutes before administrating glucose, and after 30 minutes, a glucose solution (2 g/kg/10 ml) was orally administered. A drug was prepared by suspending in a 10% Gelucire solution. At the times immediately before drug administration, immediately before glucose solution administration, 15 minutes, 30 minutes, 60 minutes, 90 minutes, and 120 minutes after glucose administration, the whole blood glucose levels was measured from tail vein using a blood glucose meter (AccuChek Active, Roche Diagnostics), and the area under the curve of a temporal blood glucose curve was calculated. From the calculated area under the blood glucose curve, the area under the blood glucose curve of a negative control group to which no glucose solution was administered was subtracted, and inhibitory activity against blood glucose increase of a control group to which only the 10% Gelucire solution and glucose solution were administered was calculated as a percentage, thereby evaluating the glucose tolerance improvement efficacy of a drug.

The results are shown in Table 3, in which the glucose tolerance improvement effect represented at a dose of 10 mg/kg was represented by classifying into three groups, under 30%, more than 30% under 40%, and more than 40%. A significant glucose tolerance improvement effect was identified in 22 compounds on which the experiment was carried out, and among those compounds, 16 compounds represented an excellent in vivo activity of 30% inhibitory dose of 10 mg/kg or less. In the following Table 3, A represents an inhibitory activity more than 40%, B represents an inhibitory activity more than 30% under 40% and C represents an inhibitory activity under 30%.

TABLE 3

Results of glucose tolerance improvement efficacy screening in mouse

| Example | Glucose tolerance improvement (Inhibition % @10 mg/kg) |
|---|---|
| 4 | C |
| 5 | A |
| 7 | C |
| 11 | C |
| 12 | A |
| 13 | B |
| 15 | A |
| 19 | B |
| 22 | B |
| 23 | A |
| 24 | C |
| 25 | C |
| 28 | C |
| 38 | C |
| 40 | B |
| 42 | A |
| 43 | A |
| 46 | A |
| 47 | A |
| 51 | A |
| 55 | B |
| 57 | B |

As shown in the above Tables 2 and 3, it was confirmed that the novel compounds synthesized in Examples 1 to 67, the isomers thereof, or the pharmaceutically acceptable salts thereof have agonistic activities to the GPR119. Furthermore, the excellent glucose tolerance improvement effect was confirmed in many compounds of the Examples on which the experiment was carried out. Accordingly, the above compounds of the Examples are expected to have a high treatment effect or prevention effect on metabolic diseases such as obesity, diabetes, hypertension, cardiovascular diseases, a hemostatic disorder, dyslipidemia and the like.

The present invention has been described in detail in specific parts, and it is obvious that such specific technique is only a preferred exemplary embodiment to a person skilled in the art, without limiting the scope of the present invention. Thus, the substantial scope of the present invention will be defined by the appended claims and their equivalents.

The invention claimed is:

1. A compound represented by Chemical Formula 1:

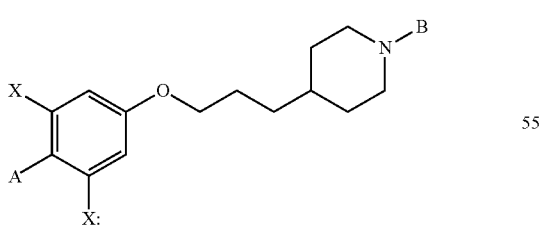

Chemical Formula 1 or a pharmaceutically acceptable salt or stereoisomer thereof,
wherein:
A is oxadiazolyl, dihydrooxazolyl, thiazolyl or thiadiazolyl, each optionally and independently substituted by one or more substituents selected from the group consisting of (i) halogen, (ii) C1-C6 alkyl, optionally substituted by halogen or C1-C6 alkoxy, and (iii) C1-C6 alkyl-OH, optionally substituted by halogen or C1-C6 alkoxy;
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and
each X is independently F, Cl, Br or I.

2. The compound of claim 1, or a pharmaceutically acceptable salt or stereoisomer thereof, wherein:
A is

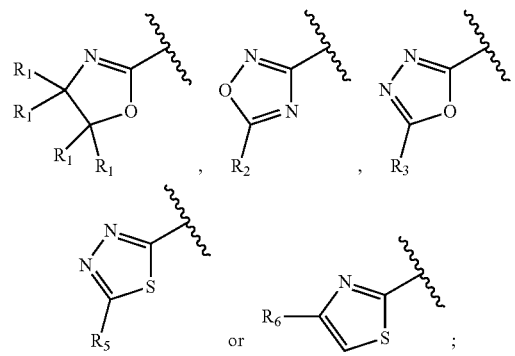

and
$R^1$, $R^2$, $R^3$, $R^5$ and $R^6$ are each independently (i) hydrogen, (ii) halogen, (iii) C1-C6 alkyl, optionally substituted by halogen or C1-C6 alkoxy, and (iv) C1-C6 alkyl-OH, optionally substituted by halogen or C1-C6 alkoxy.

3. The compound of claim 1, or a pharmaceutically acceptable salt or stereoisomer thereof, wherein A is oxadiazolyl.

4. The compound of claim 1, or a pharmaceutically acceptable salt or stereoisomer thereof, wherein:
B is

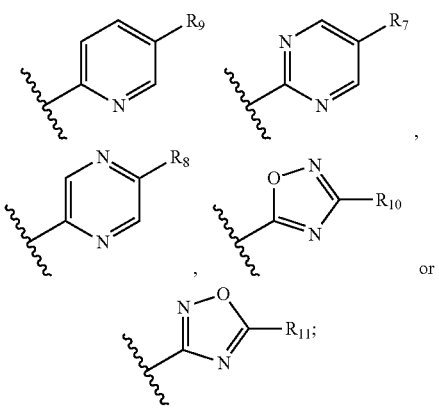

and
$R_7$, $R_8$, R9, $R_{10}$ and $R_{11}$ are independently (i) hydrogen, (ii) halogen, (iii) C1-C6 alkyl, optionally substituted by halogen, C1-C6 alkyl or C1-C6 alkoxy, (iv) C1-C6 alkyl-OH, optionally substituted by halogen, C1-C6 alkyl or C1-C6 alkoxy, (v) C1-C6 alkoxy, optionally substituted by halogen, C1-C6 alkyl or C1-C6 alkoxy, and (vi) oxadiazolyl, optionally substituted by halogen, C1-C6 alkyl or C1-C6 alkoxy.

5. The compound of claim 1, or a pharmaceutically acceptable salt or stereoisomer thereof, wherein:
A is oxadiazolyl, dihydrooxazolyl, thiazolyl or thiadiazolyl; and
B is pyridinyl, pyrimidinyl or oxadiazolyl.

6. The compound of claim 1, or a pharmaceutically acceptable salt or stereoisomer thereof, wherein each X is independently F.

7. The compound of claim 1, or a pharmaceutically acceptable salt or stereoisomer thereof, wherein:
A is oxadiazolyl, substituted by C1-C6 alkyl;
B is pyrimidinyl, substituted by C1-C6 alkyl; and
each X is independently F.

8. The compound of claim 1, wherein the compound is selected from the group consisting of the following compounds:

2-(4-(3-(1-(5-ethylpyrimidin-2-yl)piperidin-4-yl)propoxy)-2,6-difluorophenyl)-4,5-dihydroazole,
(R)-2-(4-(3-(1-(5-ethylpyrimidin-2-yl)piperidin-4-yl)propoxy)-2,6-difluorophenyl)-4-methyl-4,5-dihydrooxazole,
(S)-2-(4-(3-(1-(5-ethylpyrimidin-2-yl)piperidin-4-yl)propoxy)-2,6-difluorophenyl)-4-methyl-4,5-dihydrooxazole,
(S)-2-(4-(3-(1-(5-ethylpyrimidin-2-yl)piperidin-4-yl)propoxy)-2,6-difluorophenyl)-5-methyl-4,5-dihydrooxazole,
(R)-2-(4-(3-(1-(5-ethylpyrimidin-2-yl)piperidin-4-yl)propoxy)-2,6-difluorophenyl)-5-methyl-4,5-dihydrooxazole,
2-(4-(3-(1-(5-ethylpyrimidin-2-yl)piperidin-4-yl)propoxy)-2,6-difluorophenyl)-5,5-dimethyl-4,5-dihydrooxazole,
(R)-(2-(4-(3-(1-(5-ethylpyrimidin-2-yl)piperidin-4-yl)propoxy)-2,6-difluorophenyl)-4,5-dihydrooxazol-5-yl)methanol,
(S)-(2-(4-(3-(1-(5-ethylpyrimidin-2-yl)piperidin-4-yl)propoxy)-2,6-difluorophenyl)-4,5-dihydrooxazol-5-yl)methanol,
(R)-3-(2-(4-(3 -(3,5-difluoro-4-(5-methyl-4,5-dihydrooxazol-2-yl)phenoxy)propyl)piperidin-1-yl)pyrimidin-5-yl)-5-isobutyl-1,2,4-oxadiazole,
(R)-5-(4-(3 -(3,5-difluoro-4-(4-methyl-4,5 -dihydrooxazol-2-yl)phenoxy)propyl)piperidin -1-yl)-3-isopropyl-1,2,4-oxadiazole,
(S)-5-(4-(3 -(3,5 -difluoro-4-(5-methyl-4,5-dihydrooxazol-2-yl)phenoxy)propyl)piperidin -1-yl)-3-isopropyl-1,2,4-oxadiazole,
5-(4-(3-(4-(5,5-dimethyl-4,5-dihydrooxazol-2-yl)-3,5-difluorophenoxy)propyl)piperidin -1-yl)-3-isopropyl-1,2,4-oxadiazole,
3-(4-(3 -(1-(5 -ethylpyrimidin-2-yl)piperidin-4-yl)propoxy)-2,6-difluorophenyl)-5-methyl -1,2,4-oxadiazole,
3-(4-(3-(1-(5-ethylpyrimidin-2-yl)piperidin-4-yl)propoxy)-2,6-difluorophenyl)-5-propyl -1,2,4-oxadiazole,
3-(4-(3-(1-(5-ethylpyrimidin-2-yl)piperidin-4-yl)propoxy)-2,6-difluorophenyl)-5-isopropyl -1,2,4-oxadiazole,
5-(tert-butyl)-3-(4-(3-(1-(5-ethylpyrimidin-2-yl)piperidin-4-yl)propoxy)-2,6-difluorophenyl) -1,2,4-oxadiazole,
(3-(4-(3 -(1-(5-ethylpyrimidin-2-yl)piperidin-4-yl)propoxy)-2,6-difluorophenyl)-1,2,4-oxadiazol-5-yl)methanol,
2-(3-(4-(3-(1-(5-ethylpyrimidin-2-yl)piperidin-4-yl)propoxy)-2,6-difluorophenyl)-1,2,4-oxadiazol-5-yl)ethan-1-ol,
(S)-1-(3-(4-(3-(1-(5-ethylpyrimidin-2-yl)piperidin-4-yl)propoxy)-2,6-difluorophenyl) -1,2,4-oxadiazol-5-yl)propan-1-ol,
(R)-1-(3-(4-(3-(1-(5-ethylpyrimidin-2-yl)piperidin-4-yl)propoxy)-2,6-difluorophenyl) -1,2,4-oxadiazol-5-yl)propan-2-ol,
(S)-1-(3-(4-(3-(1-(5-ethylpyrimidin-2-yl)piperidin-4-yl)propoxy)-2,6-difluorophenyl)-1,2,4-oxadiazol-5-yl)propan-2-ol,
2-(3-(4-(3-(1-(5-ethylpyrimidin-2-yl)piperidin-4-yl)propoxy)-2,6-difluorophenyl)-1,2,4-oxadiazol-5-yl)-2-methylpropan-1-ol,
3-(2,6-difluoro-4-(3-(1-(5-propylpyrimidin-2-yl)piperidin-4-yl)propoxy)phenyl)-5-isopropyl -1,2,4-oxadiazole,
3-(2,6-difluoro-4-(3-(1-(5-pentylpyrimidin-2-yl)piperidin-4-yl)propoxy)phenyl)-5-isopropyl -1,2,4-oxadiazole,
3-(2,6-difluoro-4-(3-(1-(5-(trifluoromethyl)pyrimidin-2-yl)piperidin-4-yl)propoxy)phenyl) -5-isopropyl-1,2,4-oxadiazole,
3-(2,6-difluoro-4-(3-(1-(5-methoxypyrimidin-2-yl)piperidin-4-yl)propoxy)phenyl)-5-isopropyl -1,2,4-oxadiazole,
3-(2,6-difluoro-4-(3-(1-(5-isopropoxypyrimidin-2-yl)piperidin-4-yl)propoxy)phenyl) -5-isopropyl-1,2,4-oxadiazole,
3-(4-(3-(1-(5-chloropyrimidin-2-yl)piperidin-4-yl)propoxy)-2,6-difluorophenyl)-5-isopropyl -1,2,4-oxadiazole,
3-(4-(3-(1-(5-bromopyrimidin-2-yl)piperidin-4-yl)propoxy)-2,6-difluorophenyl)-5-isopropyl -1,2,4-oxadiazole,
3-(2,6-difluoro-4-(3-(1-(5-(5-isobutyl-1,2,4-oxadiazol-3-yl)pyrimidin-2-yl)piperidin -4-yl)propoxy)phenyl)-5-methyl-1,2,4-oxadiazole,
3-(2,6-difluoro-4-(3-(1-(5-(5-isobutyl-1,2,4-oxadiazol-3-yl)pyrimidin-2-yl)piperidin -4-yl)propoxy)phenyl)-5-ethyl-1,2,4-oxadiazole,
3-(2,6-difluoro-4-(3-(1-(5-(5-isobutyl-1,2,4-oxadiazol-3-yl)pyrimidin-2-yl)piperidin -4-yl)propoxy)phenyl)-5-isopropyl-1,2,4-oxadiazole,
5-(sec-butyl)-3-(2,6-difluoro-4-(3-(1-(5-(5-isobutyl-1,2,4-oxadiazol-3-yl)pyrimidin-2-yl)piperidin-4-yl)propoxy)phenyl)-1,2,4-oxadiazole,
3-(2,6-difluoro-4-(3-(1-(5-(5-isobutyl-1,2,4-oxadiazol-3-yl)pyrimidin-2-yl)piperidin -4-yl)propoxy)phenyl)-5-(methoxymethyl)-1,2,4-oxadiazole,
(S)-1-3-(2,6-difluoro-4-(3-(1-(5-(5-isobutyl-1,2,4-oxadiazol-3-yl)pyrimidin-2-yl)piperidin -4-yl)propoxy)phenyl)-1,2,4-oxadiazol-5-yl)propan-1-ol,
2-(3-(2,6-difluoro-4-(3-(1-(5-(5-isobutyl-1,2,4-oxadiazol-3-yl)pyrimidin-2-yl)piperidin -4-yl)propoxy)phenyl)-1,2,4-oxadiazol-5-yl)-2-methylpropan-1-ol,
3-(4-(3-(1-(5-chloropyrazin-2-yl)piperidin-4-yl)propoxy)-2,6-difluorophenyl)-5-isopropyl -1,2,4-oxadiazole, 3-(2,6-difluoro-4-(3-(1-(5-(trifluoromethyl)pyridin-2-yl)piperidin-4-yl)propoxy)phenyl -5-isopropyl-1,2,4-oxadiazole,
3-(2,6-difluoro-4-(3-(1-(3-isopropyl-1,2,4-oxadiazol-5-yl)piperidin-4-yl)propoxy)phenyl) -5-methyl-1,2,4-oxadiazole,
3-(2,6-difluoro-4-(3-(1-(3-isopropyl-1,2,4-oxadiazol-5-yl)piperidin-4-yl)propoxy)phenyl) -5-isopropyl-1,2,4-oxadiazole,
(3-(2,6-difluoro-4-(3-(1-(3-isopropyl-1,2,4-oxadiazol-5-yl)piperidin-4-yl)propoxy)phenyl) -1,2,4-oxadiazol-5-yl)methanol,
2-(4-(3-(1-(5-ethylpyrimidin-2-yl)piperidin-4-yl)propoxy)-2,6-difluorophenyl)-5-methyl -1,3,4-oxadiazole,
2-ethyl-5-(4-(3-(1-(5-ethylpyrimidin-2-yl)piperidin-4-yl)propoxy)-2,6-difluorophenyl) -1,3,4-oxadiazole,
2-(4-(3-(1-(5-ethylpyrimidin-2-yl)piperidin-4-yl)propoxy)-2,6-difluorophenyl)-5-isopropyl -1,3,4-oxadiazole,
5-(4-(3-(1-(5-ethylpyrimidin-2-yl)piperidin-4-yl)propoxy)-2,6-difluorophenyl)-N-isopropyl -1,3,4-oxadiazol-2-amine,
2-(2,6-difluoro-4-(3-(1-(5-(trifluoromethyl)pyrimidin-2-yl)piperidin-4-yl)propoxy)phenyl) -5-methyl-1,3,4-oxadiazole,
2-(2,6-difluoro-4-(3-(1-(5-(trifluoromethyl)pyrimidin-2-yl)piperidin-4-yl)propoxy)phenyl) -5-ethyl-1,3,4-oxadiazole,
2-(2,6-difluoro-4-(3-(1-(5-(trifluoromethyl)pyrimidin-2-yl)piperidin-4-yl)propoxy)phenyl) -5-isopropyl-1,3,4-oxadiazole,
2-(4-(3-(1-(5-chloropyrazin-2-yl)piperidin-4-yl)propoxy)-2,6-difluorophenyl)-5-methyl -1,3,4-oxadiazole,
2-(4-(3-(1-(5-chloropyrazin-2-yl)piperidin-4-yl)propoxy)-2,6-difluorophenyl)-5-ethyl -1,3,4-oxadiazole,
2-(4-(3-(1-(5-chloropyrazin-2-yl)piperidin-4-yl)propoxy)-2,6-difluorophenyl)-5-isopropyl -1,3,4-oxadiazole,
5-(4-(3-(3,5-difluoro-4-(5-methyl-1,3,4-oxadiazol-2-yl)phenoxy)propyl)piperidin-1-yl) -3-propyl-1,2,4-oxadiazole,
5-(4-(3-(3,5-difluoro-4-(5-ethyl-1,3,4-oxadiazol-2-yl)phenoxy)propyl)piperidin-1-yl) -3-propyl-1,2,4-oxadiazole,
5-(4-(3-(3,5-difluoro-4-(5-isopropyl-1,3,4-oxadiazol-2-yl)phenoxy)propyl)piperidin-1-yl)-3-propyl-1,2,4-oxadiazole,
5-(4-(3-(3,5-difluoro-4-(5-methyl-1,3,4-oxadiazol-2-yl)phenoxy)propyl)piperidin-1-yl -3-isopropyl-1,2,4-oxadiazole,
5-(4-(3-(4-(5-ethyl-1,3,4-oxadiazol-2-yl)-3,5-difluorophenoxy)propyl)piperidin-1-yl) -3-isopropyl-1,2,4-oxadiazole,
5-(4-(3-(3,5-difluoro-4-(5-isopropyl-1,3,4-oxadiazol-2-yl)phenoxy)propyl)piperidin-1-yl)-3-isopropyl-1,2,4-oxadiazole,
5-(4-(3-(3,5-difluoro-4-(5-methyl-1,3,4-oxadiazol-2-yl)phenoxy)propyl)piperidin-1-yl) -3-(2,2,2-trifluoroethyl)-1,2,4-oxadiazole,
3-(4-(3-(3,5-difluoro-4-(5-isopropyl-1,3,4-oxadiazol-2-yl)phenoxy)propyl)piperidin-1-yl)-5-isopropyl-1,2,4-oxadiazole,
2-(4-(3-(1-(5-ethylpyrimidin-2-yl)piperidin-4-yl)propoxy)-2,6-difluorophenyl)-5-isopropyl -1,3,4-thiadiazole,
2-(2,6-difluoro-4-(3-(1-(5-propylpyrimidin-2-yl)piperidin-4-yl)propoxy)phenyl)-5-isopropyl -1,3,4-thiadiazole,
2-(2,6-difluoro-4-(3-(1-(5-pentylpyrimidin-2-yl)piperidin-4-yl)propoxy)phenyl)-5-isopropyl -1,3,4-thiadiazole,
2-(2,6-difluoro-4-(3-(1-(5-fluoropyrimidin-2-yl)piperidin-4-yl)propoxy)phenyl)-5-isopropyl -1,3,4-thiadiazole,
2-(2,6-difluoro-4-(3-(1-(5-(trifluoromethyl)pyrimidin-2-yl)piperidin-4-yl)propoxy)phenyl) -5-isopropyl-1,3,4-thiadiazole,
2-(2,6-difluoro-4-(3-(1-(5-(trifluoromethyl)pyridin-2-yl)piperidin-4-yl)propoxy)phenyl) -5-isopropyl-1,3,4-thiadiazole and
4-ethyl-2-(4-(3-(1-(5-ethylpyrimidin-2-yl)piperidin-4-yl)propoxy)-2,6-difluorophenyl) thiazole.
or a pharmaceutically acceptable salt or steroisomer thereof.

9. A pharmaceutical composition comprising as an effective component the compound of claim 1, or a pharmaceutically acceptable salt or stereoisomer thereof, and a pharmaceutically acceptable carrier or excipient.

10. A method for activating G protein-coupled receptor 119 in a subject, comprising administering to the subject in need thereof a therapeutically effective amount of the compound of claim 1, or a pharmaceutically acceptable salt or stereoisomer thereof.

11. The method of claim 10, wherein the subject has at least one metabolic disease or disorder selected from the group consisting of a cardiovascular disease, a hemostatic disorder, diabetes, obesity, hypertension and dyslipidemia.

12. A process for preparing a compound represented by Chemical Formula 1:

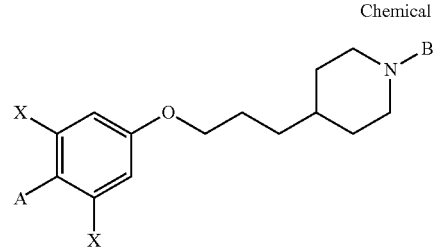

Chemical Formula 1 wherein:
A is oxadiazolyl, dihydrooxazolyl, thiazolyl or thiadiazolyl, each optionally and independently substituted by one or more substituents selected from the group consisting of (i) halogen, (ii) C1-C6 alkyl, optionally substituted by halogen or C1-C6 alkoxy, and (iii) C1-C6 alkyl-OH, optionally substituted by halogen or C1-C6 alkoxy;
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and
each X is independently F, Cl, Br or I;
the process comprising the following steps:
(i) reacting a compound represented by Chemical Formula 4:

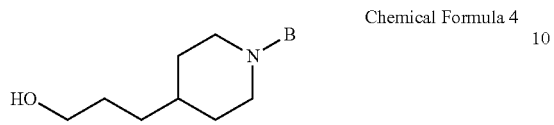

Chemical Formula 4 wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy;
with methanesulfonyl chloride in the presence of dichloromethane, to provide a compound represented by Chemical Formula 5:

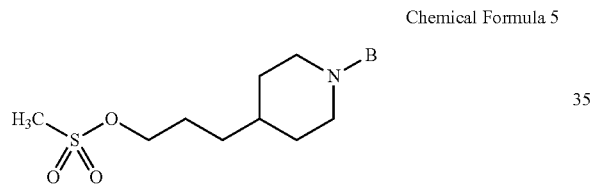

Chemical Formula 5 wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy;
(ii) reacting the compound represented by Chemical Formula 5 above with a compound represented by Chemical Formula 12a:

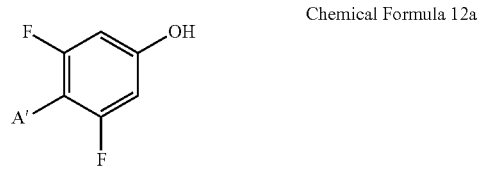

Chemical Formula 12a wherein:
A' is C(O)OC1-C6 alkyl, C(O)OH, a ketone group, halogen or CN;

in the presence of one or more bases selected from the group consisting of sodium carbonate, calcium carbonate, potassium carbonate and cesium carbonate, and one or more solvents selected from the group consisting of dimethyl sulfoxide, N,N-dimethyl formamide, N-methylpyrrolidin-2-one, tetrahydrofuran and 1,4-dioxane, to provide a compound represented by Chemical Formula 8:

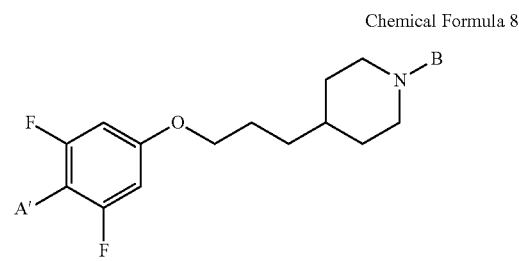

Chemical Formula 8 wherein:
A' is C(O)OC1-C6 alkyl, C(O)OH, a ketone group, halogen or CN; and
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and
(iiia) (1) reacting the compound represented by Chemical Formula 8 above, where A' is C(O)OC1-C6 alkyl, with an aqueous sodium hydroxide solution or an aqueous potassium hydroxide solution, followed by aqueous hydrochloric acid, in the presence of one or more solvents selected from the group consisting of methanol, ethanol, tetrahydrofuran and 1,4-dioxane, to provide a compound represented by Chemical Formula 8 above, where A' is C(O)OH;
(2) reacting the compound represented by Chemical Formula 8 above, where A' is C(O)OH, with a compound represented by Chemical Formula 13:

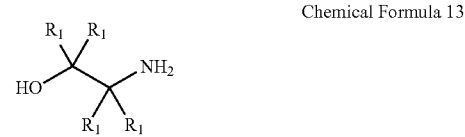

Chemical Formula 13 wherein:
each $R_1$ is independently (i) hydrogen, (ii) C1-C6 alkyl, optionally substituted by halogen or C1-C6 alkoxy, or (iii) C1-C6 alkyl-OH, optionally substituted by halogen or C1-C6 alkoxy;
in the presence of 1-ethyl-3-(3-dimethylaminopropyl)carbodiimide hydrochloride, hydroxybenzotriazole, triethylamine and one or more solvents selected from the group consisting of methanol, ethanol, tetrahydrofuran and 1,4-dioxane, to provide a compound represented by Chemical Formula 14:

Chemical Formula 14

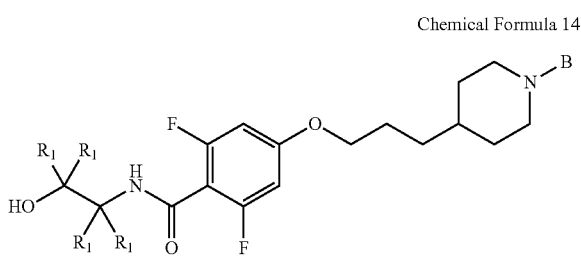

wherein:
each $R_1$ is independently (i) hydrogen, (ii) C1-C6 alkyl, optionally substituted by halogen or C1-C6 alkoxy, or (iii) C1-C6 alkyl-OH, optionally substituted by halogen or C1-C6 alkoxy; and
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy;
(3) reacting the compound represented by Chemical Formula 14 above with triphenylphosphine and 2,3-dichloro-5,6-dicyano-1,4-benzoquinone in the presence of dichloromethane, to provide the compound represented by Chemical Formula 1 above, where A is:

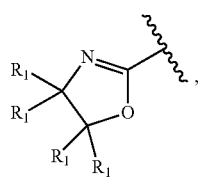

wherein:
each $R_1$ is independently (i) hydrogen, (ii) C1-C6 alkyl, optionally substituted by halogen or C1-C6 alkoxy, or (iii) C1-C6 alkyl-OH, optionally substituted by halogen or C1-C6 alkoxy; or
(iiib) (1) reacting the compound represented by Chemical Formula 8 above, where A' is CN, with hydroxylamine in the presence of one or more solvents selected from the group consisting of methanol, ethanol, tetrahydrofuran and 1,4-dioxane, to provide a compound represented by the Chemical Formula 15:

Chemical Formula 15

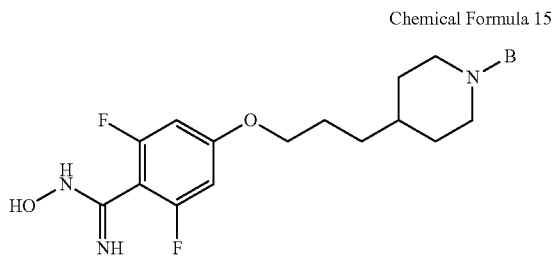

wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and
(2) reacting the compound represented by Chemical Formula 15 above with a compound represented by Chemical Formula 16:

Chemical Formula 16

wherein:
LG is halogen or —OC(O)C1-C6 alkyl; and
R2 is C1-C6 alkyl, optionally substituted by halogen or C1-C6 alkoxy, or (ii) C1-C6 alkyl-OH, optionally substituted by halogen or C1-C6 alkoxy;
with trimethylamine in the presence of dichloromethane, to provide the compound represented by Chemical Formula 1 above, where A is:

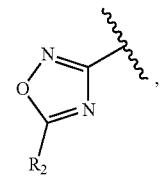

wherein:
R2 is (i) C1-C6 alkyl, optionally substituted by halogen or C1-C6 alkoxy, or (ii) C1-C6 alkyl-OH, optionally substituted by halogen or C1-C6 alkoxy; or
(iiic) (1) reacting the compound represented by Chemical Formula 8 above, where A' is C(O)OH, with hydrazine in the presence of 1-ethyl-3-(3-dimethylaminopropyp-carbodiimide hydrochloride, hydroxybenzotriazole and dichloromethane, to provide a compound represented by the Chemical Formula 17:

Chemical Formula 17

wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and (2) reacting the compound represented by Chemical Formula 17 above with:

(i) a compound represented by Chemical Formula 18:

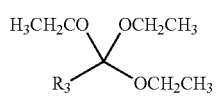

Chemical Formula 18 wherein:
R3 is C1-C6 alkyl; or (ii) a compound represented by Chemical Formula 19:

   Chemical Formula 19 wherein:
R3 is C1-C6 alkyl;
in the presence of triethylamine and water, to provide the compound represented by Chemical Formula 1 above, where A is:

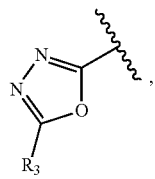

wherein:
R3 is C1-C6 alkyl; or (iiid) (1) reacting the compound represented by Chemical Formula 8 above, where A' is C(O)OH, with a compound represented by the formula:

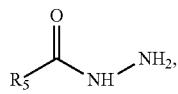

wherein:
R5 is C1-C6 alkyl;
in the presence of 1-ethyl-3-(3-dimethylaminopropyl)carbodiimide hydrochloride, hydroxybenzotriazole and dichloromethane, to provide a compound represented by Chemical Formula 20:

Chemical Formula 20

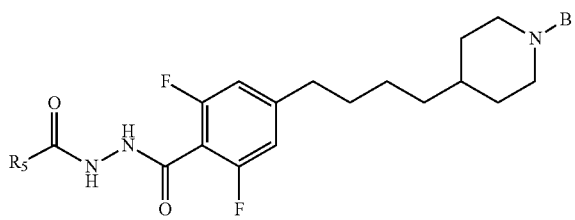

wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and R5 is C1-C6 alkyl; and (2) reacting the compound represented by Chemical Formula 20 above with a compound represented by Chemical Formula 21:

Chemical Formula 21

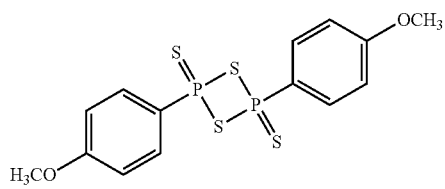

in the presence of xylene, to provide the compound represented by Chemical Formula 1 above, where A is:

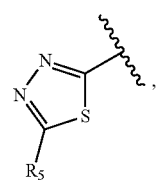

wherein:
R5 is C1-C6 alkyl; or (iiie) (1) reacting the compound represented by Chemical Formula 8 above, where A' is C(O)OH, with thionyl chloride in the presence of dichloromethane, to provide a compound represented by the Chemical Formula 22:

Chemical Formula 22

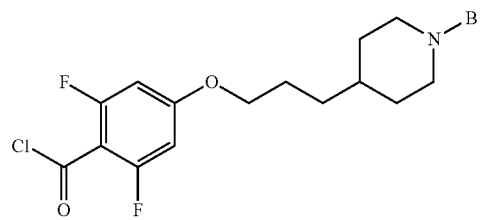

wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy;
(2) reacting the compound represented by Chemical Formula 22 above with sodium hydroxide and ammonium chloride in the presence of benzene, to provide a compound represented by Chemical Formula 23:

Chemical Formula 23

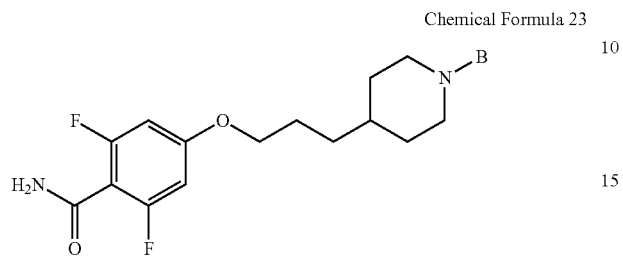

wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy;
(3) reacting the compound represented by Chemical Formula 23 above with a compound represented by Chemical Formula 21:

Chemical Formula 21

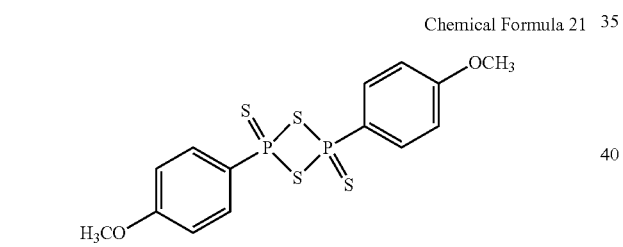

in the presence of tetrahydrofuran, to provide a compound represented by Chemical Formula 24

Chemical Formula 24

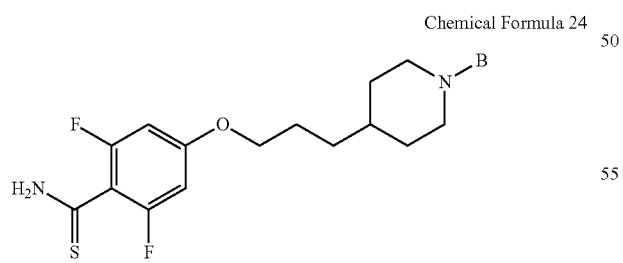

wherein:
B is pyridinyl, pyrimidinyl, pyrazinyl or oxadiazolyl, each optionally and independently substituted by one or more substituents selected from the group consisting of (i) halogen, (ii) C1-C6 alkyl, optionally substituted by halogen, C1-C6 alkyl or C1-C6 alkoxy, (iii) C1-C6 alkyl-OH, optionally substituted by halogen, C1-C6 alkyl or C1-C6 alkoxy, (iv) C1-C6 alkoxy, optionally substituted by halogen, C1-C6 alkyl or C1-C6 alkoxy, and (v) oxadiazolyl, optionally substituted by halogen, C1-C6 alkyl or C1-C6 alkoxy; and
(4) reacting the compound represented by Chemical Formula 24 above with a compound represented by Chemical Formula 25:

Chemical Formula 25

wherein:
LG is halogen or —OC(O)C1-C6 alkyl; and $R_6$ is C1-C6 alkyl;
in the presence of ethanol, to provide the compound represented by Chemical Formula 1 above, where A is:

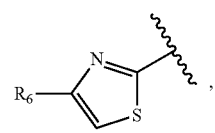

wherein:
$R_6$ is C1-C6 alkyl.
13. The process of claim 12, wherein:
A' is C(O)OC1-C6 alkyl or C(O)OH; and
A is

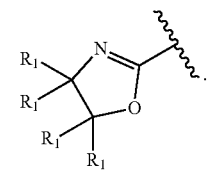

14. The process of claim 12, wherein:
A' is CN; and
A is

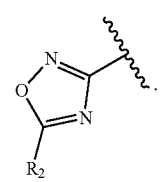

15. The process of claim 12, wherein:
A' is C(O)OC1-C6 alkyl or C(O)OH; and
A is;

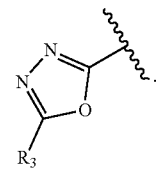

16. The process of claim 12, wherein:
A' is C(O)OC1-C6 alkyl or C(O)OH; and
A is
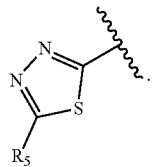
17. The process of claim 12, wherein:
A' is C(O)OC1-C6 alkyl or C(O)OH; and
A is
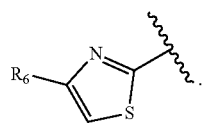
* * * * *